United States Patent
Tokunaga et al.

(10) Patent No.: US 6,576,656 B1
(45) Date of Patent: Jun. 10, 2003

(54) OXINDOLE DERIVATIVE

(75) Inventors: Teruhisa Tokunaga, Nishinomiya (JP); Takashi Umezome, Nishinomiya (JP); W. Ewan Hume, Nishinomiya (JP); Ryu Nagata, Nishinomiya (JP); Kazuhiko Okazaki, Nishinomiya (JP); Yasuyuki Ueki, Sanda (JP); Kazuo Kumagai, Sanda (JP)

(73) Assignee: Sumitomo Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/763,241

(22) PCT Filed: Aug. 18, 1999

(86) PCT No.: PCT/JP99/04443

§ 371 (c)(1),
(2), (4) Date: Mar. 22, 2001

(87) PCT Pub. No.: WO00/10975

PCT Pub. Date: Mar. 2, 2000

(30) Foreign Application Priority Data

Aug. 20, 1998 (JP) .......................... 10-234643

(51) Int. Cl.[7] ...................... A61K 31/40; C07D 209/38; C07D 401/04
(52) U.S. Cl. .................. 514/418; 514/235.2; 514/314; 514/339; 514/367; 514/397; 514/414; 544/144; 546/152; 546/167; 546/227.7; 548/159; 548/314.7; 548/454; 548/465; 548/466; 548/467; 548/486; 548/488; 548/491
(58) Field of Search ..................... 544/144; 546/152, 546/167, 227.7; 548/159, 314.7, 454, 465, 466, 467, 486, 488, 491; 514/235.2, 314, 339, 367, 397, 414, 418

(56) References Cited

U.S. PATENT DOCUMENTS 3,891,644 A * 6/1975 White .......................... 544/252
3,976,645 A    8/1976 White .......................... 544/252
5,283,241 A    2/1994 Bochis et al. ............... 514/183

FOREIGN PATENT DOCUMENTS

GB        A1125671        8/1968

OTHER PUBLICATIONS

Gevorkyan et al. "Anticonvulsant activity of oxindole derivatives . . . " CA 110:87982 (1989).*
Bundgaard "Design of prodrugs" Elsevier (1986) p. 1, 24–26.*

N. Hirose et al., Chem.Pharm.Bull. vol. 21(5);(1973) pp. 960–971.

I.A. Cliffe et al., J.Chem.Soc.Perkin Trans.1 (1991); pp. 1975–1979.

* cited by examiner

*Primary Examiner*—Ceila Chang
(74) *Attorney, Agent, or Firm*—Birch, Stewart, Kolasch & Birch, LLP

(57) ABSTRACT

An oxindole of Formula 1 or a prodrug thereof, or a pharmaceutically acceptable salt thereof is useful for growth hormone releaser:

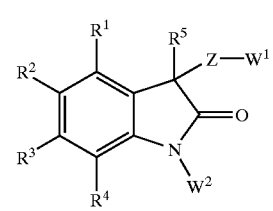

(1)

wherein $R^1$, $R^2$, $R^3$ and $R^4$ are independently hydrogen, optionally substituted alkyl etc;

$R^5$ is optionally substituted aryl or optionally substituted heteroaryl;

Z is —O— or —NH—;

one of $W^1$ and $W^2$ is hydrogen, alkyl or —Y—CON($R^{10}$)$R^{11}$;

the other of $W^1$ and $W^2$ is

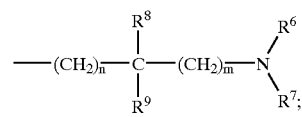

n is 1, 2 or 3; m is 0, 1, 2 or 3;

Y is single bond or $C_1$–$C_3$ alkylene;

$R^6$ and $R^7$ are independently hydrogen, optionally substituted alkyl etc;

$R^8$ and $R^9$ are independently hydrogen, optionally substituted alkyl etc;

$R^{10}$ and $R^{11}$ are independently hydrogen, alkyl etc.

12 Claims, No Drawings

OXINDOLE DERIVATIVE

This application is the national phase under 35 U.S.C. §371 of PCT International Application No. PCT/JP99/04443 which has an International filing date of Aug. 18, 1999, which designated the United States of America.

TECHNICAL FIELD

The present invention relates to an oxindole derivative useful for growth hormone releaser etc.

BACKGROUND ART

Various factors are related to growth in individuals. However, growth hormone should apparently be the most important factor for growing, since surplus secretion of growth hormone may result in gigantism or acromegaly, and deficiency in growth hormone may result in dwarfism. Growth hormone is known to have basic effects on the metabolic processees of the body: to increase rate of protein synthesis, to decrease rate of carbohydrate utilization, and to increase mobilization of free fatty acids and use of fatty acids for energy.

Various compounds such as arginine, L-3,4-dihydroxyphenylalanine (L-DOPA), glucagon, vasopressin, and insulin induced hypoglycemia are known to cause a release of growth hormone. Activities such as sleep and exercise are also known to release growth hormone. These compounds and activities indirectly cause growth hormone to be released from the pituitary by acting on the hypothalamus in various ways such as to decrease somatostatin secretion and to increase the secretion of the known secretagogue growth hormone releasing factor (GRF) or an unknown endogenous growth hormone-releasing hormone.

Providing exogenous growth hormone is used as one way to increase levels of growth hormone. The sources of growth hormone used are either from extractions of pituitary glands of cadavers or recombinant growth hormone. However, the resulting growth hormone is very expensive and the extracted products from pituitary glands have risks that diseases associated with the source of the pituitary gland could be transmitted to the recipient of the growth hormone. Growth hormone should be given by injection or by a nasal spray, because its oral administration is difficult.

Another way to increase levels of growth hormone is to administer compounds which stimulate the release of endogenous growth hormone such as GRF or its derivatives (Schoen W. R. et. al., "Growth hormone secretagogues" in Annual Reports in Medicinal Chemistry: Academic Press, Vol. 28, Chapter 19, 1993) and peptidyl compounds (U.S. Pat. No. 4,411,890). These peptides are considerably smaller than growth hormones, but are still susceptible to various proteases. Therefore, their potential for oral bioavailability is low.

WO 94/01369 discloses non-peptide compounds useful as growth hormone releasers. Though these compounds are stable under various physiological environments and applicable parenterally, intranasally or orally, these compounds have not been approved as a drug.

J. Chem. Soc. Perkin Trans. 1, 1975–1979(1991) describes that benzodiazocine derivatives were formed by heating oxindole derivatives in the presence of acid catalyst.

Chem. Pharm. Bull., 21, 960–971(1973) describes that oxindole derivatives without any substituents on its benzene ring have analgesic and anti-inflammatory effects.

DETAILED DESCRIPTION OF THE INVENTION

The inventors of the present invention have intensively carried out research on growth hormone releasers, and found that oxindole derivatives or prodrugs thereof, and pharmaceutically acceptable salts thereof are growth hormone releasers which are applicable as a medicine. Thus, the present invention has been accomplished.

That is, the present invention is as follows:

[1] An oxindole derivative of Formula 1 or a prodrug thereof, or a pharmaceutically acceptable salt thereof:

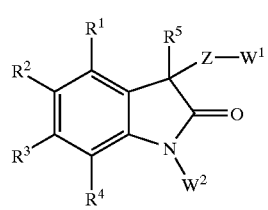

(1)

wherein $R^1$, $R^2$, $R^3$ and $R^4$ are the same or different and each is independently hydrogen, optionally substituted alkyl, optionally substituted alkenyl, optionally substituted alkynyl, optionally substituted aryl, optionally substituted heteroaryl, halogen, cyano, nitro, hydroxy, optionally substituted amino, alkoxy, alkanoyl, alkoxycarbonyl, optionally substituted sulfamoyl, optionally substituted carbamoyl, alkylthio, alkylsulfinyl, alkylsulfonyl, alkylsulfonylamino or alkanoylamino, provided that all of $R^1$, $R^2$, $R^3$ and $R^4$ are not simultaneously hydrogen;

$R^5$ is optionally substituted aryl or optionally substituted heteroaryl;

Z is —O— or —NH—;

one of $W^1$ and $W^2$ is hydrogen, alkyl or —Y—CON($R^{10}$)$R^{11}$;

the other of $W^1$ and $W^2$ is

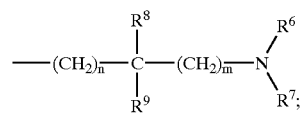

n is 1, 2 or 3; m is 0, 1, 2 or 3;

Y is single bond or $C_1$–$C_3$ alkylene;

$R^6$ and $R^7$ are the same or different and each is independently hydrogen, optionally substituted alkyl or optionally substituted cycloalkyl; or $R^6$ and $R^7$ are taken together with the adjacent nitrogen atom to form optionally substituted saturated heterocyclic ring;

$R^8$ and $R^9$ are the same or different and each is independently hydrogen or optionally substituted alkyl; or $R^8$ and $R^9$ are taken together with the adjacent carbon atom to form optionally substituted cycloalkane or optionally substituted saturated heterocyclic ring;

$R^8$ and $R^6$ may be taken together to form $C_1$–$C_5$ alkylene in which case $R^7$ is hydrogen, optionally substituted alkyl or optionally substituted cycloalkyl, and $R^9$ is hydrogen or optionally substituted alkyl;

$R^{10}$ and $R^{11}$ are the same or different and each is independently hydrogen or alkyl; or $R^{10}$ and $R^{11}$ are taken together with the adjacent nitrogen atom to form optionally substituted saturated heterocyclic ring.

[2] An oxindole derivative or a prodrug thereof, or a pharmaceutically acceptable salt thereof according to

[1] wherein $R^1$, $R^2$, $R^3$ and $R^4$ are independently hydrogen, alkyl optionally substituted by halogen, optionally substituted alkenyl, optionally substituted alkynyl, optionally substituted carbamoyl, halogen, cyano, nitro, alkanoyl, alkoxycarbonyl, alkylsulfinyl or alkylsulfonyl, provided that all of $R^1$, $R^2$, $R^3$ and $R^4$ are not simultaneously hydrogen.

[3] An oxindole derivative or a prodrug thereof, or a pharmaceutically acceptable salt thereof according to [1] wherein $R^1$, $R^2$, $R^3$ and $R^4$ are independently hydrogen, trifluoromethyl, carbamoyl, halogen, 4-carbamoyl-1-butynyl, 4-alkylcarbamoyl-1-butynyl, 4-dialkylcarbamoyl-1-butynyl, 4-morpholinocarbonyl-1-butynyl, —C≡C—$(CH_2)_k$—Q, wherein k is 1 or 2; Q is hydroxy, alkylsulfonyl, alkanoylamino, alkylureido, 2-oxo-1-imidazolidinyl or 2-oxo-1,3-oxazolin-3-yl, provided that all of $R^1$, $R^2$, $R^3$ and $R^4$ are not simultaneously hydrogen.

[4] An oxindole derivative or a prodrug thereof, or a pharmaceutically acceptable salt thereof according to [3] wherein both of $R^2$ and $R^4$ are hydrogen.

[5] An oxindole derivative or a prodrug thereof, or a pharmaceutically acceptable salt thereof according to [1] wherein both of $R^2$ and $R^4$ are hydrogen; $R^1$ is trifluoromethyl, chlorine or bromine; and $R^3$ is carbamoyl, halogen, 4-carbamoyl-1-butynyl, 4-alkylcarbamoyl-1-butynyl, 4-dialkylcarbamoyl-1-butynyl, 4-morpholinocarbonyl-1-butynyl, —C≡C—$(CH_2)_k$—Q, wherein k and Q are as defined above.

[6] An oxindole derivative or a prodrug thereof, or a pharmaceutically acceptable salt thereof according to [1] wherein both of $R^2$ and $R^4$ are hydrogen; $R^1$ is trifluoromethyl, chlorine or bromine; and $R^3$ is carbamoyl.

[7] An oxindole derivative or a prodrug thereof, or a pharmaceutically acceptable salt thereof according to any one of [1] to [6] wherein $R^5$ is optionally substituted phenyl or optionally substituted 2-naphthyl.

[8] An oxindole derivative or a prodrug thereof, or a pharmaceutically acceptable salt thereof according to any one of [1] to [6] wherein $R^5$ is phenyl optionally substituted by halogen(s) and/or trifluoromethyl(s) or 2-naphthyl optionally substituted by halogen(s) and/or trifluoromethyl(s).

[9] An oxindole derivative or a prodrug thereof, or a pharmaceutically acceptable salt thereof according to any one of [1] to [8] wherein $R^6$ and $R^7$ are independently optionally substituted alkyl or optionally substituted cycloalkyl; or $R^6$ and $R^7$ are taken together with the adjacent nitrogen atom to form optionally substituted saturated heterocyclic ring.

[10] An oxindole derivative or a prodrug thereof, or a pharmaceutically acceptable salt thereof according to any one of [1] to [9] wherein one of $W^1$ and $W^2$ is hydrogen or —$CONHR^{10}$; and the other of $W^1$ and $W^2$ is

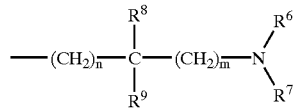

wherein n, m, $R^6$, $R^7$, $R^8$, $R^9$ and $R^{10}$ are as defined in [1].

[11] An oxindole derivative or a prodrug thereof, or a pharmaceutically acceptable salt thereof according to any one of [1] to [9] wherein one of $W^1$ and $W^2$ is hydrogen; and the other of $W^1$ and $W^2$ is

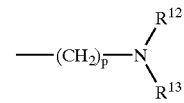

wherein p is an integer of 2 to 7; and $R^{12}$ and $R^{13}$ are independently optionally substituted alkyl.

[12] An oxindole derivative or a prodrug thereof, or a pharmaceutically acceptable salt thereof according to any one of [1] to [9],
wherein
(1) $W^1$ is hydrogen; and $W^2$ is

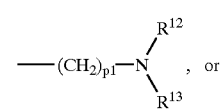, or (2) $W^2$ is hydrogen; and $W^1$ is

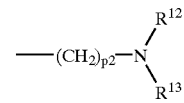

wherein p1 is an integer of 2 to 7; p2 is an integer of 3 to 7; and $R^{12}$ and $R^{13}$ are independently optionally substituted alkyl.

[13] An oxindole derivative or a prodrug thereof, or a pharmaceutically acceptable salt thereof according to [11] or [12] wherein $R^{12}$ and $R^{13}$ are independently methyl or ethyl.

[14] An optical isomer of an oxindole derivative according to any one of [1] to [13], of which the configuration at the C-3 position is equivalent to that of (+)-1-diethylaminoethyl-4-trifluoromethyl-6-carbamoyl-3-hydroxy-3-(2-chlorophenyl)oxindole, or a prodrug thereof, or a pharmaceutically acceptable salt thereof.

[15] A medicament containing an oxindole derivative or a prodrug thereof, or a pharmaceutically acceptable salt thereof according to any one of [1] to [14] and a pharmaceutically acceptable carrier or diluent.

[16] A medicament according to [15] wherein the medicament is growth hormone releaser.

[17] An oxindole derivative or a prodrug thereof, or a pharmaceutically acceptable salt thereof according to any one of [1] to [14] for use in therapy.

[18] Use of an oxindole derivative or a prodrug thereof, or a pharmaceutically acceptable salt thereof according to any one of [1] to [14] for the production of growth hormone releaser.

[19] Method of releasing growth hormone comprising administering an oxindole derivative or a prodrug thereof, or a pharmaceutically acceptable salt thereof according to any one of [1] to [14] to a human or a non-human mammal in need thereof.

"Alkyl" includes straight or branched $C_1$–$C_6$ alkyl. Typical examples are methyl, ethyl, propyl, 1-methylethyl, butyl, 1-methylpropyl, 2-methylpropyl, pentyl, 1-methylbutyl, 2-methylbutyl, 1-ethylpropyl, hexyl, 1-methylpentyl, 2-methylpentyl, 1-ethylbutyl and the like. The alkyls in "alkylthio", "alkylsulfinyl", "alkylsulfonyl" and "alkylsulfonylamino" include the same.

"Alkenyl" includes straight or branched $C_2$–$C_6$ alkenyl. Typical examples are vinyl, 1-propenyl, 2-propenyl, 1-butenyl, 2-butenyl, 3-butenyl, 3-pentenyl and the like.

"Alkynyl" includes straight or branched $C_2$–$C_6$ alkynyl. Typical examples are ethynyl, 1-propynyl, 2-propynyl, 3-butynyl, 2-pentynyl and the like.

"Alkoxy" includes straight or branched $C_1$–$C_6$ alkoxy. Typical examples are methoxy, ethoxy, propoxy, 1-methylethoxy, butoxy, 1-methylpropoxy, 2-methylpropoxy, pentoxy, 1-methylbutoxy, 2-methylbutoxy, 1-ethylpropoxy, hexoxy, 1-methylpentoxy, 2-methylpentoxy, 1-ethylbutoxy and the like. The alkoxy in "alkoxycarbonyl" includes the same.

"Alkanoyl" includes straight or branched $C_1$–$C_6$ alkanoyl. Typical examples are formyl, acetyl, propanoyl, butanoyl and the like. The alkanoyl in "alkanoylamino" include the same.

"$C_1$–$C_5$ alkylene" includes straight or branched $C_1$–$C_5$ alkylene. Typical examples are methylene, ethylene, propylene, trimethylene, tetramethylene, 1-methyltrimethylene, 2-methyltrimethylene, pentamethylene, 1-methyltetramethylene, 2-methyltetramethylene and the like. "$C_1$–$C_3$ alkylene" in Y includes straight or branched $C_1$–$C_3$ alkylene. Typical examples are methylene, ethylene and trimethylene, preferably methylene and ethylene.

The substituents of "substituted alkyl" include halogen, optionally substituted amino, alkoxy, alkoxycarbonyl, aryl, hydroxy, carboxy, optionally substituted carbamoyl, alkanoyl, arylcarbonyl, heteroarylcarbonyl, saturated heterocyclic group-carbonyl, alkanoylamino, alkylsulfonylamino, optionally substituted ureido, alkoxycarbonylamino, optionally substituted saturated heterocyclic group, optionally substituted sulfamoyl and the like.

Preferred examples of substituted alkyl in $R^1$, $R^2$, $R^3$ and $R^4$ are alkyls substituted by halogen(s) such as trifluoromethyl, pentafluoroethyl, 2-chloroethyl and the like.

The substituents of "substituted alkenyl" and "substituted alkynyl" include halogen, optionally substituted amino, alkoxy, alkoxycarbonyl, aryl, hydroxy, carboxy, optionally substituted carbamoyl, alkanoyl, arylcarbonyl, heteroarylcarbonyl, saturated heterocyclic group-carbonyl, alkanoylamino, alkylsulfonylamino, optionally substituted ureido, alkoxycarbonylamino, optionally substituted saturated heterocyclic group, optionally substituted sulfamoyl and the like.

Preferred examples of substituted alkynyl in $R^1$, $R^2$, $R^3$ and $R^4$ are $C_3$–$C_6$ 1-alkynyl substituted by polar substituent(s) such as hydroxy, alkylsulfonylamino, alkanoylamino, alkylureido, oxo-saturated heterocyclic group (e.g. 2-oxo-1-imidazolodinyl, 2-oxo-1,3-oxazolin-3-yl), optionally substituted carbamoyl and the like. The examples include 4-carbamoyl-1-butynyl, 4-alkylcarbamoyl-1-butynyl, 4-dialkylcarbamoyl-1-butynyl, 4-morpholinocarbonyl-1-butynyl, —C≡C—$(CH_2)_k$—Q, wherein k and Q are as defined above "Aryl" includes $C_6$–$C_{10}$ aryl. Typical examples are phenyl, 1-naphthyl, 2-naphthyl and the like. The aryl in "arylcarbonyl" includes is the same.

"Heteroaryl" includes 5- to 7-membered mono- or bi-cyclic heteroaryl containing 1 to 3 atoms of nitrogen, sulfur and/or oxygen atoms. Typical examples include 5- to 7-membered mono-cyclic heteroaryl containing 1 to 3 atoms of nitrogen, sulfur and/or oxygen atoms such as pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, isothiazolyl, triazinyl, triazolyl, imidazolidinyl, oxadiazolyl, triazolyl, triazinyl, tetrazolyl and the like; 5- to 7-membered bi-cyclic heteroaryl containing 1 to 3 atoms of nitrogen, sulfur and/or oxygen atoms such as indolyl, chromenyl, quinolyl, isoquinolyl, benzofuranyl, benzothienyl, benzoxazolyl, benzothiazolyl, benzisoxazolyl, benzisothiazolyl, benzotriazolyl, benzimidazolyl and the like; and the like. The heteroaryl in "heteroarylcarbonyl" includes the same.

"Cycloalkyl" includes $C_3$–$C_8$ cycloalkyl. Typical examples are cyclopropyl, cyclobutyl, cyclopentyl, cyclohexyl, cycloheptyl, cyclooctyl and the like.

"Cycloalkane" includes $C_3$–$C_8$ cycloalkane. Typical examples are cyclopropane, cyclobutane, cyclopentane, cyclohexane, cycloheptane, cyclooctane and the like.

"Saturated heterocyclic ring" includes 5- to 7-membered mono-cyclic saturated heterocyclic rings containing 1 to 3 atoms of nitrogen, sulfur and/or oxygen atoms. Typical examples include 5-membered mono-cyclic saturated heterocyclic rings containing 1 to 3 atoms of nitrogen, sulfur and/or oxygen atoms such as tetrahydrofuran, pyrrolidine, pyrazoline, thiazolidine, oxazolidine and the like; 6-membered mono-cyclic saturated heterocyclic rings containing 1 to 3 atoms of nitrogen, sulfur and/or oxygen atoms such as piperidine, morpholine, thiamorpholine, piperazine and the like; 7-membered mono-cyclic saturated heterocyclic rings containing 1 to 3 atoms of nitrogen, sulfur and/or oxygen atoms such as perhydroazepine and the like; and the like.

"Saturated heterocyclic group" is a radical formed by removing hydrogen from saturated heterocyclic ring. The saturated heterocyclic group in "saturated heterocyclic group-carbonyl" includes the same.

The substituent of "substituted aryl", "substituted phenyl", "substituted 2-naphthyl", "substituted heteroaryl", "substituted cycloalkyl", "substituted cycloalkane", "substituted saturated heterocyclic ring" and "substituted saturated heterocyclic group" include halogen, aryl, heteroaryl, optionally substituted alkyl, alkenyl, alkynyl, optionally substituted amino, cyano, nitro, hydroxy, mercapto, alkoxy, alkanoyl, alkoxycarbonyl, carboxy, optionally substituted sulfamoyl, optionally substituted carbamoyl, alkylsulfamoylamino, alkylsulfinyl, alkylsulfonyl, alkylsulfonylamino, alkanoylamino and the like. The substituent of "substituted saturated heterocyclic ring" and "substituted saturated heterocyclicric group" also includes oxo. Examples of the "oxo-saturated heterocyclic ring" and "oxo-saturated heterocyclic group" include oxo-5-membered saturated heterocyclic rings or groups such as pyrrolidinone(yl), thiazolidinone(yl), 2-oxo-1,3-oxazoline (yl), 2-oxo-imidazolidine(yl) and the like; oxo-6-membered saturated heterocyclic rings or groups such as piperidinone (yl) and the like.

Preferred examples of substituents of "substituted aryl" and "substituted heteroaryl" in $R^5$ are halogen, alkoxy, alkyl substituted by halogen(s) and the like, especially chlorine, fluorine, methoxy, trifluoromethyl and the like.

"Halogen" includes fluorine, chlorine, bromine and iodine.

The substituent of "substituted amino" includes alkyl optionally substituted by hydroxy or alkoxy, and the like. Amino may be substituted by two substituents.

The substituent of "substituted sulfamoyl", "substituted carbamoyl" and "substituted ureido" includes alkyl optionally substituted by hydroxy or alkoxy, and the like. Sulfamoyl, carbamoyl and ureido may be substituted by two substituents. When sulfamoyl, carbamoyl or ureido is substituted by two substituents, the two substituents may be taken together with adjacent nitrogen atom to form saturated heterocyclic ring such as morpholine and the like.

"Prodrug" includes prodrugs described in Chemistry and Industry, 1980, 435; Advanced Drug Discovery Reviews 3, 39(1989). The typical examples are biohydrolyzable esters such as acyloxymethyl esters, glycolates, lactates and morpholinoethyl ester of carboxyl group; hemiglutarates of phenolic hydroxyl group; N-morpholinomethyl amides; N-acyloxymethyl amines; N-ayloxyalkoxycarbonylamines.

The oxindole derivative or a prodrug thereof may be in the form of pure optical isomer, partially purified optical isomer, racemate, mixture of diastereomers or the like. Preferred optical isomers of the oxindole derivatives are the optical isomers, of which the configurations at the 3rd position are equivalent to that of (+)-1-diethylaminoethyl-4-trifluoromethyl-6-carbamoyl-3-hydroxy-3-(2-chlorophenyl) oxindole. The optical isomers are usually distinguishable from their retention times in HPLC on a Chiralpak OD™ with isopropanol/hexane as the eluent. The referred optical isomer is usually eluted later than its enantiomer.

Pharmaceutically acceptable salts of the oxindole derivatives or a prodrug thereof include salts with inorganic acids and salts with organic acids. Typical examples of the salts with inorganic acids are the hydrochloride, hydrobromide, nitrate, sulfate, phosphate salts and the like. Typical examples of the salts with organic acids are the formate, acetate, trifluoroacetate, propionate, lactate, tartrate, oxalate, fumarate, maleate, citrate, malonate, methanesulfonate, benzenesulfonate salts and the like. In case that the oxindole derivatives have acidic group(s) such as carboxyl and the like, salts thereof with bases may be formed. The salts include salts with organic bases such as the arginine, lysine, triethylammonium salts and the like; salts with inorganic bases such as the alkaline metal (sodium, potassium, etc.), alkaline earth metal (calcium, barium, etc.), ammonium salts and the like. The oxindole derivative or pharmaceutically acceptable salt thereof may be in the form of a solvate such as a hydrate and the like. The oxindole derivative of Formula 1 can be produced for example by the following methods.

Method A

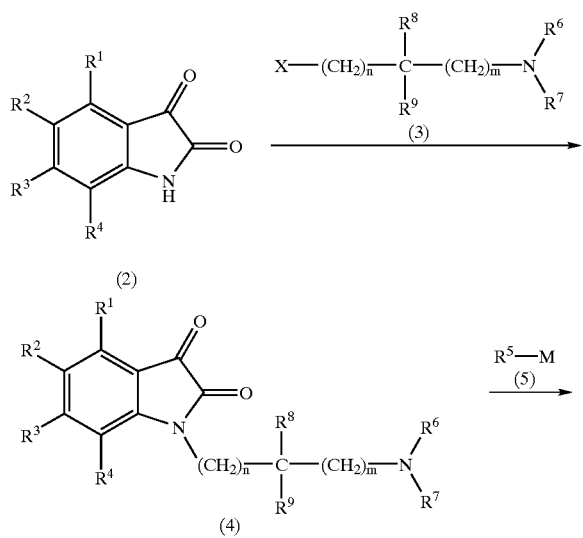

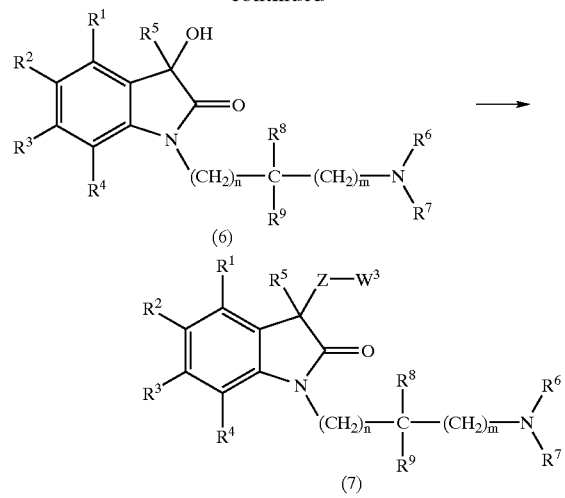

wherein $R^1$, $R^2$, $R^3$, $R^4$, $R^5$, $R^6$, $R^7$, $R^8$, $R^9$, Z, n and m are as defined above. X is chlorine, bromine, iodine, methanesulfoxy or toluenesulfoxy; M is lithium, magnesium bromide, magnesium iodide or magnesium chloride; $W^3$ is hydrogen, alkyl or $—Y—CON(R^{10})R^{11}$ wherein $R^{10}$ and $R^{11}$ are as defined above.

Compound (4) is produced by reacting isatin derivative (2) with compound (3) in the presence of a base. The reaction can be carried out according to conventional conditions of N-alkylation reaction. The base includes an alkaline hydride such as sodium hydride, potassium hydride and the like; alkaline amide such as sodium amide, lithium amide and the like; alkaline alkoxide such as potassium t-butoxide, sodium methoxide and the like; and the like. The amount of the base is usually 1 to 10 equivalents, preferably 1.5 to 5 equivalents, per equivalent of the isatin derivative (2). When a salt of compound (3) such as the hydrochloride and the like is used, the corresponding equivalents of the base may be added in surplus. The amount of compound (3) is usually 1 to 3 equivalents, preferably 1.2 to 2 equivalents, per equivalent of the isatin derivative (2). The reaction solvent includes an inert organic solvent such as tetrahydrofuran (THF), N,N-dimethylformamide (DMF) and the like. The reaction temperature may be in the range of 0° C. to the boiling point of the solvent, preferably in the range of room temperature to 80° C.

Compound (6) is produced by reacting compound (4) with compound (5). The reaction of compound (4) with compound (5) can be carried out by conventional methods. The amount of compound (5) is usually 1 to 2 equivalents per equivalent of compound (4). The reaction solvent includes ethers such as diethyl ether, THF and the like. The reaction temperature may be in the range of −78° C. to room temperature.

The hydroxy group of compound (6) may be converted to an amino group, if needed. Chlorination of compound (6) with thionyl chloride, followed by azidation and reduction affords the corresponding amine. The chlorination is usually carried out without solvents at the temperature between room temperature and 50° C. The azidation is for example performed using alkaline azide such as sodium azide in the presence of a base such as triethylamine in an inert solvent such as THF and DMF at the temperature between room temperature and 80° C. The reducing agent includes tin chloride. The reaction solvent includes alcohols such as methanol and ethanol. The reaction temperature may be in the range of room temperature to the boiling point of the solvent.

Oxindole derivative (7) can be produced by introducing alkyl or —Y—CON($R^{10}$)$R^{11}$ wherein $R^{10}$ and $R^{11}$ are as defined above to compound (6) or the corresponding amine, if needed. Introduction of alkyl or —Y—CON($R^{10}$)$R^{11}$ can be carried out by conventional methods, for example, reaction with alkyl halide, $X^1$—Y—CON($R^{10}$)$R^{11}$ wherein $R^{10}$ and $R^{11}$ are as defined above; $X^1$ is chlorine, bromine, iodine, methanesulfonyl or toluenesulfonyl, or $R^{10}$—NCO wherein $R^{10}$ is as defined above, in the presence or absence of a base. The base includes an alkaline hydride such as sodium hydride, potassium hydride and the like; an alkaline amide such as sodium amide, lithium amide and the like; organic base such as triethylamine, ethyldiisopropylamine and the like. The amount of the base is usually 1 to 10 equivalents per equivalent of compound (6) or the corresponding amine. The amount of the alkyl halide, $X^1$—Y—CON($R^{10}$)$R^{11}$ or $R^{10}$—NCO is usually 1 to 10 equivalents per equivalent of compound (6) or the corresponding amine. The reaction solvent includes inert solvents such as THF, DMF and the like. The reaction temperature may be in the range of 0° C. to the boiling point of the solvent, preferably in the range of room temperature to 80° C.

Method B

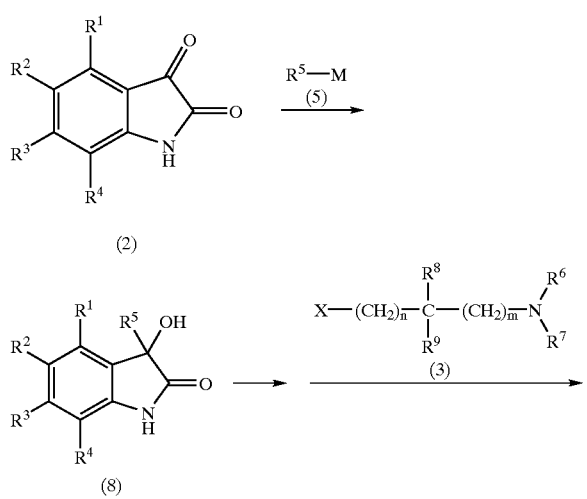

wherein $R^1$, $R^2$, $R^3$, $R^4$, $R^5$, $R^6$, $R^7$, $R^8$, $R^9$, n, m, X, M and $W^3$ are as defined above.

Compound (8) is produced by reacting isatin derivative (2) and compound (5) by the same method as that in the reaction of compound (4) with compound (5). The hydroxyl group of compound (8) may be converted to an amino group by the same method as that in conversion of hydroxyl group of compound (6). Then, oxindole derivatives (7) and (9) can be produced by reacting compound (8) with compound (3) by the same method as that in the reaction of isatin derivative (2) with compound (3), followed by introduction of alkyl or —Y—CON($R^{10}$)$R^{11}$ wherein $R^{10}$ and $R^{11}$ are as define above, if needed. This reaction normally produces the oxindole derivative (9) mainly.

Isatin derivative (2) can be prepared for example as below.

Method for Preparing Isatin Derivatives (Method C)

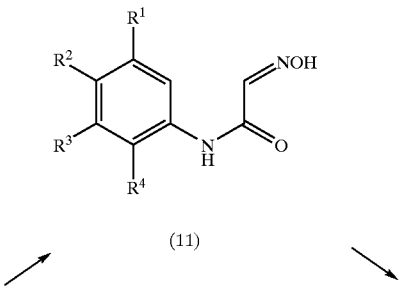

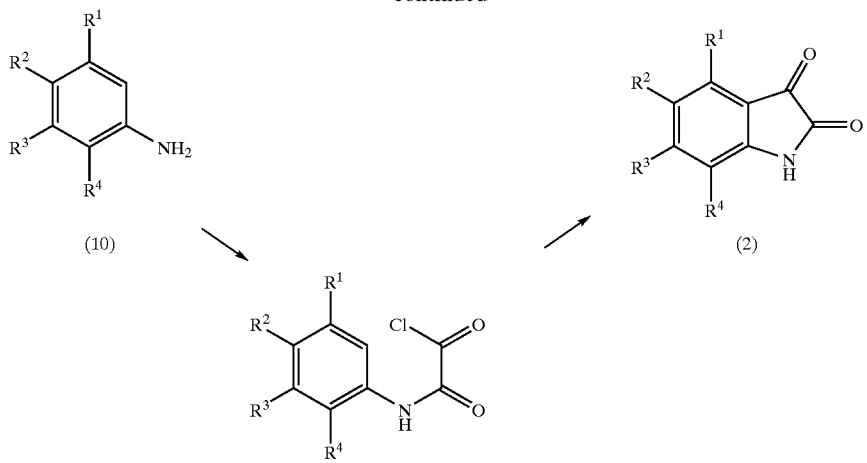

wherein $R^1$, $R^1$, $R^3$ and $R^4$ are as defined above.

Isatin derivative (2) can be prepared according to Sandmeyer's method (Org. Synth., Coll. Vol. I, 321(1941)). Isatin derivative (2) is prepared by reacting aniline derivative (10) with chloral hydrate and hydroxylamine in water under reflux to give compound (11), followed by treating the compound with acid and then with water. The acid includes conc. sulfuric acid, polyphosphoric acid and the like. The acid may be used as a solvent preferably. The temperature in the treatment with acid may be in the range of 50 to 100° C. The treatment with water is performed by adding the reaction mixture into water. The temperature of the treatment with water is preferably in the range of 0° C. to room temperature. Ice may be used in place of the water, because the treatment makes a lot of heat.

Isatin derivative (2) is prepared by reacting Aniline derivative (10) with oxalyl chloride, followed by intramolucular Friedel-Crafts reaction. These two reactions may also be done all at once in the same vessel. The reaction solvent includes halogenated solvents such as methylene chloride, 1,2-dichloroethane and the like. The reaction may be carried out without solvents. In the Friedel-Craft's reaction, Lewis acid may be added. The Lewis acid includes aluminum chloride and the like.

Method for Preparing Isatin Derivative (Method D)

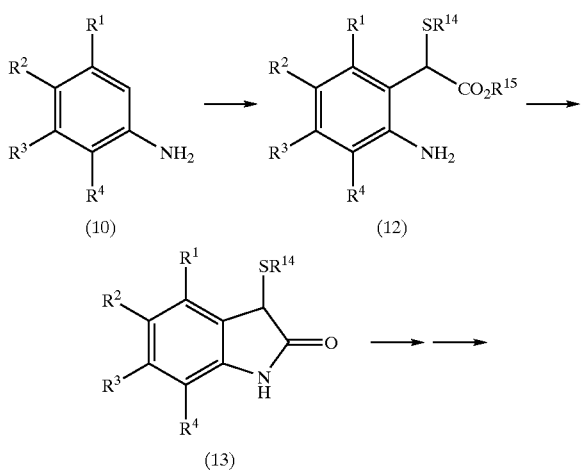

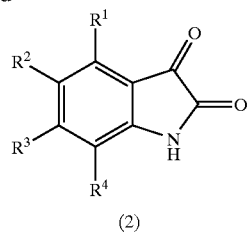

wherein $R^1$, $R^2$, $R^3$ and $R^4$ are as defined above; $R^{14}$ and $R^{15}$ are independently alkyl.

Isatin derivative (2) can be prepared according to Gassman's method (J. Am. Chem. Soc., 96, 5508(1974)). Compound (12) is prepared by chlorination of aniline derivative (10) followed by adding compound: $R^{14}SCH_2CO_2R^{15}$ and then a base. The reaction solvent includes halogenated solvents such as methylene chloride, 1,2-dichloroethane and the like. The chlorination agent includes sulfuryl chloride, t-butoxy chloride and the like. The temperature of the chlorination and the addition of compound: $R^{14}SCH_2CO_2R^{15}$ may be in the range of –20 to –78° C. The base includes organic bases such as triethylamine and the like. The addition of a base may be carried out by warming the reaction mixture to room temperature and keeping the mixture at the temperature.

Compound (13) is produced by treating compound (12) with an acid. The acid includes hydrochloric acid, sulfuric acid, methanesulfonic acid and the like. The reaction temperature may be room temperature. This reaction may be carried out in the same vessel of the previous reaction successively.

Compound (2) is produced by oxidation of compound (13). The oxidizing agent includes copper(II) oxide and the like. The reaction temperature may be in the range of room temperature to the boiling temperature of the solvent. The reaction solvent includes an inert organic solvent such as acetone, acetonitrile and the like.

Method for Preparing Isatin Derivative (Method E)

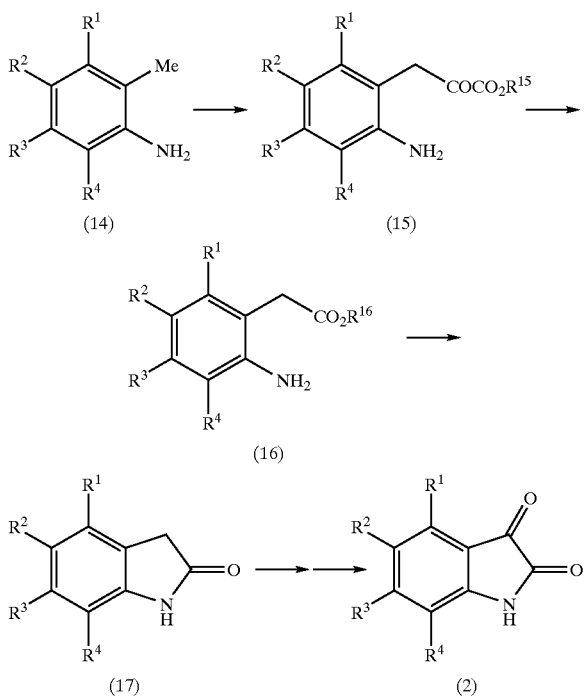

wherein $R^1$, $R^2$, $R^3$ and $R^4$ are as defined above; $R^{15}$ and $R^{16}$ are independently alkyl.

Isatin derivative (2) can be prepared by Reisert reaction. For example, Reisert reaction of nitrotoluene (14) with dialkyl oxalate in the presence of metal alkoxide in an alcoholic solvent provides ketoester (15) (J. Am. Chem. Soc., 78, 221 (1956)). Suitable combinations of the dialkyl oxalate, metal alkoxide and alcoholic solvent are dimethyl oxalate-sodium methoxide-methanol, dimethyl oxalate-potasium methoxide-methanol and diethyl oxalate-sodium ethoxide-ethanol. Treating ketoester (15) with aqueous hydrogen peroxide in the presence of acid such as perchloric acid (J. Org. Chem., 16, 1785 (1951)) followed by methylation using methanol-hydrogen chloride or thionyl chloride affords ester (16). Reduction of the nitro group with Fe-acetic acid, aqueous titanium trichloride or tin(II) chloride forms oxindole (17) (Synthesis, 1993, 51). Two steps conversion of oxindole (17) into isatin (2) are effected by treating pyridinium tribromide followed by hydrolysis using acid such as hydrogen bromide (Tetrahedron Lett., 39, 7679 (1998)).

In the above reactions, functional groups in each compound may be protected if needed. The protective groups include the well known protective groups (Protective Groups in Organic Synthesis, T. W. Greene, A Wiley-Interscience Publication (1981) etc.) and the like.

Oxindole derivative (1) produced according to the above methods may be mixture of isomers. In that case, each isomer can be isolated by a suitable method such as silica chromatography and the like at the final stage or an intermediate stage.

Optical isomers of oxindole derivative (1) may be obtained by conventional optical resolution methods such as recrystallization of salts thereof with an optical acid such as tartaric acid and the like.

Prodrug of the oxindole derivative (1) may be obtained by conventional methods (as described in Chemistry and Industry, 1980, 435; Advanced Drug Discovery Reviews 3, 39(1989)).

The pharmaceutically acceptable salt of the oxindole derivative (1) or a prodrug thereof can be formed by mixing the oxindole derivative (1) or a prodrug thereof with a pharmaceutically acceptable acid such as hydrogen chloride, citric acid, methanesulfonic acid and the like in a solvent such as water, methanol, ethanol, acetone and the like.

Specifically preferred examples of the oxindole derivatives are:

1-(2-Diethylaminoethyl)-4-trifluoromethyl-6-carbamoyl-3-hydroxy-3-(2-chloro-3-pyridyl)oxindole, 1-(2-Diethylaminoethyl)-4-trifluoromethyl-6-carbamoyl-3-hydroxy-3-(2-chloro-3-thienyl)oxindole, 1-(2-Diethylaminoethyl)-4-trifluoromethyl-6-carbamoyl-3-hydroxy-3-(5-indolyl)oxindole, 1-(2-Diethylaminoethyl)-4-trifluoromethyl-6-[3-(3-methyl-2-oxo-1-imidazolidinyl)-1-propynyl]-3-hydroxy-3-(2-chlorophenyl)oxindole, 1-(2-Diethylaminoethyl)-4-trifluoromethyl-6-[4-(3-methyl-2-oxo-1-imidazolidinyl)-1-butynyl]-3-hydroxy-3-(2-chlorophenyl)oxindole, 1-(2-Diethylaminoethyl)-4-trifluoromethyl-6-[4-dimethylcarbamoyl-1-butynyl]-3-hydroxy-3-(2-chlorophenyl)oxindole, 1-(2-Diethylaminoethyl)-4-trifluoromethyl-6-[5-dimethylcarbamoyl-1-pentynyl]-3-hydroxy-3-(2-chlorophenyl)oxindole, 1-(2-Diethylaminoethyl)-4-trifluoromethyl-6-dimethylcarbamoylethynyl-3-hydroxy-3-(2-chlorophenyl)oxindole, 1-(2-Diethylaminoethyl)-4-trifluoromethyl-6-carbamoylethynyl-3-hydroxy-3-(2-chloro-4-bromophenyl)oxindole, 1-(2-Diethylaminoethyl)-4-trifluoromethyl-6-(2-carbamoylethenyl)-3-hydroxy-3-(2-chloro-4-bromophenyl)oxindole, 1-(2-Diethylaminoethyl)-4-trifluoromethyl-6-(2-carbamoylethyl)-3-hydroxy-3-(2-chloro-4-bromophenyl)oxindole, 1-(2-Diethylaminoethyl)-4-trifluoromethyl-6-(4-amino-1-butynyl)-3-hydroxy-3-(2-chlorophenyl)oxindole, 1-(2-Diethylaminoethyl)-4-trifluoromethyl-6-(4-acetamino-1-butynyl)-3-hydroxy-3-(2-chlorophenyl)oxindole, 1-(2-Diethylaminoethyl)-4-trifluoromethyl-6-(5-carboxy-1-pentynyl)-3-hydroxy-3-(2-chlorophenyl)oxindole, 1-(2-Diethylaminoethyl)-4-trifluoromethyl-6-sulfamoyl-3-hydroxy-3-(2-chlorophenyl)oxindole, 1-(2-Diethylaminoethyl)-4-trifluoromethyl-6-methylsulfamoyl-3-hydroxy-3-(2-chlorophenyl)oxindole, 1-(2-Diethylaminoethyl)-4-trifluoromethyl-6-dimethylsulfamoyl-3-hydroxy-3-(2-chlorophenyl)oxindole, 1-(2-Diethylaminoethyl)-4-trifluoromethyl-6-(4-sulfamoyl-1-butynyl)-3-hydroxy-3-(2-chlorophenyl)oxindole, 1-(2-Diethylaminoethyl)-4-trifluoromethyl-6-carbamoyl-3-hydroxy-3-(1-naphthyl)oxindole, 1-(2-Diethylaminoethyl)-4-trifluoromethyl-7-carbamoyl-3-hydroxy-3-(2-chlorophenyl)oxindole, 1-(2-Diethylaminoethyl)-6-carbanoyl-3-hydroxy-3-(2-chlorophenyl)oxindole, 1-(2-Diethylaminoethyl)-4-methyl-6-carbamoyl-3-hydroxy-3-(2-chlorophenyl)oxindole, 1-(2-Diethylaminoethyl)-4-methoxy-6-carbamoyl-3-hydroxy-3-(2-chlorophenyl)oxindole, 1-(2-Diethylaminoethyl)-4-fluoro-6-carbamoyl-3-hydroxy-3-(2-chlorophenyl)oxindole, 1-(2-Diethylaminoethyl)-4-cyano-6-carbamoyl-3-hydroxy-3-(2-chlorophenyl)oxindole, 1-(2-Diethylaminoethyl)-4-hydroxy-6-carbamoyl-3-hydroxy-3-(2-chlorophenyl)oxindole, 1-(2-Diethylaminoethyl)-5-trifluoromethyl-6-carbamoyl-3-hydroxy-3-(2-chlorophenyl)oxindole, 1-(2-Diethylaminoethyl)-5-chloro-6-carbamoyl-3-hydroxy-3-(2-chlorophenyl)oxindole, 1-(2-Diethylaminoethyl)-4-trifluoromethyl-5-chloro-6-carbamoyl-3-hydroxy-3-(2-chlorophenyl)oxindole, 1-(2-(2-Piperidinyl)ethyl-4-trifluoromethyl-6-carbamoyl-3-hydroxy-3-(2-chlorophenyl)oxindole, 1-(2-(2-Pyrrolidinyl)ethyl)-4-trifluoromethyl-6-carbamoyl-3-hydroxy-3-(2-chlorophenyl)oxindole, 1-(2-(N-methyl-2-pyrrolidinyl)ethyl)-4-trifluoromethyl-6-carbamoyl-3-hydroxy-3-(2-chlorophenyl)oxindole, 1-(2-Piperidinylmethyl)-4-trifluoromethyl-6-carbamoyl-3-hydroxy-3-(2-chlorophenyl)oxindole, 1-(3-Amino-3-methylbutyl)-4-trifluoromethyl-6-carbamoyl-3-hydroxy-3-(2-chlorophenyl)oxindole, 1-(3-Aminobutyl)-4-trifluoromethyl-6-carbamoyl-3-hydroxy-3-(2-chlorophenyl)oxindole, 1-(4-Dimethylamino-3,3-dimethylbutyl)-4-trifluoromethyl-6-carbamoyl-3-hydroxy-3-(2-chlorophenyl)oxindole, 1-(2-Diethylaminoethyl)-4-trifluoromethyl-6-carbamoyl-3-hydroxy-3-(2,3-dichlorophenyl)oxindole, 1-(2-Diethylaminoethyl)-4-trifluoromethyl-6-carbamoyl-3-hydroxy-3-(2-chloro-4-methoxyphenyl)oxindole, 1-(2-Diethylaminoethyl)-4-trifluoromethyl-6-carbamoyl-3-hydroxy-3-(2-chloro-4-bromophenyl)oxindole, and 1-(2-Diethylaminoethyl)-4-trifluoromethyl-6-carbamoyl-3-hydroxy-3-(2,3,4-trichlorophenyl)oxindole.

The oxindole derivatives of the present invention have effects and usage similar to those of growth hormone, because the oxindole derivatives can stimulate the release of growth hormone from the pituitary. Examples of the growth hormone's effects and usage are as follows:

stimulation of growth hormone release in the elderly; treating growth hormone deficient adults; prevention of catabolic side effects of glucocorticoids; prevention and treatment of osteoporosis; stimulation of the immune system; acceleration of wound healing; accelerating bone fracture repair; treatment of growth retardation; treating acute or chronic renal failure or insufficiency; treatment of physiological short stature including growth hormone deficient children and short stature associated with chronic illness; treatment of obesity and growth retardation associated with obesity; treating growth retardation associated with the Prader-Willi syndrome and Turner's syndrome; accelerating the recovery and reducing hospitalization of burn patients or following major surgery such as gastrointestinal surgery; treatment of intrauterine growth retardation, skeletal dysplasia, hypercortisolism and Cushing's syndrome; induction of pulsatile growth hormone release; replacement of growth hormone in stressed patients; treatment of osteochondrodysplasias, Noonan's syndrome, schizophrenia, depressions, Alzheimer's disease, delayed wound healing and psychosocial deprivation; treatment of pulmonary dysfunction and ventilator dependency; attenuation of protein catabolic responses after major surgery; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development; prevention of the age-related decline of thymic function; adjunctive therapy for patients on chronic hemodialysis; treatment of immunosuppressed patients; enhancing antibody response following vaccination; improvement in muscle strength and mobility in the frail elderly; maintenance of skin thickness, metabolic homeostasis, renal homeostasis in the frail o elderly; stimulation of osteoblasts, bone remodelling and cartilage growth in the frail elderly; treatment of neurological diseases such as peripheral and drug induced neuropathy, Guillian-Barre Syndrome, amyotrophic lateral sclerosis, multiple sclerosis, cerebrovascular accidents and demyelinating diseases; stimulation of the immune system in companion animals; treatment of disorders of aging in companion animals; growth promotion in livestock; stimulation of wool growth in sheep; and the like.

In particular, the oxindole derivatives are useful for treating medical disorders resulting from a deficiency in growth hormone.

The oxindole derivatives of the present invention may be applicable to not only humans but also various non-human mammals such as mice, rats, dogs, cows, horses, goats, sheep, rabbits, pigs and the like.

The oxindole derivative of the present inventionmay be administered orally or parenterally (intramuscularly, intravenously, subcutaneously, percutaneously, intranasally, by suppository, by eye drops, by injection into brain). Pharmaceutical forms include generally acceptable forms, for example, powders, granules, fine granules, tablets, capsules, pills, syrups, suspensions, injections such as solutions, emulsions, suppository for administration through the rectum, dermal preparations (ointments, creams, lotions etc.) and the like.

These compositions can be prepared by the conventional methods using conventional carriers or diluents. The solid compositions such as tablets can be prepared by mixing the active compound with pharmaceutically acceptable conventional carriers or excipients such as lactose, sucrose, corn starch or the like; binders such as hydroxypropylcellulose, polyvinylpyrrolidone, hydroxypropylmethylcellulose or the like; disintegrating agents such as sodium carboxymethylcellulose, sodium starch glycolate or the like; lubricants such as stearic acid, magnesium stearate or the like; or preservatives or the like. For parenteral administration such as solutions and suspensions, the active compound can be dissolved or suspended in a physiologically acceptable carrier or diluent such as water, saline, oil, dextrose solution or the like, which may contain auxiliary agents such as pH adjusters, buffers, stabilizers, solubilizers, emulsifiers, salts for influencing osmotic pressure and the like, if desired.

The dose and the frequency for administration of the oxindole derivative or a prodrug thereof, or a pharmaceutically acceptable salt thereof generally varies depending on the species to be cured, the administration route, the severity of the symptoms, the body weight and the like. The oxindole derivative, a prodrug thereof and a pharmaceutically acceptable salt thereof are usually administered to an adult (body weight: 60 kg) in a dose of about 1 mg to about 1 g, preferably about 1 mg to about 200 mg, more preferably about 5 mg to about 50 mg per day in one portion or several portions. They may be also administered once in 2 days to 1 week. No toxic effects were obserbed at therapeutic doses.

EXAMPLES

The present invention will be described in detail below, referring to reference examples and examples, which are not limitative of the present invention.

Reference Example 1

4,6-Dichloroisatin

To a solution of trichloroacetaldehyde monohydate (13.25 g, 1.3 eq) in $H_2O$ (150 mL) was successively added sodium sulfate (17.55 g, 4.0 eq), a hot solution (ca. 80° C.) of 3,5-dichloroaniline (10.0 g, 61.5 mmol) in $H_2O$ (50 mL) and 37% HCl (6.1 mL), and a solution of hydroxylamine hydrochloride (16.3 g, 3.8 eq) in $H_2O$ (75 mL) with rapid stirring. Once the addition was completed the reaction mixture was heated at reflux for 2 minutes and then allowed to cool to room temperature. The resulting light brown precipitate was filtered, washed with $H_2O$ (200 mL) and then dried to yield the crude isonitrosoacetanilide (20.13 g).

The above product (20.13 g) was added portion wise to rapidly stirred conc. sulfuric acid (72 mL) at such a rate so as to keep the reaction temperature from 50° C. to 70° C. The resulting solution was stirred at 80° C. for 10 minutes after which the mixture was allowed to cool to room temperature. The cooled mixture was poured carefully onto ice (ca. 300 g). The ice mixture was allowed to stand for 1 hour. The orange precipitate formed was filtered, washed with $H_2O$ (300 mL) and then dried to yield 4,6-dichloroisatin.

$^1$H NMR (DMSO-$d_6$, 270 MHz) δ 11.34 (brs, 1H), 7.25 (d, J=1.6 Hz, 1H), 6.89 (d, J=1.6 Hz, 1H).

Reference Example 2

Mixture of 4-Bromoisatin and 6-Bromoisatin

This mixture (2.5:1) was prepared by the same method as that described in reference example 1, using 3-bromoaniline in place of 3,5-dicloroaniline.
4-Bromoisatin:
$^1$H NMR (CDCl$_3$, 270 MHz) δ 11.17 (brs, 1H), 7.46 (dd, J=8.0, 8.0 Hz, 1H), 7.22 (dd, J=0.7, 8.0 Hz, 1H), 6.89 (dd, J=0.7, 8.0 Hz, 1H).
6-Bromoisatin:
$^1$H NMR (CDCl$_3$, 270 MHz) δ 11.10 (brs, 1H), 7.47 (d, J=7.9 Hz, 1H), 7.26 (dd, J=1.7 and 7.9 Hz, 1H), 7.08 (d, J=1.7 Hz, 1H).

Reference Example 3

7-Bromoisatin

This compound was prepared by the same method as that described in reference example 1, using 2-bromoaniline in place of 3,5-dicloroaniline.
$^1$H NMR (CDCl$_3$, 270 MHz) δ 7.94 (brs, 1H), 7.71 (d, J=7.9 Hz, 1H), 7.59 (d, J=7.9 Hz, 1H), 7.06 (dd, J=7.9 and 7.9 Hz, 1H).

Reference Example 4

4,6-Dimethylisatin

This compound was prepared by the same method as that described in reference example 1, using 3,5-dimethylaniline in place of 3,5-dicloroaniline.
$^1$H NMR (CDCl$_3$, 270 MHz) δ 7.72 (brs, 1H), 6.69 (s, 1H), 6.51 (s, 1H), 2.53 (s, 3H), 2.36 (s, 3H).

Reference Example 5

Mixture of 4-iodo-6-Chloroisatin and 4-Chloro-6-iodoisatin

This mixture (2.4:1) was prepared by the same method as that described in reference example 1, using 3-chloro-5-iodoaniline (J. Med. Chem., 1991, 34, 1243) in place of 3,5-dicloroaniline.
4-iodo-6-Chloroisatin:
$^1$H NMR (DMSO-$d_6$, 270 MHz) δ 11.17 (brs, 1H), 7.57 (brm, 1H), 6.94 (brm, 1H).
4-Chloro-6-iodoisatin:
$^1$H NMR (DMSO-$d_6$, 270 MHz) δ 11.25 (brs, 1H), 7.53 (brm, 1H), 7.20 (brm, 1H).

Reference Example 6

4-Trifluoromethylisatin

To a solution of 3-trifluoroaniline (3.29 g, 10 mmol) in dichloromethane (100 mL) was added sulfuryl chloride (1.2 eq) at −78° C. The reaction solution was stirred for 30 minutes. To the mixture was then added ethyl methylthioacetate (1.2 eq) and stirring was continued for a further 2 hours, at −78° C. Triethylamine (7 mL) was added next. Then the mixture was allowed to warm to room temperature. To the mixture was added an excess amount of 1N HCl and the mixture stirred overnight. The organic phase was separated, dried over MgSO$_4$ and concentrated Purification was carried out by silica gel chromatography (3:1 hexane/ethyl acetate) to give 3-methylthio-4-trifluoromethyloxindole.

$^1$H NMR (CDCl$_3$, 270 MHz) δ 8.35 (brs, 1H), 7.50 (d, 1H), 7.38 (d, 1H), 7.14 (s, 1H), 4.32 (1H, s), 2.07 (s, 3H).

To a solution of 3-methylthio-4-trifluoromethyloxindole (1 mmol) in acetone (6 mL) was added copper (II) chloride (1.5 eq) and copper (II) oxide (1.5 eq). The mixture was stirred at room temperature for 3 hours. To the resulting mixture was added 1N HCl, followed by ethyl acetate.

The ethyl acetate phase was separated, washed further with 1N hydrochloric acid and brine, and then dried over anhydrous MgSO$_4$. After filtration, the solvent was evaporated to give 4-trifluoromethylisatin quantitatively.

$^1$H NMR (DMSO-$d_6$, 270 MHz) δ 8.61 (brs, 1H), 7.72 (m, 1H), 7.41 (m, 1H), 7.17 (d, 1H).

Reference Example 7

Mixture of 5-Bromo-4-chloroisatin and 5-Bromo-6-chloroisatin

The mixture of 4-chloroisatin and 6-chloroisatin (1:1) was prepared by the same method as that described in reference example 1, using 3-chloroaniline in place of 3,5-dicloroaniline.
4-Chloroisatin:
$^1$H NMR (DMSO-$d_6$) δ 11.2 (1H, s), 7.55 (1H, J=8 Hz, t), 7.06 (1H, J=0.5, 8.0 Hz, dd), 6.85 (1H, J=0.5, 8.0 Hz, dd).
6-Chloroisatin:
$^1$H NMR (DMSO-$d_6$) δ 11.2 (1H, s), 7.53 (1H, J=8.0 Hz, d), 7.11 (1H, J=2.0, 8.0 Hz, dd), 6.94 (1H, J=2.0 Hz, d).

The mixture of 4-chloroisatin and 6-chloroisatin (1:1, 1.03 g, 5.67 mmol) and N-bromosuccinimide (1.23 g, 6.91 mmol) were dissolved in DMF (10 mL) and the mixture was stirred at 60° C. for 3 hours and then cooled to room temperature. Saturated aqueous NaHCO$_3$ was added to the reaction mixture and the mixture was extracted with a mixture of toluene and ethyl acetate (1:1). The organic phase was washed with brine and dried over anhydrous MgSO$_4$ to give the title mixture (1:1).
5-Bromo-4-chloroisatin:
$^1$H NMR (DMSO-d$_6$, 270 MHz) δ 11.3 (1H, s), 7.90 (1H, J=8.5 Hz, d), 6.82 (1H, J=8.5 Hz, d).
5-Bromo-6-chloroisatin:
$^1$H NMR (DMSO-d$_6$, 270 MHz) δ 11.3 (1H, s), 7.88 (1H, s), 7.13 (1H, s).

Reference Example 8

1-(2-Diethylaminoethyl)-4,6-dichloroisatin

To the compound of reference example 1 (1.00 g, 4.63 mmol) in DMF (10 mL) was added 60% NaH (1.67 g, 10.2 mmol) with stirring, followed by 2-diethylaminoethyl chloride hydrochloride (876.4 mg, 5.09 mmol). The mixture was stirred at 60° C. for 9 hours after which the reaction mixture was cooled to room temperature. Water was then added and the mixture extracted with a mixture of toluene and ethyl acetate (1:1). The organic phase was washed with brine and then dried over MgSO$_4$. After concentration, purification was carried out by silica gel chromatography (ethyl acetate) to give the title compound.
$^1$H NMR (CDCl$_3$, 270 MHz) δ 7.05 (d, J=1.5 Hz, 1H), 6.91 (d, J=1.5 Hz, 1H), 3.77 (t, J=6 Hz, 2H), 2.68 (t, J=6 Hz, 2H), 2.54 (q, J=7 Hz, 4H), 0.97 (t, J=7 Hz, 6H).

Reference Example 9

1-(2-Diisopropylaminoethyl)-4,6-dichloroisatin

This compound was prepared by the same method as that described in reference example 8, using 2-diisopropylaminoethyl chloride hydrochloride in place of 2-diethylaminoethyl chloride hydrochloride.
$^1$H NMR (CDCl$_3$, 270 MHz) δ 7.04 (d, J=1.3 Hz, 1H), 6.87 (s, 1H), 3.69 (t, J=6.6 Hz, 2H), 3.03 (hep, J=6.6 Hz, 2H), 2.70 (t, J=6.3 Hz, 2H), 0.96 (d, J=6.3 Hz, 12H).

Reference Example 10

1-(2-Diethylaminoethyl)-4-bromoisatin and 1-(2-Diethylaminoethyl)-6-bromoisatin

These compounds were prepared by the same method as that described in reference example 8, using the mixture of reference example 2 (2.5:1) in place of the compound of reference example 1. Separation of 1-(2-diethylaminoethyl)-4-bromoisatin and 1-(2-diethylaminoethyl)-6-bromoisatin was carried out by silica gel chromatography (hexane:ethyl acetate, 1:1 to 0:1 gradient). 1-(2-Diethylaminoethyl)-4-bromoisatin:
$^1$H NMR (CDCl$_3$, 270 MHz) δ 7.44 (d, J=7.7 Hz, 1H), 7.25 (dd, J=1.5, 7.7 Hz, 1H), 7.17 (d, J=1.5 Hz, 1H), 3.77 (t, J=6.6 Hz, 2H), 2.69 (t, J=6.6 Hz, 2H), 2.55 (q, J=7.1 Hz, 4H), 0.97 (t, J=7.1 Hz, 6H).
1-(2-Diethylaminoethyl)-6-bromoisatin:
$^1$H NMR (CDCl$_3$, 270 MHz) δ 7.39 (dd, J=7.8, 7.8 Hz, 1H), 7.23 (d, J=7.8 Hz, 1H), 6.90 (d, J=7.8 Hz, 1H), 3.80 (t, J=6.8 Hz, 2H), 2.68 (t, J=6.8 Hz, 2H), 2.56 (q, J=7.1 Hz, 4H), 0.97 (t, J=7.1 Hz, 6H).

Reference Example 11

1-(3-Dimethylaminoethyl)-4-bromoisatin

This compound was prepared by the same method as that described in reference example 8, using 3-dimethylaminoethyl chloride hydrochloride in place of 2-diethylaminoethyl chloride hydrochloride and using the mixture of reference example 2 (2.5:1) in place of the compound of reference example 1. Purification was carried out by silica gel chromatography (hexane:ethyl acetate, 1:1 to 0.1:1 gradient).
$^1$H NMR (CDCl$_3$, 270 MHz) 7.40 (dd, J=6.9, 7.9 Hz, 1H), 7.24 (d, J=7.9 Hz, 1H), 6.89 (d, J=7.9 Hz, 1H), 3.83 (t, J=6.8 Hz, 2H), 2.57 (t, 2H, J=6.8 Hz, 2H), 2.29 (s, 6H).

Reference Example 12

1-(3-Dimethylaminopropyl)-4-bromoisatin

This compound was prepared by the same method as that described in reference example 8, using 3-dimethylaminopropyl chloride hydrochloride in place of 2-diethylaminoethyl chloride hydrochloride and using the mixture of reference example 2 (2.5:1) in place of the compound of reference example 1. Purification was carried out by silica gel chromatography (hexane:ethyl acetate, 1:1 to 0.1:1 gradient).
$^1$H NMR (CDCl$_3$, 270 MHz) δ 7.39 (dd, J=7.8, 7.8 Hz, 1H), 7.23 (d, J=7.8 Hz, 1H), 6.97 (d, J=7.8 Hz, 1H), 3.81 (t, J=6.8 Hz, 2H), 2.33 (t, J=6.8 Hz, 2H), 2.18 (s, 6H), 1.84 (dt, J=6.8, 6.8 Hz, 2H).

Reference Example 13

1-(2-Diethylaminoethyl)-7-bromoisatin

This compound was prepared by the same method as that described in reference example 8, using the compound of reference example 3 in place of the compound of reference example 1.
$^1$H NMR (CDCl$_3$, 270 MHz) δ 7.70 (dd, J=1.3, 8.2 Hz, 1H), 7.58 (dd, J=1.3, 7.3 Hz, 1H), 6.98 (dd, J=7.3, 8.2 Hz, 1H), 4.27 (t, J=6.8 Hz, 2H), 2.69 (t, J=6.8 Hz, 2H), 2.51 (q, J=7.1 Hz, 4H), 0.89 (t, J=7.1 Hz, 6H).

Reference Example 14

1-(2-Diethylaminoethyl)-5-bromoisatin

This compound was prepared by the same method as that described in reference example 8, using 5-bromoisatin in place of the compound of reference example 1.
$^1$H NMR (CDCl$_3$, 270 MHz) δ 7.69 (d, J=2 Hz, 1H), 7.69 (dd, J=9, 2 Hz, 1H), 6.88 (d, J=9 Hz, 1H), 3.78 (t, J=6.5 Hz, 2H), 2.68 (t, J=6.5 Hz, 2H), 2.55 (q, J=7 Hz, 4H), 0.96 (t, J=7 Hz, 6H).

Reference Example 15

1-(2-Diethylaminoethyl)-5-chloroisatin

This compound was prepared by the same method as that described in reference example 8, using 5-chloroisatin in place of the compound of reference example 1.
$^1$H NMR (CDCl$_3$, 270 MHz) δ 7.55 (d, J=2 Hz, 1H), 7.54 (dd, J=9, 2 Hz, 1H), 6.92 (d, J=9 Hz, 1H), 3.79 (t, J=7 Hz, 2H), 2.69 (t, J=7 Hz, 2H), 2.55 (q, J=7 Hz, 4H), 0.97 (t, J=7 Hz, 6H).

Reference Example 16

1-(3-Diethylaminopropyl)-5-chloroisatin

This compound was prepared by the same method as that described in reference example 8, using 3-diethylaminopropyl chloride hydrochloride in place of 2-diethylaminoethyl chloride hydrochloride, and using 5-chloroisatin in place of the compound of reference example 1.

Reference Example 17

1-(2-Diethylaminoethyl)-4,6-dimethylisatin

This compound was prepared by the same method as that described in reference example 8, using the compound of reference example 4 in place of the compound of reference example 1.

$^1$H NMR (CDCl$_3$, 270 MHz) δ 6.67 (s, 1H), 6.54 (s, 1H), 3.76 (t, J=7.0 Hz, 2H), 2.68 (t, J=7.0 Hz, 2H), 2.58 (q, J=7.1 Hz, 4H), 2.52 (s, 3H), 2.37 (s, 3H), 1.00 (t, J=7.1 Hz, 6H).

Reference Example 18

Mixture of 1-(2-Diethylaminoethyl)-4-iodo-6-chloroisatin and 1-(2-Diethylaminoethyl)-6-iodo-4-chloroisatin This mixture (3:1) was prepared by the same method as that described in reference example 8, using the mixture of reference example 5 in place of the compound of reference example 1.

1-(2-Diethylaminoethyl)-4-iodo-6-chloroisatin:
$^1$H NMR (DMSO-d$_6$, 270 MHz) δ 7.53 (d, J=1.5 Hz, 1H), 6.99 (d, J=1.5 Hz, 1H), 3.77 (t, J=6.4 Hz, 2H), 2.67 (t, J=6.4 Hz, 2H), 2.55 (q, J=7.1 Hz, 4H), 0.97 (t, J=7.1 Hz, 6H).

1-(2-Diethylaminoethyl)-6-iodo-4-chloroisatin:
$^1$H NMR (DMSO-d$_6$, 270 MHz) δ 7.46 (s, 1H), 7.30 (s, 1H), 3.77 (t, J=6.4 Hz, 2H), 2.67 (t, J=6.4 Hz, 2H), 2.55 (q, J=7.1 Hz, 4H), 0.97 (t, J=7.1 Hz, 6H).

Reference Example 19

1-(2-Diethylaminoethyl)-4-trifluoromethylisatin

This compound was prepared by the same method as that described in reference example 8, using the compound of reference example 6 in place of the compound of reference example 1.

$^1$H NMR (CDCl$_3$, 270 MHz) δ 7.73 (t, J=9 Hz, 1H), 7.40 (d, J=8.1 Hz, 1H), 7.31 (m, 1H), 3.87 (t, J=6.0 Hz, 2H), 2.85 (t, J=6.0 Hz, 2H), 2.60 (q, J=6.3 Hz, 4H), 1.03 (t, J=6.3 Hz, 6H).

Reference Example 20

Mixture of 1-(2-Diethylaminoethyl)-5-bromo-4-chloroisatin and 1-(2-Diethylaminoethyl)-5-bromo-4-chloroisatin This mixture (1.8:1) was prepared by the same method as that described in reference example 8, using the mixture of reference example 7 in place of the compound of reference example 1.

1-(2-Diethylaminoethyl)-5-bromo-4-chloroisatin:
$^1$H NMR (CDCl$_3$, 270 MHz) δ 7.79 (d, J=8.5 Hz, 1H), 6.81 (d, J=8.5 Hz, 1H), 3.79 (t, J=6.5 Hz, 2H), 2.68 (t, J=6.5 Hz, 2H), 2.56 (q, J=7 Hz, 4H), 0.96 (t, J=7 Hz, 6H).

1-(2-Diethylaminoethyl)-5-bromo-4-chloroisatin:
$^1$H NMR (CDCl$_3$, 270 MHz) δ 7.79 (1H, s), 7.15 (1H, s), 3.77 (t, J=6.5 Hz, 2H), 2.69 (t, J=6.5 Hz, 2H), 2.55 (q, J=7 Hz, 4H), 0.96 (t, J=7 Hz, 6H).

Reference Example 21

Mixture of 1-(2-Diethylaminoethyl)-4-chloro-6-(3-t-butyldimethylsilyloxy-1-propynyl)isatin and 1-(2-Diethylaminoethyl)-6-chloro-4-(3-t-butyldimethylsilyloxy-1-propynyl)isatin To the mixture of reference example 18 (3:1, 392.0 mg, 0.96 mmol) and bis(triphenylphosphine)palladium (11) chloride (33.7 mg, 20 mol %) in triethylamine (4.0 mL) was added t-butyldimethylsilyl(2-propynyloxy)silane (244.8 mg, 1.5 eq) and copper (I) iodide (8.3 mg, 22 mol %). The mixture was stirred at 60° C. for 1.5 hours. After cooling, water was added and the mixture was extracted with ethyl acetate. The organic phase was dried over anhydrous MgSO$_4$ and concentrated. Purification was carried out by silica gel chromatography (hexane:ethyl acetate, 1:1 to 1:1.5 gradient) to give the desired mixture (2:1).

1-(2-Diethylaminoethyl)-4-chloro-6-(3-t-butyldimethylsilyloxy-1-propynyl)isatin:
$^1$H NMR (CDCl$_3$, 270 MHz) δ 7.08 (d, J=1.7 Hz, 1H), 6.93 (d, J=1.7 Hz, 1H), 4.63 (s, 2H), 3.76 (t, J=6.4 Hz, 2H), 2.67 (t, J=6.4 Hz, 2H), 2.55 (q, J=7.1 Hz, 4H), 0.97 (t, J=7.1 Hz, 6H), 0.93 (s, 9H), 0.18 (s, 6H).

1-(2-Diethylaminoethyl)-6-chloro-4-(3-t-butyldimethylsilyloxy-1-propynyl)isatin:
$^1$H NMR (CDCl$_3$, 270 MHz) δ 7.06 (s, 1H), 6.87 (s, 1H), 4.56 (s, 2H), 3.78 (t, J=6.4 Hz, 2H), 2.67 (t, J=6.4 Hz, 2H), 2.55 (q, J=7.1 Hz, 4H), 0.97 (t, J=7.1 Hz, 6H), 0.95 (s, 9H), 0.17 (s, 6H).

Reference Example 22

Mixture of 1-(2-Diethylaminoethyl)-4-chloro-6-(4-t-butyldimethylsilyloxy-1-butynyl)isatin and 1-(2-Diethylaminoethyl)-6-chloro-4-(4-t-butyldimethylsilyloxy-1-butynyl)isatin This mixture (3.7:1) was prepared by the same method as that described in reference example 21, using t-butyldimethylsilyl(3-butynyloxy)silane in place of t-butyldimethylsilyl(2-propynyloxy)silane.

1-(2-Diethylaminoethyl)-4-chloro-6-(4-t-butyldimethylsilyloxy-1-butynyl)isatin:
$^1$H NMR (CDCl$_3$, 270 MHz) δ 7.03 (d, J=1.7 Hz, 1H), 6.88 (d, J=1.7 Hz, 1H), 3.88 (t, J=7.0 Hz, 2H), 3.75 (t, J=6.6 Hz, 2H), 2.74 (t, J=7.0 Hz, 2H), 2.67 (t, J=6.6 Hz, 2H), 2.54 (q, J=7.1 Hz, 4H), 0.97 (t, J=7.1 Hz, 6H), 0.91 (s, 9H), 0.09 (s, 6H).

1-(2-Diethylaminoethyl)-6-chloro-4-(4-t-butyldimethylsilyloxy-1-butynyl)isatin:
$^1$H NMR (CDCl$_3$, 270 MHz) δ 7.03 (s, 1H), 6.82 (s, 1H), 3.88 (t, J=7.0 Hz, 2H), 3.83 (t, J=6.6 Hz, 2H), 2.74 (t, J=7.0 Hz, 2H), 2.67 (t, J=6.6 Hz, 2H), 2.54 (q, J=7.1 Hz, 4H), 0.97 (t, J=7.1 Hz, 6H), 0.92 (s, 9H), 0.10 (s, 6H).

Reference Example 23

4,6-Dichloro-3-hydroxy-3-(2-naphthyl)oxindole

To a solution of 2-bromonaphthalene (2.952 g) in anhydrous THF (25 mL) was added portion wise a solution of n-butyl lithium in n-hexane (1.55 N, 10.12 mL) at −78° C. The reaction solution was stirred for 30 minutes. To the mixture was then added portion wise a solution of 4,6-dichloroisatin (1.54 g) in anhydrous THF (25 ml) for 50 minutes. The reaction mixture was stirred for 2 hours. Then the mixture was allowed to warm to room temperature. To the mixture was added 1N HCl and extracted by ethyl acetate. The organic phase was separated, washed with 1N HCl and brine and dried over MgSO$_4$ and concentrated . Purification was carried out by silica gel chromatography (hexane:ethyl acetate, 2:1 to 1:1 gradient) to give the title compound (0.652 g, yield: 27%).

$^1$H NMR (DMSO-d$_6$, 300 MHz) δ 6.93 (1H, s), 6.96 (1H, d, J=1.7 Hz), 7.12 (1H, d, J=1.7 Hz), 7.23 (1H, m), 7.49 (2H, m), 7.80–7.94 (4H, m), 10.80 (1H, brs).

Reference Example 24

1-(2-Diethylaminoethyl)-4-trifluoromethyl-6-iodoisatin

This compound was prepared by the same method as that described in reference example 8, using a mixture of 4-trifluoromethyl-6-iodoisatin and 6-trifluoromethyl-4-iodoisatin in place of the compound of reference example 18. Purification was carried out by silica gel chromatography.

$^1$H NMR (CDCl$_3$) δ 7.71 (s, 1H), 7.68 (s, 1H), 3.80 (t, 2H, J=6.1 Hz), 2.69 (t, 2H, J=6.1 Hz), 2.55 (q, 4H, J=7.1 Hz), 0.97 (t, 6H, J=7.1 Hz).

Example 1

4,6-Dichloro-1-(2-diethylaminoethyl)-3-hydroxy-3-(2-naphthyl)oxindole

To a solution of the compound of reference example 8 (102.6 mg, 0.317 mmol) in anhydrous THF (0.6 mL) was added portionwise at room temperature the Grignard reagent which was prepared from 2-bromonaphthalene (98.5 mg, 1.5 eq) and magnesium (11.4 mg, 1.5 eq). The reaction mixture was stirred overnight. Methanol was added to stop the reaction and concentrated. Saturated aqueous NaHCO$_3$ was then added and the mixture extracted with ethyl acetate. The organic phase was dried over anhydrous MgSO$_4$ and concentrated. Purification by silica gel chromatography (1% methanol in chloroform) gave the title compound 33.3 mg.

$^1$H NMR (CDCl$_3$, 270 MHz) δ 7.98 (d, J=2 Hz, 1H), 7.78–7.83 (m, 2H), 7.77 (d, J=8.5 Hz, 1H), 7.44–7.50 (m, 2H), 7.36 (dd, J=8, 2 Hz, 1H), 7.04 (d, J=1.5 Hz, 1H), 6.95 (d, J=1.5 Hz, 1H), 3.87 (dt, J=13, 6.5 Hz, 1H), 3.69 (dt, J=13, 6.5 Hz, 1H), 2.70 (t, J=6.5 Hz, 2H), 2.56 (q, J=7 Hz, 4H), 0.96 (t, J=7 Hz, 6H).

Example 2

4,6-Dichloro-1-(2-diethylaminoethyl)-3-hydroxy-3-(3-fluorophenyl)oxindole

This compound was prepared by the same procedure as described in example 1, using 1-bromo-3-fluorobenzene in place of 2-bromonaphthalene.

$^1$H NMR (CDCl$_3$, 270 MHz) δ 7.24–7.32 (m, 1H), 7.13–7.21 (m, 2H), 7.03 (d, J=1.5 Hz, 1H), 6.96–7.03 (m, 1H), 6.92 (d, J=1.5 Hz, 1H), 3.88 (dt, J=14, 7 Hz, 1H), 3.65 (dt, J=14, 7 Hz, 1H), 2.69 (t, J=7 Hz, 1H), 2.68 (t, J=7 Hz, 1H), 2.55 (q, J=7 Hz, 4H), 0.95 (t, J=7 Hz, 6H).

Example 3

4,6-Dichloro-1-(2-diethylaminoethyl)-3-hydroxy-3-(4-fluorophenyl)oxindole

This compound was prepared by the same procedure as described in example 1, using 1-bromo-4-fluorobenzene in place of 2-bromonaphthalene.

$^1$H NMR (CDCl$_3$, 270 MHz) δ 7.35–7.42 (m, 2H), 7.03 (d, J=1.5 Hz, 1H), 6.97–7.07 (m, 2H), 6.91 (d, J=1.5 Hz, 1H), 3.66–3.88 (m, 2H), 2.70 (t, J=7 Hz, 2H), 2.57 (q, J=7 Hz, 4H), 0.96 (t, J=7 Hz, 6H).

Example 4

4,6-Dichloro-1-(2-diethylaminoethyl)-3-hydroxy-3-(4-methoxyphenyl)oxindole

This compound was prepared by the same procedure as described in example 1, using 1-bromo-4-methoxyanisole in place of 2-bromonaphthalene.

1H NMR (CDCl$_3$, 270 MHz) δ 7.21 (d, J=9 Hz, 2H), 7.03 (d, J=1.5 Hz, 1H), 6.90 (d, J=1.5 Hz, 1H), 6.85 (d, J=9 Hz, 2H), 3.79 (s, 3H), 3.82 (dt, J=14, 6.5 Hz, 1H), 3.67 (dt, J=14, 6.5 Hz, 1H), 2.68 (t, J=6.5 Hz, 2H), 2.55 (q, J=7 Hz, 4H), 0.96 (t, J=7 Hz, 6H).

Example 5

4,6-Dichloro-1-(2-diethylaminoethyl)-3-hydroxy-3-(3,4-difluorophenyl)oxindole This compound was prepared by the same procedure as described in example 1, using 1-bromo-3,4-difluorobenzene in place of 2-bromonaphthalene.

$^1$H NMR (CDCl$_3$, 270 MHz) δ 7.29–7.37 (m, 1H), 7.04–7.14 (m, 2H), 7.03 (d, J=1.5 Hz, 1H), 6.91 (d, J=1.5 Hz, 1H), 3.89 (dt, J=14, 7 Hz, 1H), 3.65 (dt, J=14, 7 Hz, 1H), 2.65–2.72 (m, 2H), 2.55 (q, J=7 Hz, 4H), 0.94 (t, J=7 Hz, 6H).

Example 6

4,6-Dichloro-1-(2-diethylaminoethyl)-3-hydroxy-3-(2-fluorophenyl)oxindole

This compound was prepared by the same procedure as described in example 1, using 1-bromo-2-fluorobenzene in place of 2-bromonaphthalene.

$^1$H NMR (CDCl$_3$, 270 MHz) δ 7.97 (ddd, J=1.9, 7.8, 7.8 Hz, 1H), 7.21–7.36 (m, 3H), 6.96 (d, J=1.7 Hz, 1H), 6.91 (d, J=1.7 Hz, 1H), 6.89–6.97 (m, 1H), 3.75–3.90 (m, 3H), 2.51–2.82 (m, 6H), 1.03 (t, J=7.3 Hz, 6H).

Example 7

4,6-Dichloro-1-(2-diethylaminoethyl)-3-hydroxy-3-(2-chlorophenyl)oxindole

This compound was prepared by the same procedure as described in example 1, using 1-bromo-2-chlorobenzene in place of 2-bromonaphthalene.

$^1$H NMR (CDCl$_3$, 270 MHz) δ 8.16 (dd, J=1.5, 7.5 Hz, 1H), 7.40 (ddd, J=1.5, 7.5, 7.5 Hz, 1H), 7.23–7.33 (m, 2H), 6.95 (d, J=1.7 Hz, 1H), 6.88 (d, J=1.7 Hz, 1H), 3.90–4.01 (m, 1H), 3.65–3.75 (m, 1H), 2.52–2.85 (m, 6H), 1.03 (t, J=7.3 Hz, 6H).

Example 8

4,6-Dichloro-1-(2-diethylaminoethyl)-3-hydroxy-3-(2-trifluoromethylphenyl)oxindole This compound was prepared by the same procedure as described in example 1, using 1-bromo-2-trifluorobenzene in place of 2-bromonaphthalene.

$^1$H NMR (CDCl$_3$, 270 MHz) δ 8.42 (br, 1H), 7.66–7.69 (m, 2H), 7.48 (dd, J=7.6, 7.6 Hz, 1H), 6.95 (d, J=1.5 Hz, 1H), 6.88 (d, J=1.5 Hz, 1H), 3.91–4.02 (m, 1H), 3.59–3.69 (m, 1H), 2.75–2.86 (m, 2H), 2.49–2.71 (m, 4H), 1.01 (t, J=7.1 Hz, 6H).

Example 9

4,6-Dichloro-1-(2-diethylaminoethyl)-3-hydroxy-3-(3,4-dichlorophenyl)oxindole This compound was prepared by the same procedure as described in example 1, using 1-bromo-3,4-dichlorobenzene in place of 2-bromonaphthalene.

$^1$H NMR (CDCl$_3$, 270 MHz) δ 7.53 (d, J=2.1 Hz, 1H), 7.40 (d, J=8.4 Hz, 1H), 7.27 (dd, J=2.1, 8.4 Hz, 1H), 7.04 (d,

J=1.7 Hz, 1H), 6.90 (d, J=1.7 Hz, 1H), 3.81–3.91 (m, 1H), 3.65–3.75 (m, 1H), 2.70 (t, J=5.6 Hz, 2H), 2.56 (q, J=7.1 Hz, 4H), 0.94 (t, J=7.1 Hz, 6H).

Example 10

4,6-Dichloro-1-(2-diethylaminoethyl)-3-hydroxy-3-(2-dimethylaminosulfonylphenyl)oxindole To a solution of the compound of reference example 8 (45.4 mg, 0.14 mmol) in anhydrous THF (0.6 mL) was added portionwise at 0° C. the organolithium reagent which was prepared from a solution of N,N-dimethylbezenesulfonamide (40.0 mg, 0.22 mmol) in anhydrous THF (1.0 mL) and n-butyllithium (0.135 mL, 1.6M in hexanes) at 0° C. The mixture was stirred overnight. Methanol was added to stop the reaction and concentrated. Saturated aqueous $NaHCO_3$ was then added and the mixture extracted with ethyl acetate. The organic phase was dried over anhydrous $MgSO_4$ and concentrated. Purification by silica gel chromatography (1% methanol in chloroform) gave the title compound.

$^1$H NMR ($CDCl_3$, 270 MHz) δ 8.61 (d, J=7.6 Hz, 1H), 7.74–7.66 (m, 2H), 7.51 (dd, J=7.6, 7.6 Hz, 1H), 6.91 (s, 1H), 6.84 (s, 1H), 3.52–3.57 (m, 2H), 2.83–2.90 (m, 2H), 2.60 (s, 6H), 2.53–2.72 (m, 4H), 1.01 (t, J=7.1 Hz, 6H).

Example 11

4,6-Dichloro-1-(2-diisopropylaminoethyl)-3-hydroxy-3-(2-naphthyl)oxindole

This compound was prepared by the same procedure as described in example 1, using the compound of reference example 9 in place of the compound of reference example 8.

$^1$H NMR ($CDCl_3$, 270 MHz) δ 7.93 (d, J=2.0 Hz, 1H), 7.78–7.83 (m, 3H), 7.45–7.51 (m, 2H), 7.35 (dd, J=2.0, 8.6 Hz, 1H), 7.05 (d, J=1.7 Hz, 1H), 6.95 (d, J=1.7 Hz, 1H), 3.56–3.77 (m, 2H), 2.99–3.08 (m, 2H), 2.70 (t, J=6.8 Hz, 2H), 0.98 (d, J=6.6 Hz, 6H), 0.97 (d, J=6.6 Hz, 6H).

Example 12

4,6-Dichloro-1-(2-diisopropylaminoethyl)-3-hydroxy-3-(2-chlorophenyl)oxindole

This compound was prepared by the same procedure as described in example 1, using the compound of reference example 9 in place of the compound of reference example 8 and using 1-bromo-2-chlorobenzene in place of 2-bromonaphthalene.

$^1$H NMR ($CDCl_3$, 270 MHz) δ 8.12 (dd, J=1.3, 7.9 Hz, 1H), 7.24–7.43 (m, 3H), 6.94 (d, J=1.7 Hz, 1H), 6.86 (d, J=1.7 Hz, 1H), 3.57–3.81 (m, 2H), 3.02–3.11 (m, 2H), 2.63–2.82 (m, 2H), 1.05 (d, J=6.6 Hz, 6H), 1.04 (d, J=6.6 Hz, 6H).

Example 13

4,6-Dichloro-1-(2-diisopropylaminoethyl)-3-hydroxy-3-(2-trifluoromethylphenyl)oxindole This compound was prepared by the same procedure as described in example 1, using the compound of reference example 9 in place of the compound of reference example 8 and using 1-bromo-2-trifluoromethylbenzene in place of 2-bromonaphthalene.

$^1$H NMR ($CDCl_3$, 270 MHz) δ 8.31 (br, 1H), 7.68–7.71 (m, 2H), 7.45–7.51 (m, 2H), 7.49 (dd, J=7.6, 7.6 Hz, 1H), 6.95 (d, J=1.7 Hz, 1H), 6.87 (d, J=1.7 Hz, 1H), 3.54–3.76 (m, 2H), 3.01–3.13 (m, 2H), 2.69 (t, J=7.4 Hz, 2H), 1.04 (d, J=6.6 Hz, 6H), 1.03 (d, J=6.6 Hz, 6H).

Example 14

4,6-Dichloro-1-(2-diisopropylaminoethyl)-3-hydroxy-3-(2-dimethylaminosulfonylphenyl)oxindole This compound was prepared by the same procedure as described in example 10, using the compound of reference example 9 in place of the compound of reference example 8.

$^1$H NMR ($CDCl_3$, 270 MHz) δ 8.54 (d, J=8.3 Hz, 1H), 7.66–7.74 (m, 2H), 7.49–7.55 (m, 1H), 6.90 (s, 1H), 6.85 (s, 1H), 3.81–3.83 (m, 1H), 3.53–3.55 (m, 1H), 3.05 (m, 2H), 2.67–2.75 (m, 2H), 2.61 (s, 6H), 1.02–1.06 (m, 12H).

Example 15

4,6-Dichloro-1-(2-diisopropylaminoethyl)-3-hydroxy-3-(3,4-dichlorolphenyl)oxindole This compound was prepared by the same procedure as described in example 1, using the compound of reference example 9 in place of the compound of reference example 8 and using 1-bromo-3,4-dichlorobenzene in place of 2-bromonaphthalene.

$^1$H NMR ($CDCl_3$, 270 MHz) δ 7.47 (d, J=2.1 Hz, 1H), 7.40 (d, J=8.5 Hz, 1H), 7.19 (dd, J=2.1, 8.5 Hz, 1H), 7.05 (d, J=1.7 Hz, 1H), 6.92 (d, J=1.7 Hz, 1H), 3.53–3.76 (m, 2H), 2.99–3.08 (m, 2H), 2.68 (t, J=6.6 Hz, 2H), 0.97 (d, J=6.6 Hz, 6H), 0.96 (d, J=6.6 Hz, 6H).

Example 16

5-Chloro-1-(2-diethylaminoethyl)-3-hydroxy-3-(2-naphthyl)oxindole

This compound was prepared by the same procedure as described in example 1, using the compound of reference example 16 in place of the compound of reference example 8.

$^1$H NMR ($CDCl_3$, 270 MHz) δ 7.96 (s, 1H), 7.74 (m, 3H), 7.41–7.48 (m, 3H), 7.29 (dd, J=8, 2 Hz, 1H), 6.89 (d, J=8 Hz, 1H), 3.96 (dt, J=14, 7 Hz, 1H), 3.74 (dt, J=14, 7 Hz, 1H), 2.75 (t, J=7 Hz, 2H), 2.61 (q, J=7 Hz, 2H), 2.60 (q, J=7 Hz, 2H), 0.99 (t, J=7 Hz, 6H).

Example 17

5-Chloro-1-(2-diethylaminoethyl)-3-hydroxy-3-(2-methoxyphenyl)oxindole

This compound was prepared by the same procedure as described in example 1, using the compound of reference example 15 in place of the compound of reference example 8 and using 1-bromo-2-methoxybenzene in place of 2-bromonaphthalene.

$^1$H NMR ($CDCl_3$, 270 MHz) δ 7.69 (dd, J=7.5, 2 Hz, 1H), 7.31 (td, J=8, 2 Hz, 1H), 7.26 (dd, J=8, 2 Hz, 1H), 7.08 (d, J=2 Hz, 1H), 7.04 (ddd, J=8, 7.5, 2 Hz, 1H), 6.85 (d, J=8 Hz, 1H), 6.84 (dd, J=8, 2 Hz, 1H), 3.83 (t, J=7 Hz, 2H), 3.62 (s, 3H), 2.75 (t, J=7 Hz, 2H), 2.64 q, J=7 Hz, 4H), 1.06 (t, J=7 Hz, 6H).

Example 18

5-Chloro-1-(3-diethylaminopropyl)-3-hydroxy-3-(2-fluorophenyl)oxindole

This compound was prepared by the same procedure as described in example 1, using the compound of reference example 16 in place of the compound of reference example 8 and using 1-bromo-2-fluorobenzene in place of 2-bromonaphthalene.

$^1$H NMR (CDCl$_3$, 270 MHz) δ 7.91 (td, J=7.5, 2 Hz, 1H), 7.18–7.36 (m, 3H), 7.08 (d, J=2 Hz, 1H), 6.93 (td, J=8, 2 Hz, 1H), 6.90 (d, J=8.5 Hz, 1H), 3.68–3.95 (m, 2H), 2.53–2.70 (m, 6H), 1.92–2.05 (m, 2H), 1.08 (t, J=7 Hz, 6H).

Example 19

5-Chloro-1-(3-diethylaminopropyl)-3-hydroxy-3-(2-methoxyphenyl)oxindole

This compound was prepared by the same procedure as described in example 1, using the compound of reference example 16 in place of the compound of reference example 8 and using 1-bromo-2-methoxybenzene in place of 2-bromonaphthalene.

$^1$H NMR (CDCl$_3$, 270 MHz) δ 7.72 (dd, J=8, 2 Hz, 1H), 7.31 (td, J=8, 2 Hz, 1H), 7.25 (dd, J=8, 2 Hz, 1H), 7.05 (td, J=8, 2 Hz, 1H), 7.05 (d, J=2 Hz, 1H), 6.85 (d, J=8 Hz, 1H), 6.82 (d, J=8 Hz, 1H), 3.77 (t, J=7 Hz, 2H), 3.59 (s, 3H), 2.54–2.62 (m, 6H), 1.85–1.96 (m, 2H), 1.04 (t, J=7 Hz, 6H).

Example 20

5-Chloro-1-(3-diethylaminopropyl)-3-hydroxy-3-(2-naphthyl)oxindole

This compound was prepared by the same procedure as described in example 1, using the compound of reference example 16 in place of the compound of reference example 8.

$^1$H NMR (CDCl$_3$, 270 MHz) δ 7.90 (d, J=2 Hz, 1H), 7.76–7.82 (m, 1H), 7.77 (d, J=9 Hz, 1H), 7.45–7.50 (m, 2H), 7.33 (dd, J=8, 2 Hz, 1H), 7.30 (d, J=2 Hz, 1H), 7.26 (dd, J=8, 2 Hz, 1H), 6.92 (d, J=8 Hz, 1H), 3.72–3.79 (m, 2H), 2.47–2.58 (m, 6H), 1.83–1.94 (m, 2H), 0.99 (t, J=7 Hz, 6H).

Example 21

4-Bromo-1-(2-diethylaminoethyl)-3-hydroxy-3-(2-fluorophenyl)oxindole

This compound was prepared by the same procedure as described in example 1, using 1-(2-diethylaminoethyl)-4-bromoisatin (reference example 10) in place of the compound of reference example 8 and using 1-bromo-2-fluorobenzene in place of 2-bromonaphthalene.

$^1$H NMR (CDCl$_3$, 270 MHz) δ 8.00 (ddd, J=2.1, 7.8, 7.8 Hz, 1H), 7.05–7.47 (m, 4H), 6.88–6.95 (m, 2H), 3.83 (t, J=7.3 Hz, 2H), 2.53–2.82 (m, 6H), 1.03 (t, J=7.1 Hz, 6H).

Example 22

4-Bromo-1-(2-diethylaminoethyl)-3-hydroxy-3-(2-methoxyphenyl)oxindole

This compound was prepared by the same procedure as described in example 1, using 1-(2-diethylaminoethyl)-4-bromoisatin (reference example 10) in place of the compound of reference example 8 and using 1-bromo-2-methoxybenzene in place of 2-bromonaphthalene.

1H NMR (CDCl$_3$, 270 MHz) δ 7.72 (brd, 1H), 7.31 (ddd, J=1.8, 7.7, 7.7 Hz, 1H), 7.01–7.20 (m, 3H), 6.86 (dd, J=1.3, 7.7 Hz, 1H), 6.83 (d, J=8.3 Hz, 1H), 3.79–3.86 (m, 2H), 3.58 (s, 3H), 2.70–2.76 (m, 2H), 2.63 (q, J=6.9 Hz, 4H), 1.06 (t, J=6.9 Hz, 6H).

Example 23

4-Bromo-1-(2-diethylaminoethyl)-3-hydroxy-3-(2-naphthyl)oxindole

This compound was prepared by the same procedure as described in example 1, using 1-(2-diethylaminoethyl)-4-bromoisatin (reference example 10) in place of the compound of reference example 8.

$^1$H NMR (CDCl$_3$, 270 MHz) δ 8.00 (d, J=1.6 Hz, 1H), 7.75–7.85 (m, 3H), 7.44–7.50 (m, 2H), 7.34 (dd, J=2.0, 8.6 Hz, 1H), 7.19–7.30 (m, 2H), 6.97 (dd, J=1.0, 7.6 Hz, 1H), 3.61–3.93 (m, 2H), 2.72 (t, J=6.9 Hz, 2H), 2.57 (q, J=7.1 Hz, 4H), 0.97 (t, J=7.1 Hz, 6H).

Example 24

4-Bromo-1-(2-diethylaminoethyl)-3-hydroxy-3-(4-biphenyl)oxindole

This compound was prepared by the same procedure as described in example 1, using 1-(2-diethylaminoethyl)-4-bromoisatin (reference example 10) in place of the compound of reference example 8 and using 4-bromo-biphenyl in place of 2-bromonaphthalene.

$^1$H NMR (CDCl$_3$, 270 MHz) δ 7.54–7.58 (m, 4H), 7.20–7.47 (m, 8H), 6.97 (d, J=5.6 Hz, 1H), 3.86 (m, 2H), 2.64–2.85 (m, 6H), 1.03 (t, J=7.1 Hz, 6H).

Example 25

6-Bromo-1-(2-diethylaminoethyl)-3-hydroxy-3-(2-fluorophenyl)oxindole

This compound was prepared by the same procedure as described in example 1, using 1-(2-diethylaminoethyl)-6-bromoisatin (reference example 10) in place of the compound of reference example 8 and using 1-bromo-2-fluorobenzene in place of 2-bromonaphthalene.

$^1$H NMR (CDCl$_3$, 270 MHz) δ 7.86 (ddd, J=1.9, 7.8, 7.8 Hz, 1H), 6.90–7.48 (m, 6H), 3.83 (t, J=6.9 Hz, 2H), 2.55–2.82 (m, 6H), 1.05 (t, J=7.1 Hz, 6H).

Example 26

7-Bromo-1-(2-diethylaminoethyl)-3-hydroxy-3-(2-fluorophenyl)oxindole

This compound was prepared by the same procedure as described in example 1, using the compound of reference example 13 in place of the compound of reference example 8 and using 1-bromo-2-fluorobenzene in place of 2-bromonaphthalene.

$^1$H NMR (CDCl$_3$, 270 MHz) δ 7.91 (ddd, J=1.9, 7.6, 7.6 Hz, 1H), 6.78–7.57 (m, 6H), 4.20–4.48 (m, 2H), 2.37–2.75 (m, 6H), 0.97 (t, J=7.3 Hz, 6H).

Example 27

7-Bromo-1-(2-diethylaminoethyl)-3-hydroxy-3-(2-naphthyl)oxindole

This compound was prepared by the same procedure as described in example 1, using the compound of reference example 13 in place of the compound of reference example 8.

$^1$H NMR (CDCl$_3$, 270 MHz) δ 7.97 (s, 1H), 7.75–7.83 (m, 3H), 7.41–7.49 (m, 4H), 7.20 (dd, J=1.3, 7.3 Hz, 1H), 6.91 (dd, J=7.8, 7.8 Hz, 1H), 4.31 (t, J=6.8 Hz, 2H), 2.69–2.84 (m, 2H), 2.53–2.66 (m, 4H), 0.96 (t, J=7.3 Hz, 6H).

Example 28

7-Bromo-1-(2-diethylaminoethyl)-3-hydroxy-3-(4-biphenyl)oxindole

This compound was prepared by the same procedure as described in example 1, using the compound of reference example 13 in place of the compound of reference example 8 and using 4-bromo-biphenyl in place of 2-bromonaphthalene.

$^1$H NMR (CDCl$_3$, 270 MHz) δ 7.33–7.56 (m, 10H), 7.24 (dd, J=7.5, 1 Hz, 1H), 6.94 (dd, J=8, 7.5 Hz, 1H), 4.29 (t, J=7 Hz, 2H), 2.70–2.87 (m, 2H), 2.56–2.75 (m, 4H), 0.96 (t, J=7 Hz, 6H).

Example 29

5-Bromo-1-(2-diethylaminoethyl)-3-hydroxy-3-(2-fluorophenyl)oxindole

This compound was prepared by the same procedure as described in example 1, using the compound of reference example 14 in place of the compound of reference example 8 and using 1-bromo-2-fluorobenzene in place of 2-bromonaphthalene.

$^1$H NMR (CDCl$_3$, 270 MHz) δ 7.86 (td, J=8, 2 Hz, 1H), 7.43–7.49 (m, 1H), 7.43 (dd, J=8, 2 Hz, 1H), 7.23 (d, J=2 Hz, 1H), 6.94 (ddd, J=12, 8, 1 Hz, 1H), 6.84 (dd, J=8, 3 Hz, 1H), 3.73–3.93 (m, 2H), 2.68–2.76 (m, 2H), 2.62 (q, J=7 Hz, 2H), 2.61 (q, J=7 Hz, 2H), 1.03 (t, J=7 Hz, 6H).

Example 30

5-Bromo-1-(2-diethylaminoethyl)-3-hydroxy-3-(2-naphthyl)oxindole

This compound was prepared by the same procedure as described in example 1, using the compound of reference example 14 in place of the compound of reference example 8.

$^1$H NMR (CDCl$_3$, 270 MHz) δ 7.95 (d, J=2 Hz, 1H), 7.75–7.80 (m, 1H), 7.75 (d, J=8.5 Hz, 1H), 7.44–7.49 (m, 3H), 7.41 (d, J=2 Hz, 1H), 7.37 (d, J=2 Hz, 1H), 6.84 (d, J=8.5 Hz, 1H), 3.94 (dt, J=14, 7 Hz, 1H), 3.71 (dt, J=14, 7 Hz, 1H), 2.73 (t, J=7 Hz, 1H), 2.71 (t, J=7 Hz, 1H), 2.59 (q, J=7 Hz, 2H), 2.58 (q, J=7 Hz, 2H), 0.98 (t, J=7 Hz, 6H).

Example 31

5-Bromo-4-chloro-1-(2-diethylaminoethyl)-3-hydroxy-3-(2-naphthyl)oxindole

This compound was prepared by the same procedure as described in example 1, using the mixture of reference example 20 in place of the compound of reference example 8 and separated by silica gel chromatography (0.5% methanol in chloroform).

$^1$H NMR (CDCl$_3$, 270 MHz) δ 8.00 (d, J=1.5 Hz, 1H), 7.78–7.84 (m, 2H), 7.77 (d, J=8.5 Hz, 1H), 7.65 (d, J=8 Hz, 1H), 7.44–7.50 (m, 2H), 7.34 (dd, J=8.5, 2 Hz, 1H), 6.84 (d, J=8.5 Hz, 1H), 3.88 (dt, J=14, 6.5 Hz, 1H), 3.73 (dt, J=14, 6.5 Hz, 1H), 2.72 (t, J=6.5 Hz, 2H), 2.57 (q, J=7 Hz, 4H), 0.96 (t, J=7 Hz, 6H).

Example 32

5-Bromo-6-chloro-1-(2-diethylaminoethyl)-3-hydroxy-3-(2-naphthyl)oxindole

This compound was prepared by the same procedure as described in example 1, using the mixture of reference example 20 in place of the compound of reference example 8 and separated by silica gel chromatography (0.5% methanol in chloroform).

$^1$H NMR (CDCl$_3$, 270 MHz) δ 7.93 (d, J=1.5 Hz, 1H), 7.76–7.81 (m, 2H), 7.76 (d, J=8 Hz, 1H), 7.45–7.50 (m, 2H), 7.46 (s, 1H), 7.41 (dd, J=8.5, 2 Hz, 1H), 7.10 (s, 1H), 3.93 (dt, J=14, 6.5 Hz, 1H), 3.70 (dt, J=14, 6.5 Hz, 1H), 2.73 (t, J=6.5 Hz, 2H), 2.60 (q, J=7 Hz, 4H), 0.98 (t, J=7 Hz, 6H).

Example 33

4-Bromo-1-(2-dimethylaminoethyl)-3-hydroxy-3-(2-naphthyl)oxindole

This compound was prepared by the same procedure as described in example 1, using the compound of reference example 11 in place of the compound of reference example 8.

$^1$H NMR (CDCl$_3$, 270 MHz) δ 8.01 (d, J=1.7 Hz, 1H), 7.74–7.84 (m, 3H), 7.43–7.49 (m, 2H), 7.33 (dd, J=2.0, 8.6 Hz, 1H), 7.18–7.28 (m, 2H), 6.96 (dd, J=1.3, 7.3 Hz, 1H), 3.84 (t, J=6.7 Hz, 2H), 2.70 (dt, J=12.5, 6.7 Hz, 1H), 2.52 (dt, J=12.5, 6.7 Hz, 1H), 2.26 (s, 6H).

Example 34

4-Bromo-1-(2-dimethylaminoethyl)-3-hydroxy-3-(3,4-difluorophenyl)oxindole

This compound was prepared by the same procedure as described in example 1, using the compound of reference example 11 in place of the compound of reference example 8 and using 1-bromo-3,4-difluorobenzene in place of 2-bromonaphthalene.

$^1$H NMR (CDCl$_3$, 270 MHz) δ 7.18–7.35 (m, 3H), 7.07–7.15 (m, 2H), 6.90 (dd, J=1.5, 7.1 Hz, 1H), 3.73–3.90 (m, 2H), 2.69 (dt J=12.7, 6.4 Hz, 1H), 2.51 (dt J=12.7, 6.4 Hz, 1H), 2.24 (s, 6H).

Example 35

4-Bromo-1-(3-dimethylaminopropyl)-3-hydroxy-3-(2-naphthyl)oxindole

This compound was prepared by the same procedure as described in example 1, using the compound of reference example 12 in place of the compound of reference example 8.

$^1$H NMR (CDCl$_3$, 270 MHz) δ 8.00 (d, J=2.0 Hz, 1H), 7.75–7.85 (m, 3H), 7.43–7.49 (m, 2H), 7.18–7.29 (m, 3H), 6.99 (dd, J=1.3, 7.3 Hz, 1H), 3.76 (t, J=6.9 Hz, 2H), 2.25–2.49 (m, 2H), 2.19 (s, 6H), 1.82–1.93 (m, 2H).

Example 36

4-Bromo-1-(3-dimethylaminopropyl)-3-hydroxy-3-(3,4-difluorophenyl)oxindole

This compound was prepared by the same procedure as described in example 1, using the compound of reference example 12 in place of the compound of reference example 8 and using 1-bromo-3,4-difluorobenzene in place of 2-bromonaphthalene.

$^1$H NMR (CDCl$_3$, 270 MHz) δ 7.19–7.30 (m, 3H), 6.95–7.15 (m, 3H), 3.66–3.78 (m, 2H), 2.22–2.44 (m, 2H), 2.14 (s, 6H), 1.79–1.87 (m, 2H).

Example 37

4-Bromo-1-(2-diethylaminoethyl)-3-hydroxy-3-(3-fluorophenyl)oxindole

This compound was prepared by the same procedure as described in example 1, using 1-(2-diethylaminoethyl)-4-bromoisatin (reference example 10) in place of the compound of reference example 8 and using 1-bromo-3-fluorobenzene in place of 2-bromonaphthalene.

$^1$H NMR (CDCl$_3$, 270 MHz) δ 7.14–7.33 (m, 5H), 7.00 (dddd, J=1.5, 1.5, 8.4, 8.4 Hz, 1H), 6.93 (dd, J=1.3, 7.3 Hz, 1H), 3.87 (dt, J=13.7, 6.8 Hz, 1H), 3.71 (dt, J=13.7, 6.8 Hz, 1H), 2.70 (t, J=6.8 Hz, 2H), 2.55 (q, J=7.2 Hz, 4H), 0.95 (t, J=7.2 Hz, 6H).

Example 38

4-Bromo-1-(2-diethylaminoethyl)-3-hydroxy-3-(4-fluorophenyl)oxindole

This compound was prepared by the same procedure as described in example 1, using 1-(2-diethylaminoethyl)-4-bromoisatin (reference example 10) in place of the compound of reference example 8 and using 1-bromo-4-fluorobenzene in place of 2-bromonaphthalene.

$^1$H NMR (CDCl$_3$, 270 MHz) δ 7.34–7.42 (m, 2H), 7.18–7.26 (m, 2H), 6.90–7.07 (m, 3H), 3.83 (m, 2H), 2.57–2.73 (m, 6H), 0.88–1.09 (m, 6H).

Example 39

4-Bromo-1-(2-diethylaminoethyl)-3-hydroxy-3-(4-methoxyphenyl)oxindole

This compound was prepared by the same procedure as described in example 1, using 1-(2-diethylaminoethyl)-4-bromoisatin (reference example 10) in place of the compound of reference example 8 and using 1-bromo-4-methoxybenzene in place of 2-bromonaphthalene.

$^1$H NMR (CDCl$_3$, 270 MHz) δ 7.18–7.33 (m, 4H), 6.84–6.93 (m, 3H), 3.79 (s, 3H), 3.66–3.85 (m, 2H), 2.68 (t, J=7.1 Hz, 2H), 2.56 (q, J=7.2 Hz, 4H), 0.97 (t, J=7.2 Hz, 6H).

Example 40

4-Bromo-1-(2-diethylaminoethyl)-3-hydroxy-3-(3,4-difluorophenyl)oxindole

This compound was prepared by the same procedure as described in example 1, using 1-(2-diethylaminoethyl)-4-bromoisatin (reference example 10) in place of the compound of reference example 8 and using 1-bromo-3,4-difluorobenzene in place of 2-bromonaphthalene.

$^1$H NMR (CDCl$_3$, 270 MHz) δ 7.18–7.33 (m, 4H), 6.84–6.93 (m, 3H), 3.79 (s, 3H), 3.66–3.85 (m, 2H), 2.68 (t, J=7.1 Hz, 2H), 2.56 (q, J=7.2 Hz, 4H), 0.97 (t, J=7.2 Hz, 6H).

Example 41

4,6-Dichloro-1-(2-diethylaminoethyl)-3-hydroxy-3-(1-naphthyl)oxindole

This compound was prepared by the same procedure as described in example 1, using 1-bromonaphthalene in place of 2-bromonaphthalene.

$^1$H NMR (DMSO-d$_6$, 270 MHz: hydrochloride) δ 10.53 (brs, 1H), 8.2 (br, 1H), 7.93–7.96 (m, 2H), 7.18–7.68 (m, 6H), 4.25 (m, 2H), 3.26–3.52 (m, 6H), 1.20–1.24 (m, 6H).

Example 42

4,6-Dimethyl-1-(2-diethylaminoethyl)-3-hydroxy-3-(2-naphthyl)oxindole

This compound was prepared by the same procedure as described in example 1, using the compound of reference example 17 in place of the compound of reference example 8.

$^1$H NMR (DMSO-d$_6$, 270 MHz: hydrochloride) δ 10.61 (brs, 1H), 7.78–7.92 (m, 4H), 7.48–7.51 (m, 2H), 7.18 (d, J=8.61 Hz, 1H), 7.06 (s, 1H), 6.70 (m, 2H), 4.10 (m, 2H), 3.20–3.31 (m, 6H), 2.36 (s, 3H), 1.90 (s, 3H), 1.21 (t, J=6.6 Hz, 6H).

Example 43

4-Trifluoromethyl-1-(2-diethylaminoethyl)-3-hydroxy-3-(2-naphthyl)oxindole

This compound was prepared by the same procedure as described in example 1, using the compound of reference example 19 in place of the compound of reference example 8.

$^1$H NMR (DMSO-d$_6$, 270 MHz: hydrochloride) δ 10.38 (brs, 1H), 7.72–7.91 (m, 6H), 7.42–7.56 (m, 3H), 7.16 (d, J=6.9 Hz, 1H), 6.99 (s, 1H), 4.18 (t, J=6.6 Hz, 2H), 3.16–3.37 (m, 6H), 1.21 (t, J=6.9 Hz, 6H).

Example 44

4-Chloro-6-(4-hydroxy-1-butynyl)-1-(2-diethylaminoethyl)-3-hydroxy-3-(2-naphthyl)oxindole 4-Chloro-6-(4-t-butyldimethylsilyloxy-1-butynyl)-1-(2-diethylaminoethyl)-3-hydroxy-3-(2-naphthyl)oxindole was prepared as a mixture of regioisomers by the same procedure as described in example 1, using the mixture of reference example 22 in place of the compound of reference example 8. To a solution of this mixture (36 mg) in anhydrous acetonitrile (0.8 mL) was added aqueous 46% HF (0.1 mL) and the mixture stirred at room temperature for 3 hours. Saturated aqueous NaHCO$_3$ was then added and the mixture extracted with ethyl acetate. The organic phase was dried over anhydrous MgSO$_4$, and concentrated. Purification was carried out by silica gel chromatography (methanol:chloroform, 1:40 to 1:30 gradient) to give the title compound (4.9 mg).

$^1$H NMR (DMSO-d$_6$, 270 MHz: hydrochloride) δ 7.97 (s, 1H), 7.75–7.83 (m, 3H), 7.44–7.50 (m, 2H), 7.36 (dd, J=1.8, 8.7 Hz, 1H), 7.10 (d, J=1.2 Hz, 1H), 6.95 (d, J=1.2 Hz, 1H), 3.72–3.91 (m, 4H), 2.70–2.76 (m, 4H), 2.60 (q, J=7.1 Hz, 4H), 0.98 (t, J=7.1 Hz, 6H).

Example 45

4-Chloro-6-(3-hydroxy-1-propynyl)-1-(2-diethylaminoethyl)-3-hydroxy-3-(2-naphthyl)oxindole 4-Chloro-6-(3-t-butyldimethylsilyloxy-1-propynyl)-1-(2-diethylaminoethyl)-3-hydroxy-3-(2-naphthyl)oxindole was prepared as a mixture of regio-isomers by the same procedure as described in example 1, using the mixture of reference example 21 in place of the compound of reference example 8. The silyl group was removed by the same procedure as example 44, and separated by silica gel chromatography to give the title compound.

$^1$H NMR (DMSO-d$_6$, 270 MHz: hydrochloride) δ 7.99 (d, J=1.7 Hz, 1H), 7.75–7.84 (m, 3H), 7.44–7.50 (m, 2H), 7.36 (dd, J=1.8, 8.7 Hz, 1H), 7.11 (d, J=1.2 Hz, 1H), 6.96 (d, J=1.2 Hz, 1H), 4.50 (s, 2H), 3.83 (t, J=6.3 Hz, 2H), 2.71–2.85 (m, 2H), 2.65 (q, J=7.2 Hz, 4H), 0.99 (t, J=7.2 Hz, 6H).

Example 46

4,6-Dichloro-1-(2-diethylaminoethyl)-3-(diethylcarbamoylmethoxy)-3-(2-fluorophenyl)oxindole To a solution of the compound of example 6 (40.0 mg, 0.0973 mmol) in anhydrous THF (1.0 mL) was added potassium t-butoxide (18.7 mg, 0.167 mmol) and N,N-diethylchloroacetamide (27 μL, 0.197 mmol). The mixture was stirred at room temperature for 6 hours. H$_2$O and saturated aqueous NaHCO$_3$ was then added and the mixture extracted with ethyl acetate. The organic phase was dried over anhydrous MgSO$_4$ and concentrated. Purification by silica gel chromatography (methanol:chloroform, 1:40) to give the free compound (41.6 mg). Under nitrogen stream, to the free compound was added 4N HCl/dioxane solution (0.3 ml). After the solvent was evaporated, ether was added and the white solid formed was filtered to give the title compound (20.6 mg, 38%).

$^1$H NMR (DMSO-d$_6$, 270 MHz: hydrochloride) δ 10.41 (brs, 1H), 7.97 (ddd, J=1.8, 7.9, 7.9 Hz, 1H), 7.64 (d, J=1.5 Hz, 1H), 7.33–7.48 (m, 2H), 7.26 (d, J=1.5 Hz, 1H), 7.08–7.18 (m, 1H), 4.17–4.26 (m, 2H), 4.12 (s, 2H), 3.20–3.40 (m, 10H), 1.26 (t, J=7.1 Hz, 6H), 1.07 (t, J=6.8 Hz, 3H), 0.99 (t, J=7.1 Hz, 3H).

Example 47

4,6-Dichloro-3-(3-diethylaminopropyloxy)-3-(2-naphthyl)oxindole

To a solution of the compound of reference example 23 (41.0 mg) in diethylene glycol dimethyl ether (1 mL) was added 60% NaH (14.3 mg) and the mixture stirred at room temperature for one hour. To the mixture was added diethylaminopropyl chloride hydrochloride (22.2 mg) and the mixture stirred at 90° C. for 7 hours. After cooling, 1N HCl (1 mL) was added into it. The organic phase was dried over anhydrous MgSO$_4$ and concentrated. Purification was carried out by HPLC to give the title compound (28.8 mg).

$^1$H NMR (DMSO-d$_6$, 300 MHz: trifluoroacetate) δ 1.21 (t, J=7.1 Hz, 6H), 1.99 (m, 2H), 3.10–3.45 (m, 8H), 7.06 (d, J=1.8 Hz, 1H), 7.28 (d, J=1.7 Hz, 1H), 7.31 (dd, J=8.6, 1.8 Hz, 1H), 7.52 (m, 2H), 7.82–7.94 (m, 4H), 9.15 (brs, 1H), 11.24 (s, 1H).

Example 48

4-Trifluoromethyl-6-iodo-1-(2-diethylaminoethyl)-3-hydroxy-3-(2-naphthyl)oxindole This compound was prepared by the same procedure as described in example 1, using the compound of reference example 24 in place of the compound of reference example 8.

$^1$H NMR (CDCl$_3$, 270 MHz) δ 7.87 (d, J=1.8 Hz, 1H), 7.73–7.82 (m, 3H), 7.68 (s, 1H), 7.61 (s, 1H), 7.43–7.48 (m, 2H), 7.20 (dd, J=1.8, 8.7 Hz, 1H), 3.68–3.91 (m, 2H), 2.70 (t, J=5.8 Hz, 2H), 2.56 (q, J=7.0 Hz, 4H), 0.96 (t, J=7.0 Hz, 6H).

Example 49

4-Trifluoromethyl-6-(3-hydroxy-1-propynyl)-1-(2-diethylaminoethyl)-3-hydroxy-3-(2-naphthyl)oxindole 4-Trifluoromethyl-6-(3-t-butyldimethylsilyloxy-1-propynyl)-1-(2-diethylaminoethyl)-3-hydroxy-3-(2-naphthyl)oxindole was prepared by the same procedure as described in reference example 21, using the compound of example 48. The silyl group was removed by the same procedure as example 44, and separated by silica gel chromatography to give the title compound.

$^1$H NMR (DMSO-d$_6$, 270 MHz: hydrochloride) δ 10.21 (brs, 1H), 7.77–7.92 (m, 5H), 7.48–7.52 (m, 2H), 7.42 (s, 1H), 7.18–7.25 (m, 1H), 7.04 (s, 1H), 5.46 (brs, 1H), 4.39 (s, 2H), 4.17 (m, 2H), 3.20–3.37 (m, 6H), 1.20 (t, J=6.9 Hz, 6H).

Example 50

4-Chloro-6-(4-hydroxybutyl)-1-(2-diethylaminoethyl)-3-hydroxy-3-(2-naphthyl)oxindole Under nitrogen stream, to a solution of 4-chloro-6-(4-hydroxy-1-butynyl)-1-(2-diethylaminoethyl)-3-hydroxy-3-(2-naphthyl)oxindole (8.6 mg, 0.0180 mmol) in methanol (1.5 mL) was added 10% palladium/carbon (4.0 mg). The mixture was stirred under hydrogen atmosphere at room temperature for one hour. After filtration with Celite, the solvent was removed to give the title compound (8.7 mg).

$^1$H NMR (DMSO-d$_6$: hydrochloride) δ 10.50 (brs, 1H), 7.80–7.93 (m, 4H), 7.48–7.52 (m, 2H), 7.18–7.28 (m, 2H), 6.94 (s, 1H), 6.86 (s, 1H), 4.13–4.18 (m, 2H), 3.45 (t, J=6.4 Hz, 2H), 3.21–3.40 (m, 6H), 2.67 (t, J=7.8 Hz, 2H), 1.64–1.72 (m, 2H), 1.46–1.54 (m, 2H), 1.22 (t, J=7.1 Hz, 6H).

The structures of the compounds obtained in Examples 1 to 50 are shown below.

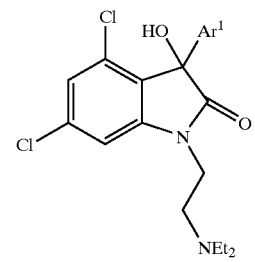

Example 1: Ar$^1$ = 2-naphthyl
Example 2: Ar$^1$ = 3-fluorophenyl
Example 3: Ar$^1$ = 4-fluorophenyl
Example 4: Ar$^1$ = 4-methoxyphenyl
Example 5: Ar$^1$ = 3, 4-difluorophenyl
Example 6: Ar$^1$ = 2-fluorophenyl
Example 7: Ar$^1$ = 2-chlorophenyl
Example 8: Ar$^1$ = 2-trifluoromethylphenyl
Example 9: Ar$^1$ = 3, 4-dichlorophenyl
Example 10: Ar$^1$ = 2-dimethylaminosulfonylphenyl

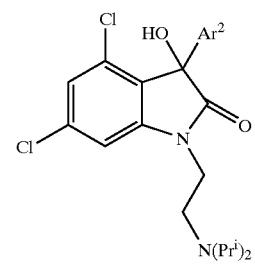

Example 11: Ar$^2$ = 2-naphthyl
Example 12: Ar$^2$ = 2-chlorophenyl
Example 13: Ar$^2$ = 2-trifluoromethylphenyl
Example 14: Ar$^2$ = 2-dimethylaminosulfonylphenyl
Example 15: Ar$^2$ = 3, 4-dichlorophenyl -continued

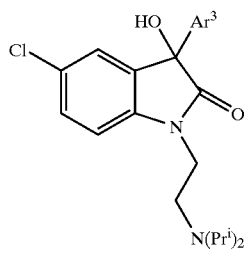

Example 16: Ar³ = 2-naphthyl
Example 17: Ar³ = 2-methoxyphenyl

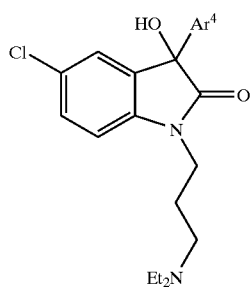

Example 18: Ar⁴ = 2-fluorophenyl
Example 19: Ar⁴ = 2-methoxyphenyl
Example 20: Ar⁴ = 2-naphthyl

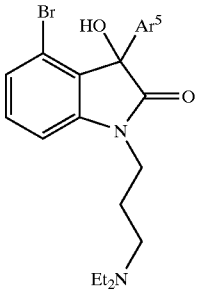

Example 21: Ar⁵ = 2-fluorophenyl
Example 22: Ar⁵ = 2-methoxyphenyl
Example 23: Ar⁵ = 2-naphthyl
Example 24: Ar⁵ = 4-biphenyl
Example 37: Ar⁵ = 3-fluorophenyl
Example 38: Ar⁵ = 4-fluorophenyl
Example 39: Ar⁵ = 4-methoxyphenyl
Example 40: Ar⁵ = 3, 4-difluorophenyl

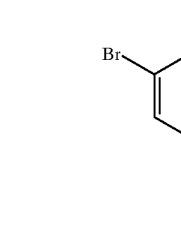

Example 26: Ar⁶ = 2-fluorophenyl
Example 27: Ar⁶ = 2-naphthyl
Example 28: Ar⁶ = 4-biphenyl

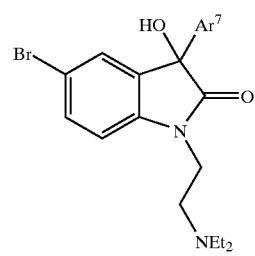

Example 29: Ar⁷ = 2-fluorophenyl
Example 30: Ar⁷ = 2-naphthyl

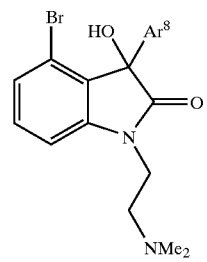

Example 33: Ar⁸ = 2-naphthyl
Example 34: Ar⁸ = 3, 4-difluorophenyl

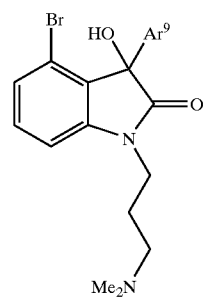

Example 35: Ar⁹ = 2-naphthyl
Example 36: Ar⁹ = 3, 4-difluorophenyl

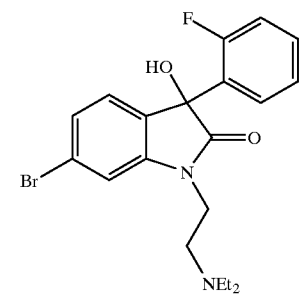

Example 25

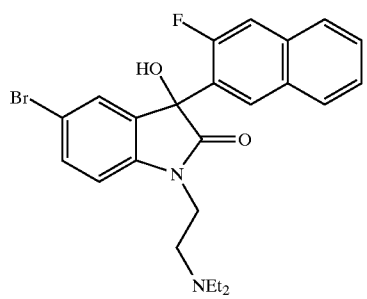

Example 30

-continued
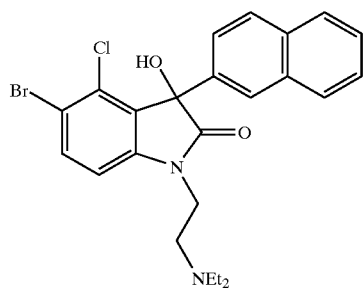
Example 31
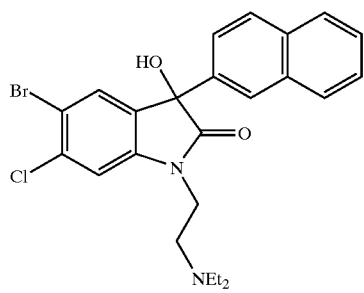
Example 32
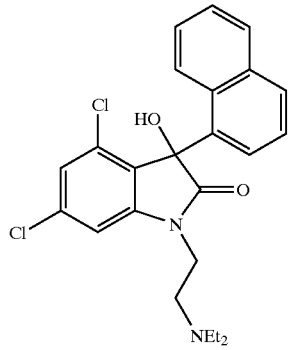
Example 41
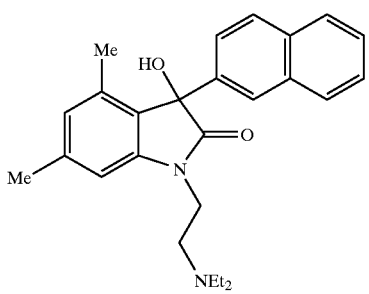
Example 42
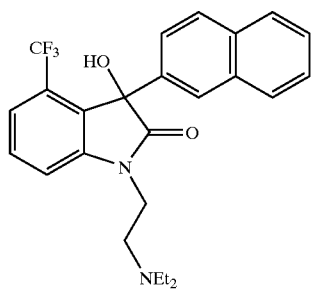
Example 43
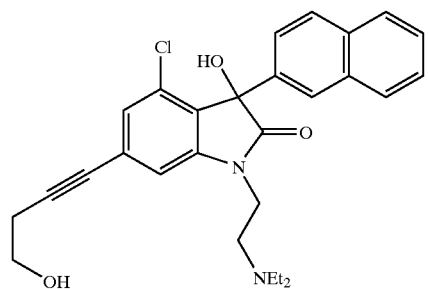
Example 44
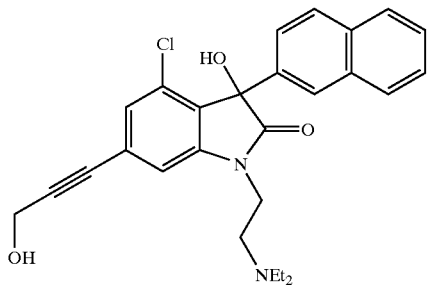
Example 45
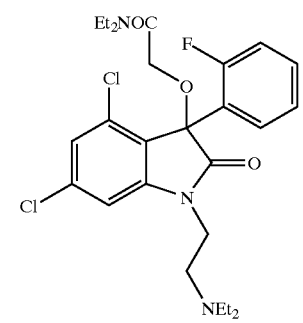
Example 46

-continued

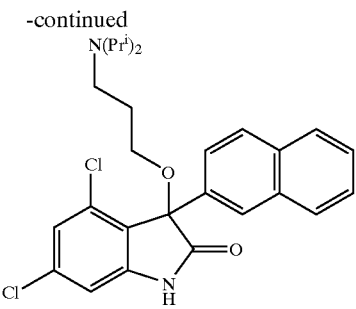

Example 31

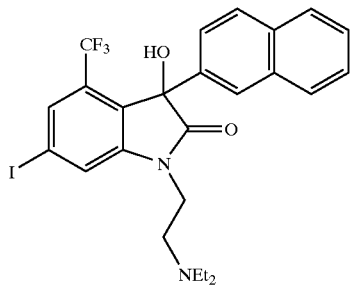

Example 48

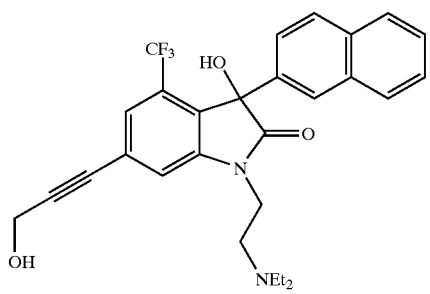

Example 49

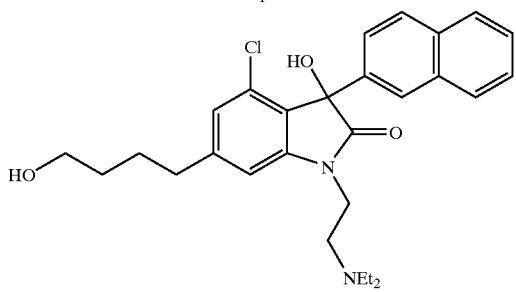

Example 50

Example 51

1-(2-Diethylaminoethyl)-4-trifluoromethyl-6-(4-morpholinocarbonyl-1-butynyl)-3-hydroxy-3-(2-naphthyl)oxindole (1) Morpholinocarbonyl-1-butyne A mixture of 4-pentynoic acid (210 mg, 2.14 mmol), morpholine hydrochloride (265 mg, 2.14 mmol), 1-hydroxybenzotriazol (338 mg, 2.50 mmol), WSC HCl (484 mg, 2.52 mmol), and triethylamine (0.37 ml, 2.65 mmol) in DMF (7 mL) was stirred for 1 h at room temperature. Water was added. The mixture was extracted with ethyl acetate-toluene, and the extracts were washed with water, dried over $MgSO_4$, and concentrated. The residue was purified by silica gel column chromatography with 1:1 to 1:5 hexane/ethyl acetate to give the title compound (325 mg, 91%).

$^1$H-NMR (CDCl$_3$) δ 3.64–3.70 (m, 6H), 3.48–3.50 (m, 2H), 2.56 (s, 2H), 2.56 (s, 2H), 1.97 (s, 1H).

(2) 1-(2-Diethylaminoethyl)-4-trifluoromethyl-6-(4-morpholinocarbonyl-1-butynyl)-3-hydroxy-3-(2-naphthyl) oxindole The title compound (26.1 mg) was prepared from 1-(2-diethylaminoethyl)-4-trifluoromethyl-6-iodo-3-hydroxy-3-(2-naphthyl)oxindole of Example 48 (35 mg, 0.0616 mmol) and 4-morpholinocarbonyl-1-butyne by the procedure similar to that described in Reference Example 21. The hydrochloride of the title compound was obtained by treating with 4 N HCl in dioxane followed by concentration to dryness.

$^1$H-NMR (DMSO-d$_6$: hydrochloride) δ 10.31 (brs, 1H), 7.79–7.91 (m, 4H), 7.73 (s, 1H), 7.48–7.51 (m, 2H), 7.36 (s, 1H), 7.17–7.25 (m, 1H), 7.03 (s, 1H), 4.17 (m, 2H), 3.08–3.57 (m, 14H), 2.71 (s, 4H), 1.20 (t, 6H, J=7.1 Hz).

Example 52

1-(2-Diethylaminoethyl)-4-trifluoromethyl-6-(3-dimethylamino-1-propynyl)-3-hydroxy-3-(2-naphthyl)oxindole The title compound (18.0 mg) was prepared from 1-(2-diethylaminoethyl)-4-trifluoromethyl-6-iodo-3-hydroxy-3-(2-naphthyl)oxindole of Example 48 (40.1 mg, 0.0706 mmol) and 3-dimethylamino-1-propyne by the procedure similar to that described in Reference Example 21. The hydrochloride of the title compound was obtained by treating with 4 N HCl in dioxane followed by concentration to dryness.

$^1$H-NMR (DMSO-d$_6$, 270 MHz: hydrochloride) δ 11.05 (brs, 1H), 10.76 (brs, 1H), 8.02 (s, 1H), 7.79–7.92 (m, 4H), 7.61 (s, 1H), 7.48–7.52 (m, 2H), 7.20 (d, 1H, J=10.2 Hz), 7.10 (s, 1H), 4.40 (s, 2H), 4.21–4.23 (m, 2H), 3.18–3.38 (m, 6H), 2.91 (s, 6H), 1.21 (t, 6H, J=7.3 Hz).

Example 53

1-(2-Diethylaminoethyl)-4-trifluoromethyl-6-(4-diethylcarbamoyl-1-butynyl)-3-hydroxy-3-(2-naphthyl)oxindole (1) 4-Diethylcarbamoyl-1-butyne The title compound (370 mg, 95%) was prepared from 4-pentynoic acid (250 mg, 2.55 mmol) and diethylamine hydrochloride (310 mg, 2.83 mmol) by the procedure similar to that described in Example 51(1).

$^1$H-NMR (CDCl$_3$) δ 3.39 (q, 2H, J=6.8 Hz), 3.31 (q, 2H, J=6.8 Hz), 2.56 (s, 2H), 2.55 (s, 2H), 1.96 (s, 1H), 1.19 (t, 3H, J=6.8 Hz), 1.12 (t, 3H, J=6.8 Hz).

(2) 1-(2-Diethylaminoethyl)-4-trifluoromethyl-6-(4-diethylcarbamoyl-1-butynyl)-3-hydroxy-3-(2-naphthyl) oxindole The title compound (28.9 mg) was prepared from 1-(2-diethylaminoethyl)-4-trifluoromethyl-6-iodo-3-hydroxy-3-(2-naphthyl)oxindole of Example 48 (40.5 mg, 0.0713 mmol) and 4-diethylcarbamoyl-1-butyne by the procedure similar to that described in Reference Example 21. The hydrochloride of the title compound was obtained by treating with 4 N HCl in dioxane followed by concentration to dryness.

$^1$H-NMR (DMSO-d$_6$, 270 MHz: hydrochloride) δ 10.28 (brs, 1H), 7.79–7.91 (m, 4H), 7.72 (s, 1H), 7.48–7.51 (m, 2H), 7.35 (s, 1H), 7.17 (d, 1H, J=8.9 Hz), 7.03 (s, 1H), 4.16 (m, 2H), 3.17–3.37 (m, 6H), 2.63–2.72 (m, 4H), 1.19 (t, 6H, J=7.8 Hz), 1.14 (t, 3H, J=7.1 Hz), 1.03 (t, 3H, J=7.1 Hz).

Example 54

1-(2-Diethylaminoethyl)-4-trifluoromethyl-6-(4-carboxy-1-butynyl)-3-hydroxy-3-(2-naphthyl) oxindole (1) 1-(2-Diethylaminoethyl)-4-trifluoromethyl-6-(4-t-butoxycarbonyl-1-butynyl)-3-hydroxy-3-(2-naphthyl)oxindole The title compound (34.9 mg, 82%) was prepared from 1-(2-diethylaminoethyl)-4-trifluoromethyl-6-iodo-3-hydroxy-3-(2-naphthyl)oxindole of Example 48 (40.9 mg, 0.0720 mmol) and 4-t-butoxycarbonyl-1-butyne by the procedure similar to that described in Reference Example 21.

$^1$H-NMR (CDCl$_3$) δ 7.87 (s, 1H), 7.71–7.81 (m, 3H), 7.42–7.48 (m, 2H), 7.3 (s, 1H), 7.19–7.23 (m, 2H), 3.69–3.92 (m, 2H), 2.68–2.76 (m, 4H), 2.51–2.60 (m, 6H), 1.49 (s, 9H), 0.95 (t, 6H, J=7.1 Hz).

(2) 1-(2-Diethylaminoethyl)-4-trifluoromethyl-6-(4-carboxy-1-butynyl)-3-hydroxy-3-(2-naphthyl)oxindole Treating 1-(2-diethylaminoethyl)-4-trifluoromethyl-6-(4-t-butoxycarbonyl-1-butynyl)-3-hydroxy-3-(2-naphthyl) oxindole (25.5 mg, 0.0429 mmol) with 4 N HCl in dioxane (1 mL) at 50° C. for 2 h followed by evaporation of the solvent to dryness gave the title compound (19.7 mg, 80%).

$^1$H-NMR (DMSO-d$_6$) δ 12.37 (brs, 1H), 10.28 (brs, 1H), 7.79–7.98 (m, 4H), 7.72 (s, 1H), 7.48–7.51 (m, 2H), 7.34–7.37 (m, 1H), 7.17–7.21 (m, 1H), 7.04 (s, 1H), 4.08–4.21 (m, 2H), 3.09–3.44 (m, 6H), 2.69–2.78 (m, 2H), 2.55–2.61 (m, 2H), 1.19 (t, 6H, J=6.9 Hz).

Example 55

1-(2-Diethylaminoethyl)-4-trifluoromethyl-6-cyano-3-hydroxy-3-(2-naphthyl)oxindole A mixture of 1-(2-diethylaminoethyl)-4-trifluoromethyl-6-iodo-3-hydroxy-3-(2-naphthyl)oxindole of Example 48 (582 mg, 1, 24 mmol), 60% Zn(CN)$_2$ (172 mg, 0.879 mmol), and (PPh$_3$)$_4$Pd (177 mg, 0.153 mmol) in DMF (6 mL) was stirred for 2.5 h at 80° C. Sat. aqueous NaHCO$_3$ was added. The mixture was extracted with toluene-ethyl acetate, and the extracts were washed with sat. aq. NaHCO$_3$, dried over MgSO$_4$, and concentrated. The residue was purified by silica gel column chromatography with 80:1 to 50:1 chloroform/methanol to give the title compound (382 mg, 66%).

$^1$H-NMR (CDCl$_3$) δ 7.86 (d, 1H, J=2.0 Hz), 7.74–7.82 (m, 3H), 7.64 (s, 1H), 7.45–7.50 (m, 3H), 7.18 (dd, 1H, J=2.0, 8.7 Hz), 3.75–3.93 (m, 2H), 2.73 (t, 2H, J=6.3 Hz), 2.49–2.63 (m, 4H), 0.95 (t, 6H, J=7.1 Hz).

Example 56

1-(2-Diethylaminoethyl)-4-trifluoromethyl-6-carbamoyl-3-hydroxy-3-(2-naphthyl)oxindole To a solution of 1-(2-diethylaminoethyl)-4-trifluoromethyl-6-cyano-3-hydroxy-3-(2-naphthyl)oxindole of Example 55 (185 mg, 0.396 mmol) in t-butanol (8 mL) was added powdered KOH (ca. 1 g) at 50° C. The mixture was stirred for 1 h at 50° C. and passed through a celite pad. The celite was washed with THF and the filtrate was concentrated. The residue was dispersed between water and ethyl acetate and the organic layer was separated. The organic layer was dried over MgSO$_4$ and concentrated to give the title compound (198 mg, quant.). The hydrochloride of the title compound was obtained by treating with 4 N HCl in dioxane followed by concentration to dryness.

$^1$H-NMR (DMSO-d$_6$: hydrochloride) δ 10.06 (brs, 1H), 8.36 (brs, 1H), 8.20 (s, 1H), 7.79–7.93 (m, 5H), 7.48–7.53 (m, 2H), 7.20 (dd, 1H, J=1.3, 8.3 Hz), 7.08 (s, 1H), 4.19 (m, 2H), 3.14–3.36 (m, 6H), 1.20 (t, 6H, J=7.9 Hz).

Example 57

3-Diethylaminopropyloxy-4-trifluoromethyl-6-(3-hydroxy-1-propynyl)-3-(2-naphthyl)oxindole (1) 5-iodo-2-Methyl-3-nitrobenzotrifluoride To H$_2$SO$_4$ (110 mL, 96%) stirring under a nitrogen atmosphere at 0–5° C. was added N-iodosuccinimide (41.13 g, 1.5 eq). The resulting black/dark red mixture was stirred at 0–5° C. for 40 minutes. To this was added dropwise commercially available 2-methyl-3-nitrobenzotrifluoride (25.0 g, 121.9 mmol) in H$_2$SO$_4$ (75 mL). Once the addition was completed, ca. 1 hour, the mixture was stirred at 5–10° C. for 5 hours. The resulting mixture was poured into ice (600 mL) and extracted with EtOAc (400 mL, 3×200 mL). The extracts were combined, washed with saturated aqueous Na$_2$SO$_3$ (500 mL) and H$_2$O (400 mL). The organic phase was then dried (anhydrous MgSO$_4$). After filtration the solvent was removed in vacuo to give a dark oil. Purification was carried out by column chromatography (silica gel, eluting hexane) to give the title compound as a light yellow/green oil which solidified on standing (34.81 g, 86%).

$^1$H-NMR (CDCl$_3$, 270 MHz) δ 2.494 (3H, dd, J=1.65 and 1.65 Hz), 8.145 (1H, dd, J=1.3 and 0.7 Hz), 8.195 (1H, s).

(2) Methyl 3-[2-Nitro-4-iodo-6-(trifluoromethyl)phenyl]-2oxo-propanoate

Dimethyl oxalate (127.79 g, 5.0 eq) was added to sodium methylate (216.4 mL, 28%, 5.0 eq). The resulting mixture was stirred at room temperature for 1.5 hours. To the mixture was then added 5-iodo-2-methyl-3-nitrobenzotrifluoride (71.64 g, 216.4 mmol), dissolved in MeOH (216 mL). The dark red mixture was then stirred at room temperature for 6 hours and left over night. The solvent was removed in vacuo to give a red solid which was subsequently added to aqueous 2.5N HCl (800 mL). The mixture was extracted with EtOAc (500 mL and 2×300 mL). The extracts were combined and dried (anhydrous MgSO$_4$). After filtration, the solvent was removed in vacuo to give a yellow solid of the crude product (161.41 g). A fraction of this was purified by column chromatography (silica gel, eluting 15:1 to 10:1 hexane:EtOAc) to give the title compound as a yellow solid.

$^1$H-NMR (CDCl$_3$, 270 MHz) δ 3.957 (3H, s), 4.624 (2H, s), 8.291 (1H, d, J=1.3 Hz), 8.544 (1H, d, J=2.0 Hz).

(3) [2-Nitro-4-iodo-6-(trifluoromethyl)phenyl]acetic Acid

To crude methyl 3-[2-nitro-4-iodo-6-(trifluoromethyl) phenyl]-2-oxo-propanoate prepared above (40.98 g) in AcOH (750 mL) was added aqueous 30% H$_2$O$_2$ solution (266 mL) followed by 70% HClO$_4$ (41 mL). The resulting mixture was stirred at 50° C. (bath temperature) for 4.5 hours. The solution was cooled and solid Na$_2$SO$_3$ (100 g) was added. The solvent was then removed in vacuo. The resulting orange solid was suspended in EtOAc (500 mL) and washed with H$_2$O (300 mL). The organic phase was then extracted with aqueous saturated NaHCO$_3$:aqueous 2N NaOH (6:1, 600 mL) followed by aqueous saturated NaHCO$_3$ (200 mL). The aqueous extracts were combined and cooled in an ice-water bath. The solution was then acidified with aqueous 35% HCl. The resulting solid was isolated by filtration and dried to give the title compound as a yellow solid (7.086 g). The organic phase was then re-extracted with aqueous saturated NaHCO$_3$ (6×50 mL).

The extracts were combined and cooled in an ice-water bath, and then acidified with aqueous 35% HCl. The resulting solid was isolated by filtration and dried to give the title compound as a yellow solid (6.896 g).

$^1$H-NMR (CDCl$_3$, 270 MHz) δ 4.162 (2H, s), 8.266 (1H, d, J=1.3 Hz), 8.509 (1H, d, J=1.65 Hz).

(4) Methyl [2-Nitro-4-iodo-6-(trifluoromethyl)phenyl] acetate

[2-Nitro-4-iodo-6-(trifluoromethyl)phenyl]acetic acid (34.7 g, 96.2 mmol) was dissolved in HCl/MeOH (300 mL) and the solution was heated at reflux for 4.5 hours. The solvent was removed in vacuo and the resulting oil was dissolved in EtOAc (400 mL). The solution was washed with saturated aqueous NaHCO$_3$ (60 mL, 100 mL and 80 mL) and then dried (anhydrous MgSO$_4$). After filtration, the solvent was removed in vacuo to yield the title compound (33.11 g, 92%).

$^1$H-NMR (CDCl$_3$, 270 MHz) δ 3.726 (3H, s), 4.109 (2H, s), 8.258 (1H, s), 8.486 (1H, d, J=1.65 Hz).

(5) 4-Trifluoromethyl-6-iodooxindole

To methyl [2-nitro-4-iodo-6-(trifluoromethyl)phenyl] acetate (33.11 g, 85.1 mmol) in MeOH (1000 mL) at 0° C. was added aqueous 20% TiCl$_3$ (815 g, 12.4 eq). The cooling bath was removed and the resulting mixture stirred at room temperature for 3 hours and then left overnight. To the mixture was then added aqueous 6N HCl (900 mL) and the mixture extracted with EtOAc:toluene (1:1, 3×1000 mL) and EtOAc:toluene (2:1, 3×900 mL and 3×500 mL). The extracts were combined and dried (anhydrous MgSO$_4$). After filtration, the solvent was removed in vacuo to give a light brown solid. Purification was carried out by crystallization from EtOH (300 mL) to give the title compound as a light brown crystalline solid (21.588 g, 78%).

$^1$H-NMR (CDCl$_3$, 270 MHz) δ 3.970 (2H, s), 7.387 (1H, s), 7.597 (1H, s), 7.930 (1H, brs).

(6) 3,3-Dibromo-4-trifluoromethyl-6-iodooxindole

To 4-trifluoromethyl-6-iodooxindole (21.00 g, 64.2 mmol) suspended in t-BuOH (610 mL) was added pyridinium bromide perbromide (91.32 g, 90%, 4.0 eq). The resulting mixture was stirred rapidly at room temperature for 4 hours. Water (1200 mL) was added and the mixture was stirred until all the solid material had dissolved. The red solution was then extracted with EtOAc (4×250 mL). The extracts were combined, washed with water (3×400 mL) and then dried (anhydrous MgSO$_4$). After filtration, the solvent was removed in vacuo to give the desired crude product as a light purple/grey solid (35.11 g).

$^1$H-NMR (DMSO-d$_6$, 270 MHz) δ 7.563 (1H, s), 7.780 (1H, s), 11.735 (1H, brs).

(7) 4-Trifluoromethyl-6-iodoisatin

The crude 3,3-dibromo-4-trifluoromethyl-6-iodooxindole (35.11 g) prepared above was dissolved in MeOH (1200 mL) and H$_2$O (300 mL) was added. The resulting mixture was heated at reflux for 3 hours and then aqueous 48% HBr (10 mL) was added. The solution was then heated at reflux for 27 hours. The MeOH solvent was removed in vacuo to give a brown/yellow solid. The solid was isolated by filtration, washing the collected solid with copious amounts of H$_2$O. The solid was then dried overnight in a vacuum desiccator (NaOH as desiccant) to give the desired isatin as a light brown solid (20.8214 g, 95% (two steps)).

$^1$H-NMR (DMSO-d$_6$, 270 MHz) δ 7.552 (1H, s), 7.680 (1H, s), 11.310 (1H, brs, NH).

(8) 4-Trifluoromethyl-6-iodo-3-hydroxy-3-(2-naphthyl) oxindole

The title compound (35.8 mg, 6.5%) was prepared from 4-trifluoromethyl-6-iodoisatin (400 mg, 1.17 mmol) and 2-naphthyl magnesium bromide by the procedure similar to that described in Example 1.

$^1$H-NMR (CDCl$_3$) δ 7.77–7.87 (m, 4H), 7.71 (s, 1H), 7.56 (s, 1H), 7.47–7.50 (m, 2H), 7.21–7.26 (m, 1H).

(9) 3-Diethylaminopropyloxy-4-trifluoromethyl-6-iodo-3-(2-naphthyl)oxindole

The title compound (13.9 mg, 33%) was prepared from 4-trifluoromethyl-6-iodo-3-hydroxy-(2-naphthyl)oxindole (34.5 mg, 0.0735 mmol) and 3-chloropropyl-N,N-diethylamine hydrochloride by the procedure similar to that described in Reference Example 8.

$^1$H-NMR (CDCl$_3$) δ 7.71–7.77 (m, 4H), 7.67 (s, 1H), 7.63 (s, 1H), 7.42–7.46 (m, 2H), 7.24 (d, 1H, J=10.2 Hz), 3.28–3.46 (m, 2H), 2.48–2.82 (m, 6H), 1.97–2.01 (m, 2H), 1.11 (t, 6H, J=6.8 Hz).

(10) 3-Diethylaminopropyloxy-4-trifluoromethyl-6-(3-hydroxy-1-propynyl)-3-(2-naphthyl)oxindole The title compound (3.7 mg, 34%) was prepared from 3-diethylaminopropyloxy-4-trifluoromethyl-6-iodo-3-(2-naphthyl)oxindole (12.4 mg, 0.0213 mmol) and 1-propyn-3-ol by the procedure similar to that described in Reference Example 21.

$^1$H-NMR (CDCl$_3$) δ 7.70–7.79 (m, 4H), 7.53 (s, 1H), 7.42–7.47 (m, 2H), 7.39 (s, 1H), 7.19 (d, 1H, J=8.3 Hz), 4.52 (s, 2H), 3.11–3.39 (m, 8H), 2.22–2.25 (m, 2H), 1.37 (t, 6H, J=7.4 Hz).

Example 58

1-(2-Diethylaminoethyl)-4-trifluoromethyl-6-morpholinocarbonyl-3-hydroxy-3-(2-naphthyl) oxindole A mixture of 1-(2-diethylaminoethyl)-4-trifluoromethyl-6-cyano-3-hydroxy-3-(2-naphthyl)oxindole (30 mg, 0.0642 mmol), conc. HCl (2 mL), and acetic acid (2 mL) was heated at reflux for 5 h. Excess solvents were azeotropically removed in vacuo by using toluene to give crude carboxylic acid. The residue was dissolved in DMF (0.5 mL) and morpholine hydrochloride (5.6 mg, 0.0453 mmol), 1-hydroxybenzotriazole (7.5 mg, 0.0555 mmol), WSC HCl (8.5 mg, 0.0443 mmol), and triethylamine (0.04 mL, 0.287 mmol) were added. The mixture was stirred for 16 h at room temperature and diluted with sat. aqueous NaHCO$_3$. The mixture was extracted with ethyl acetate-toluene and the extracts were washed with sat. aqueous NaHCO$_3$, dried over MgSO$_4$, and concentrated. The residue was purified by silica gel column chromatography with 30:1 to 25:1 chloroform/methanol to give the title compound (4.8 mg, 18%).

$^1$H-NMR (CDCl$_3$) δ 7.90 (s, 1H), 7.74–7.83 (m, 3H), 7.46–7.49 (m, 2H), 7.34 (s, 1H), 7.30 (s, 1H), 7.22 (dd, 1H, J=2.0, 8.6 Hz), 3.55–3.90 (m, 10H), 2.69–2.87 (m, 2H), 2.62 (q, 4H, J=7.1 Hz), 0.97 (t, 6H, J=7.1 Hz).

Example 59

1-(2-Diethylaminoethyl)-4-trifluoromethyl-7-(4-morpholinocarbonyl-1-butynyl)-3-hydroxy-3-(2-naphthyl)oxindole (1) 7-iodo-4-Trifluoromethylisatin A mixture of 4-trifluoromethylisatin (450 mg, 2.09 mmol) and N-iodosuccinimide (800 mg, 3.72 mmol) in conc. H$_2$SO$_4$ (5 mL) was stirred for 6 h at 40° C. and poured into crushed ice. The mixture was extracted with ethyl acetate and the extracts were washed with aqueous Na$_2$SO$_3$, dried over MgSO$_4$, and concentrated. The residue was purified by silica gel column chromatography with 3:1 hexane/ethyl acetate to give the title compound (296 mg, 42%).

¹H-NMR (DMSO-d₆) δ 11.24 (brs, 1H), 8.15 (d, 1H, J=8.4 Hz), 7.14 (d, 1H, J=8.4 Hz).

(2) 1-(2-Diethylaminoethyl)-7-iodo-4-trifluoromethylisatin

The title compound (245 mg, 76%) was prepared from 7-iodo-4-trifluoromethylisatin (250 mg, 0.733 mmol) and 2-chloroethyl-N,N-diethylamine hydrochloride by the procedure similar to that described in Reference Example 8.

¹H-NMR (CDCl₃) δ 8.15 (d, 1H, J=8.4 Hz), 7.09 (d, 1H, J=8.4 Hz), 4.40 (t, 2H, J=6.5 Hz), 2.60 (t, 2H, J=6.5 Hz), 2.45 (q, 4H, J=7.3 Hz), 0.82 (t, 6H, J=7.3 Hz).

(3) 1-(2-Diethylaminoethyl)-4-trifluoromethyl-7-iodo-3-hydroxy-3-(2-naphthyl)oxindole The title compound (103 mg, 53%) was prepared from 1-(2-diethylaminoethyl)-7-iodo-4-trifluoromethylisatin (152 mg, 0.345 mmol) and 2-naphthylmagnesium bromide by the procedure similar to that described in Example 1.

¹H-NMR (CDCl₃) δ 8.01 (d, 1H, J=8.2 Hz), 7.88 (s, 1H), 7.73–7.84 (m, 3H), 7.44–7.48 (m, 2H), 7.19 (dd, 1H, J=2.0, 8.6 Hz), 7.08 (d, 1H, J=8.2 Hz), 4.24–4.45 (m, 2H), 2.39–2.83 (m, 6H), 0.88 (t, 6H, J=7.1 Hz).

(4) 1-(2-Diethylaminoethyl)-4-trifluoromethyl-7-(4-morpholinocarbonyl-1-butynyl)-3-hydroxy-3-(2-naphthyl)oxindole The title compound (28.2 mg) was prepared from 1-(2-diethylaminoethyl)-4-trifluoromethyl-7-iodo-3-hydroxy-3-(2-naphthyl)oxindole (43.4 mg, 0.0764 mmol) and 4-morpholinocarbonyl-1-butyne by the procedure similar to that described in Reference Example 21. The hydrochloride of the title compound was obtained by treating with 4 N HCl in dioxane followed by concentration to dryness.

¹H-NMR (DMSO-d₆: hydrochloride) δ 10.19 (brs, 1H), 7.79–7.92 (m, 4H), 7.65 (d, 1H, J=8.2 Hz), 7.48–7.51 (m, 2H), 7.40 (d, 1H, J=8.2 Hz), 7.11–7.28 (m, 1H), 7.04 (s, 1H), 4.41–4.60 (m, 2H), 3.14–3.60 (m, 14H), 2.76–2.80 (m, 4H), 1.17–1.23 (m, 6H).

Example 60

(+) and (−)-1-(2-Diethylaminoethyl)-4-trifluoromethyl-6-(4-morpholinocarbonyl-1-butynyl)-3-hydroxy-3-(2-naphthyl)oxindole (Optical Isomers of the Compound of Example 51)

Racemic compound 1-(2-diethylaminoethyl)-4-trifluoromethyl-6-(4-morpholinocarbonyl-1-butynyl)-3-hydroxy-3-(2-naphthyl)oxindole of Example 51 was separated to (+)- and (−)-enantiomers by using a preparative HPLC on a Chiralpak OD™ with 80:20:1 hexane/isopropanol/diethylamine as the eluent. The enantiomeric excess was determined by using HPLC on a Chiralpak AD™ (250×4.6 mm) with 100:100:1 hexane/isopropanol/diethylamine as the eluent at the flow rate of 0.5 ml/min. Under these conditions, two enantiomers were eluted at the retention time of 11.2 and 18.7 min, respectively.

Example 61

1-(2-Diethylaminoethyl)-4-trifluoromethyl-6-(4-morpholinocarbonyl-1-butynyl)-3-amino-3-(2-naphthyl)oxindole (1) 1-(2-Diethylaminoethyl)-4-trifluoromethyl-6-iodo-3-amino-3-(2-naphthyl)oxindole A mixture of 1-(2-diethylaminoethyl)-4-trifluoromethyl-6-iodo-3-hydroxy-3-(2-naphthyl)oxindole of Example 48 (100 mg, 0.176 mmol) and thionyl chloride (2 mL) was stirred for 1.5 h at room temperature and the excess reagent was evaporated in vacuo to give the crude chloride. The residue was dissolved in DMF (1.5 mL) and triethylamine (0.06 mL, 0.43 mmol) and NaN₃ (27 mg, 0.415 mmol) were added. The mixture was stirred for 2.5 h at 70° C. Sat. aqueous NaHCO₃ was added. The mixture was extracted with ethyl acetate-toluene and the extracts were washed with sat. aqueous NaHCO₃, dried over MgSO₄, and concentrated to give the crude azide (100 mg, 96%). The crude azide (89 mg, 0.15 mmol) was dissolved in MeOH (1.5 mL) and SnCl₂-2 H₂O (58.5 mg, 0.259 mmol). The mixture was stirred for 1.5 h at room temperature and concentrated. To the residue was added sat. aqueous NaHCO₃ and ethyl acetate and the organic layer was separated. The layer was dried over MgSO₄ and concentrated. The residue was purified by silica gel column chromatography with 40:1 chloroform/methanol to give the title compound.

¹H-NMR (CDCl₃) δ 7.77–7.85 (m, 3H), 7.72 (d, 1H, J=8.7 Hz), 7.67 (s, 1H), 7.60 (s, 1H), 7.45–7.50 (m, 2H), 7.12 (dd, 1H, J=1.8, 8.7 Hz), 3.85–3.95 (m, 1H), 3.64–3.74 (m, 1H), 2.68 (t, 2H, J=6.6 Hz), 2.54 (q, 4H, J=7.1 Hz), 2.47 (brs, 2H), 0.96 (t, 6H, J=7.1 Hz).

(2) 1-(2-Diethylaminoethyl)-4-trifluoromethyl-6-(4-morpholinocarbonyl-1-butynyl)-3-amino-3-(2-naphthyl)oxindole The title compound (34.3 mg) was prepared from 1-(2-diethylaminoethyl)-4-trifluoromethyl-6-iodo-3-amino-3-(2-naphthyl)oxindole (36.3 mg, 0.0640 mmol) and 4-morpholinocarbonyl-1-butyne by the procedure similar to that described in Reference Example 21. The hydrochloride of the title compound was obtained by treating with 4 N HCl in dioxane followed by concentration to dryness.

¹H-NMR (DMSO-d₆: hydrochloride) δ 10.38 (brs, 1H), 7.89–7.95 (m, 5H), 7.57–7.60 (m, 2H), 7.49 (s, 1H), 7.15 (d, 1H, J=9.2 Hz), 4.15–4.39 (m, 2H), 3.19–3.57 (m, 14H), 2.72–2.75 (m, 4H), 1.22 (t, 6H, J=7.1 Hz).

Example 62

1-(2-Diethylaminoethyl)-4-trifluoromethyl-6-(4-morpholinocarbonyl-1-butynyl)-3-hydroxy-3-(2-fluorophenyl)oxindole (1) 1-(2-Diethylaminoethyl)-4-trifluoromethyl-6-iodo-3-hydroxy-3-(2-fluorophenyl)oxindole To a solution of 1-bromo-2-fluorobenzene (0.09 mL, 0.823 mmol) in THF (4 mL) was added dropwise 1.53 N BuLi in hexane (0.54 mL, 0.826 mmol) over 10 min at −78° C. and the mixture was stirred for 10 min. The resulting solution was then transferred into the cooled solution of 1-(2-diethylaminoethyl)-4-trifluoromethyl-6-iodoisatin (330 mg, 0.75 mmol) in THF (2 mL) at −78° C. via a cannula. The mixture was stirred for 30 min at the same temperature and the reaction was quenched with aqueous NaHCO₃. The mixture was extracted with ethyl acetate and the extracts were dried over MgSO₄ and concentrated. The residue was purified by silica gel column chromatography with 50:1 to 30:1 chloroform/methanol to give the title compound (35.9 mg, 9%).

¹H-NMR (CDCl₃) δ 7.88 (dd, 1H, J=7.1, 7.1 Hz), 7.60 (s, 1H), 7.56 (s, 1H), 7.21–7.35 (m, 2H), 6.89 (ddd, 1H, J=1.5, 8.1, 11.8 Hz), 3.75–3.95 (m, 2H), 2.54–2.83 (m, 6H), 1.03 (t, 6H, J=6.9 Hz).

(2) 1-(2-Diethylaminoethyl)-4-trifluoromethyl-6-(4-morpholinocarbonyl-1-butynyl)-3-hydroxy-3-(2-fluorophenyl)oxindole The title compound (19.2 mg) was prepared from 1-(2-diethylaminoethyl)-4-trifluoromethyl-6-iodo-3-hydroxy-3-(2-fluorophenyl)oxindole (27.4 mg, 0.0511 mmol) and 4-morpholinocarbonyl-1-butyne by the procedure similar to that described in Reference Example 21. The hydrochloride of the title compound was obtained by treating with 4 N HCl in dioxane followed by concentration to dryness.

¹H-NMR (DMSO-d₆: hydrochloride) δ 10.43 (brs, 1H), 7.91 (dd, 1H, J=7.3, 7.3 Hz), 7.68 (s, 1H), 7.14–7.38 (m, 4H), 7.01 (dd, 1H, J=8.3, 10.9 Hz), 4.10–4.30 (m, 2H), 3.24–3.63 (m, 14H), 2.69 (m, 4H), 1.24 (t, 6H, J=7.1 Hz).

Example 63

1-(2-Diethylaminoethyl)-4-trifluoromethyl-6-(4-morpholinocarbonyl-1-butynyl)-3-hydroxy-3-(2-trifluoromethylphenyl)oxindole (1) 1-(2-Diethylaminoethyl)-4-trifluoromethyl-6-iodo-3-hydroxy-3-(2-trifluoromethylphenyl)oxindole To a solution of 2-bromobenzotrifluoride (0.3 mL, 2.23 mmol) in THF (1.5 mL) was added dropwise 1.53 N BuLi in hexane (1.45 mL, 2.22 mmol) over 10 min at −78° C. and the mixture was stirred for 10 min. The resulting solution (1.2 mL, 0.82 mmol) was then added dropwise to the cooled solution of 1-(2-diethylaminoethyl)-4-trifluoromethyl-6-iodoisatin (352 mg, 0.8 mmol) in THF (4 mL) at −78° C. via a syringe. The mixture was allowed to warm to room temperature and stirred for 30 min. The reaction was quenched with aqueous NaHCO₃. The mixture was extracted with ethyl acetate, dried over MgSO₄, and concentrated. The residue was purified by silica gel column chromatography with 50:1 to 40:1 chloroform/methanol to give the title compound (96.3 mg, 21%).

¹H-NMR (CDCl₃) δ 8.44 (d, 1H, J=7.9 Hz), 7.60–7.74 (m, 3H), 7.45–7.53 (m, 2H), 4.01–4.08 (m, 1H), 3.60–3.70 (m, 1H), 2.50–2.87 (m, 6H), 1.01 (t, 6H, J=7.1 Hz).

(2) 1-(2-Diethylaminoethyl)-4-trifluoromethyl-6-(4-morpholinocarbonyl-1-butynyl)-3-hydroxy-3-(2-trifluoromethylphenyl)oxindole The title compound (22.1 mg) was prepared from 1-(2-diethylaminoethyl)-4-trifluoromethyl-6-iodo-3-hydroxy-3-(2-trifluoromethylphenyl)oxindole (25.2 mg, 0.043 mmol) and 4-morpholinocarbonyl-1-butyne by the procedure similar to that described in Reference Example 21. The hydrochloride of the title compound was obtained by treating with 4 N HCl in dioxane followed by concentration to dryness.

¹H-NMR (DMSO-d₆: hydrochloride) δ 10.27 (brs, 1H), 8.42 (d, 1H, J=7.7 Hz), 7.82 (dd, 1H, J=7.7, 7.7 Hz), 7.66–7.70 (m, 2H), 7.59 (dd, 1H, J=7.7, 7.7 Hz), 7.49 (s, 1H), 7.28 (s, 1H), 4.06–4.26 (m, 2H), 3.26–3.57 (m, 14H), 2.69–2.75 (m, 4H), 1.24 (t, 6H, J=6.9 Hz).

Example 64

1-(2-Diethylaminoethyl)-4-trifluoromethyl-6-cyano-3-hydroxy-3-(2-trifluoromethylphenyl)oxindole The title compound (26.1 mg, 63%) was prepared from 1-(2-diethylaminoethyl)-4-trifluoromethyl-6-iodo-3-hydroxy-3-(2-trifluoromethylphenyl)oxindole (49.8 mg, 0.0849 mmol) by the procedure similar to that described in Example 55.

¹H-NMR (CDCl₃) δ 8.47 (d, 1H, J=7.8 Hz), 7.73 (dd, 1H, J=7.8, 7.8 Hz), 7.65 (d, 1H, J=7.8 Hz), 7.57 (s, 1H), 7.51 (dd, 1H, J=7.8, 7.8 Hz), 7.42 (s, 1H), 4.11–4.22 (m, 1H), 3.60–3.70 (m, 1H), 2.82–2.93 (m, 1H), 2.51–2.74 (m, 5H), 1.00 (t, 6H, J=7.1 Hz).

Example 65

1-(2-Diethylaminoethyl)-4-trifluoromethyl-6-(4-carbamoyl-1-butynyl)-3-hydroxy-3-(2-naphthyl)oxindole (1) 4-Carbamoyl-1-butyne A mixture of 4-pentynoic acid (189 mg, 1.93 mmol) and thionyl chloride (1.5 mL) was heated at reflux for 1 h and the excess reagent was evaporated off. The residue was dissolved in THF (5 mL) and added dropwise to the ice-cooled conc. aqueous ammonia (5 mL). The mixture was stirred for 2 h at room temperature, acidified by adding hydrochloric acid, and extracted with ethyl acetate. The organic layers were dried over MgSO₄ and concentrated. The residue was purified by silica gel column chromatography with ethyl acetate to give the title compound (61.1 mg, 33%).

¹H-NMR (CDCl₃) δ 5.61 (brs, 2H), 2.43–2.58 (m, 4H), 2.03 (s, 1H).

(2) 1-(2-Diethylaminoethyl)-4-trifluoromethyl-6-(4-carbamoyl-1-butynyl)-3-hydroxy-3-(2-naphthyl)oxindole The title compound (28.9 mg) was prepared from 1-(2-diethylaminoethyl)-4-trifluoromethyl-6-iodo-3-hydroxy-3-(2-naphthyl)oxindole of Example 48 (50.1 mg, 0.0881 mmol) and 4-carbamoyl-1-butyne by the procedure similar to that described in Reference Example 21. The hydrochloride of the title compound was obtained by treating with 4 N HCl in dioxane followed by concentration to dryness.

¹H-NMR (DMSO-d₆: hydrochloride) δ 10.01 (brs, 1H), 7.79–7.94 (m, 4H), 7.71 (s, 1H), 7.47–7.53 (m, 2H), 7.44 (brs, 1H), 7.37 (s, 1H), 7.14–7.28 (m, 1H), 7.03 (brs, 1H), 6.94 (brs, 1H), 4.12–4.19 (m, 2H), 3.13–3.50 (m, 6H), 2.69 (t, 2H, J=7.3 Hz), 2.40 (t, 2H, J=7.3 Hz), 1.19 (t, 6H, J=7.3 Hz).

Example 66

1-(2-Diethylaminoethyl)-4-trifluoromethyl-6-(3-amino-1-propynyl)-3-hydroxy-3-(2-naphthyl)oxindole (1) 1-(2-Diethylaminoethyl)-4-trifluoromethyl-6-(3-t-butoxycarbonylamino-1-propynyl)-3-hydroxy-3-(2-naphthyl)oxindole The title compound (170 mg, 83%) was prepared from 1-(2-diethylaminoethyl)-4-trifluoromethyl-6-iodo-3-hydroxy-3-(2-naphthyl)oxindole of Example 48 (195 mg, 0.343 mmol) and 3-t-butoxycarbonylamino-1-propyne by the procedure similar to that described in Reference Example 21.

¹H-NMR (CDCl₃) δ 7.88 (s, 1H), 7.72–7.82 (m, 3H), 7.43–7.49 (m, 2H), 7.4 (s, 1H), 7.24 (s, 1H), 7.21 (dd, 1H, J=2.0, 8.9 Hz), 4.84 (brs, 1H), 4.20 (d, 2H, J=5.6 Hz), 3.76–3.91 (m, 2H), 2.66–2.79 (m, 2H), 2.50–2.64 (m, 4H), 1.49 (s, 9H), 0.95 (t, 6H, J=7.1 Hz).

(2) 1-(2-Diethylaminoethyl)-4-trifluoromethyl-6-(3-amino-1-propynyl)-3-hydroxy-3-(2-naphthyl)oxindole The hydrochloride of the title compound was obtained by treating 1-(2-diethylaminoethyl)1-4-trifluoromethyl-6-(3-t-butoxycarbonylamino-1-propynyl)-3-hydroxy-3-(2-naphthyl)oxindole with 4 N HCl in dioxane at 50° C. for 1.5 h followed by concentration to dryness.

¹H-NMR (DMSO-d₆) δ 10.63 (brs, 1H), 8.53 (brs, 3H), 7.79–7.99 (m, 5H), 7.47–7.56 (m, 2H), 7.44 (s, 1H), 7.11–7.25 (m, 1H), 7.10 (s, 1H), 4.12–4.28 (m, 2H), 4.08 (m, 2H), 3.13–3.39 (m, 6H), 1.21 (t, 6H, J=7.1 Hz).

Example 67

1-(2-Diethylaminoethyl)-4-trifluoromethyl-6-[3-(N-ethylureido)-1-propynyl]-3-hydroxy-3-(2-naphthyl)oxindole A mixture of 1-(2-diethylaminoethyl)-4-trifluoromethyl-6-(3-amino-1-propynyl)-3-hydroxy-3-(2-naphthyl)oxindole (40 mg, 0.074 mmol), ethyl isocyanate (0.0065 mL, 0.0821 mmol), and triethylamine (0.025 mL, 0.0821 mmol) in THF (0.5 mL) was stirred for 4 h at room temperature and the reaction was quenched with sat. aqueous NaHCO₃. The mixture was extracted with ethyl acetate and the extracts were dried over MgSO₄ and concentrated. The residue was purified by column chromatography with 40:1 to 20:1 chloroform/methanol to give the title compound (20.6 mg). The hydrochloride of the title compound was obtained by treating with 4 N HCl in dioxane followed by concentration to dryness.

¹H-NMR (DMSO-d₆: hydrochloride) δ 10.21 (brs, 1H), 7.79–7.96 (m, 4H), 7.74 (s, 1H), 7.47–7.56 (m, 2H), 7.39 (s, 1H), 7.14–7.28 (m, 1H), 7.05 (brs, 1H), 6.35 (brs, 1H), 6.08 (brs, 1H), 4.13–4.18 (m, 4H), 3.17–3.41 (m, 6H), 3.04 (q, 2H, J=7.1 Hz), 1.19 (t, 6H, J=6.9 Hz), 1.01 (t, 3H, J=7.1 Hz).

Example 68

1-(2-Diethylaminoethyl)-4-trifluoromethyl-6-(3-methansulfonylamino-1-propynyl)-3-hydroxy-3-(2-naphthyl)oxindole The title compound (26.3 mg) was prepared from 1-(2-diethylaminoethyl)-4-trifluoromethyl-6-(3-amino-1-propynyl)-3-hydroxy-3-(2-naphthyl)oxindole (40 mg, 0.0704 mmol) and methanesulfonyl chloride by the procedure similar to that described in Example 67. The hydrochloride of the title compound was obtained by treating with 4 N HCl in dioxane followed by concentration to dryness.

¹H-NMR (DMSO-d₆: hydrochloride) δ 10.24 (brs, 1H), 7.79–7.92 (m, 5H), 7.74 (t, 1H, J=6.1 Hz), 7.48–7.52 (m, 2H), 7.45 (s, 1H), 7.18–7.25 (m, 1H), 5 7.07 (s, 1H), 4.14–4.16 (m, 4H), 3.18–3.33 (m, 6H), 3.07 (s, 3H), 1.20 (t, 6H, J=7.1 Hz).

Example 69

1-(2-Diethylaminoethyl)-4-trifluoromethyl-6-[4-(N-hydroxyethylcarbamoyl)-1-butynyl]-3-hydroxy-3-(2-naphthyl)oxindole N-Hydroxyethyl-4-pentynamide (128 mg, 45%) was prepared from 4-pentynoic acid (200 mg, 2.03 mmol) and 2-ethanolamine by the procedure similar to that described in Example 65(1). The title compound (34.2 mg) was prepared from 1-(2-diethylaminoethyl)-4-trifluoromethyl-6-iodo-3-hydroxy-3-(2-naphthyl)oxindole of Example 48 (50.4 mg, 0.0887 mmol) and N-hydroxyethyl-4-pentynamide by the procedure similar to that described in Reference Example 21. The hydrochloride of the title compound was obtained by treating with 4 N HCl in dioxane followed by concentration to dryness.

¹H-NMR (DMSO-d₆: hydrochloride) δ 10.27 (brs, 1H), 8.03 (m, 1H), 7.78–7.92 (m, 4H), 7.72 (s, 1H), 7.48–7.51 (m, 2H), 7.37 (s, 1H), 7.14–7.28 (m, 1H), 7.04 (brs, 1H), 4.16 (m, 2H), 3.72 (m, 2H), 3.12–3.44 (m, 8H), 2.70 (t, 2H, J=7.3 Hz), 2.43 (t, 2H, J=7.3 Hz), 1.19 (t, 6H, J=6.8 Hz).

Example 70

1-(2-Diethylaminoethyl)-4-trifluoromethyl-6-(4-morpholinocarbonyl-1-butynyl)-3-hydroxy-3-(2-chlorophenyl)oxindole (1) 1-(2-Diethylaminoethyl)-4-trifluoromethyl-6-iodo-3-hydroxy-3-(2-chlorophenyl)oxindole To a solution of 1-(2-diethylaminoethyl)-4-trifluoromethyl-6-iodoisatin (4 g, 9.09 mmol) in a mixture of diethyl ether (60 mL) and toluene (20 mL) was added dropwise a freshly prepared 0.67 N 2-chlorophenylmagnesium iodide in ether (15 mL, 10.1 mmol) over 20 min at room temperature. The mixture was stirred for 20 min at the same temperature and the reaction was quenched with aqueous NaHCO₃. The mixture was extracted with ethyl acetate and the extracts were washed with sat. aqueous NaHCO₃, dried over MgSO₄, and concentrated. The residue was purified by silica gel column chromatography with 100:1 to 50:1 chloroform/methanol to give the title compound (2.81 g, 56%).

¹H-NMR (CDCl₃) δ 8.09 (d, 1H, J=6.8 Hz), 7.61 (s, 1H), 7.53 (s, 1H), 7.41 (dd, 1H, J=6.8, 6.8 Hz), 7.21–7.32 (m, 2H), 3.97–4.11 (m, 1H), 3.68–3.78 (m, 1H), 2.55–2.84 (m, 6H), 1.03 (t, 6H, J=7.1 Hz).

(2) 1-(2-Diethylaminoethyl)-4-trifluoromethyl-6-(4-morpholinocarbonyl-1-butynyl)-3-hydroxy-3-(2-chlorophenyl)oxindole The title compound (26.5 mg) was prepared from 1-(2-diethylaminoethyl)-4-trifluoromethyl-6-iodo-3-hydroxy-3-(2-chlorophenyl)oxindole (35.2 mg, 0.0637 mmol) and 4-morpholinocarbonyl-1-butyne by the procedure similar to that described in Reference Example 21. The hydrochloride of the title compound was obtained by treating with 4 N HCl in dioxane followed by concentration to dryness.

¹H-NMR (DMSO-d₆: hydrochloride) δ 10.33 (brs, 1H), 8.06 (d, 1H, J=7.4 Hz), 7.64 (s, 1H), 7.46 (dd, 1H, J=7.4, 7.4 Hz), 7.12–7.39 (m, 4H), 4.11–4.34 (m, 1H), 3.20–3.65 (m, 14H), 2.68 (m, 4H), 1.24 (t, 6H, J=7.1 Hz).

Example 71

1-(2-Diethylaminoethyl)-4-trifluoromethyl-6-(2-morpholinocarboxy-1-ethynyl)-3-hydroxy-3-(2-naphthyl)oxindole (1) 1-(2-Diethylaminoethyl)-4-trifluoromethyl-6-(2-t-butoxycarbonyl-1-ethynyl)-3-hydroxy-3-(2-naphthyl)oxindole The title compound (75.7 mg, quant.) was prepared from 1-(2-diethylaminoethyl)-4-trifluoromethyl-6-iodo-3-hydroxy-3-(2-naphthyl)oxindole of Example 48 (75.1 mg, 0.132 mmol) and t-butyl propionate by the procedure similar to that described in Reference Example 21.

¹H-NMR (CDCl₃) δ 7.73–7.86 (m, 4H), 7.61 (s, 1H), 7.44–7.49 (m, 2H), 7.42 (s, 1H), 7.27 (dd, 1H, J=2.0, 8.6 Hz), 3.87–3.97 (m, 1H), 3.70–3.80 (m, 1H), 2.67 (t, 2H, J=6.3 Hz), 2.44–2.58 (m, 4H), 1.42 (s, 9H), 0.89 (t, 6H, J=7.1 Hz).

(2) 1-(2-Diethylaminoethyl)-4-trifluoromethyl-6-(2-carboxy-1-ethynyl)-3-hydroxy-3-(2-naphthyl)oxindole The hydrochloride of the title compound (72.8 mg, 100%) was obtained by treating 1-(2-diethylaminoethyl)-4-trifluoromethyl-6-(2-t-butoxycarbonyl-1-ethynyl)-3-hydroxy-3-(2-naphthyl)oxindole (73 mg, 0.129 mmol) with 4 N HCl in dioxane at 50° C. for 2 h followed by concentration to dryness.

¹H-NMR (DMSO-d₆) δ 7.83–7.97 (m, 5H), 7.54–7.56 (m, 3H), 7.14–7.31 (m, 1H), 4.22–4.26 (m, 2H), 3.17–3.54 (m, 6H), 1.13–1.23 (m, 6H).

(3) 1-(2-Diethylaminoethyl)-4-trifluoromethyl-6-(2-morpholinocarboxy-1-ethynyl)-3-hydroxy-3-(2-naphthyl)oxindole A solution of 1-(2-diethylaminoethyl)-4-trifluoromethyl-6-(2-carboxy-1-ethynyl)-3-hydroxy-3-(2-naphthyl)oxindole (35 mg, 0.064 mmol), morpholine hydrochloride (14.6 mg, 0.118 mmol), 1-hydroxybenzotriazole (11 mg, 0.0814 mmol), WSC HCl (14.7 mg, 0.0767 mmol), and triethylamine (0.04 mL, 0.287 mmol) in DMF (0.6 mL) was stirred for 21 h at room temperature and sat. aqueous NaHCO₃ was added. The mixture was extracted with ethyl acetate-toluene and the extracts were washed with sat. aqueous NaHCO₃, dried over MgSO$_4$, and concentrated. The residue was purified by silica gel column chromatography with 50:1 to 30:1 chloroform/methanol to give the title compound (2.5 mg, 4.6%).

$^1$H-NMR (DMSO-d$_6$) δ 7.73–7.81 (m, 4H), 7.45–7.55 (m, 3H), 7.22–7.30 (m, 2H), 3.48–3.96 (m, 10H), 2.51–2.71 (m, 6H), 0.89 (t, 6H, J=7.1 Hz).

Example 72

(+)-1-(2-Diethylaminoethyl)-4-trifluoromethyl-6-(4-morpholinocarbonyl-1-butynyl)-3-hydroxy-3-(2-chlorophenyl)oxindole (Optical Isomer of the Compound of Example 70)

(1) (+)- and (−)-1-(2-Diethylaminoethyl)-4-trifluoromethyl-6-iodo-3-hydroxy-3-(2-chlorophenyl)oxindole Racemic compound 1-(2-diethylaminoethyl)-4-trifluoromethyl-6-iodo-3-hydroxy-3-(2-chlorophenyl)oxindole was separated to (+)- and (−)-enantiomers by using a preparative HPLC on a Chiralpak OD™ with 6% isopropanol/hexane as the eluent. The enantiomeric excess was determined by using HPLC on a Chiralpak OD™ (250×4.6 mm) with 7% isopropanol/hexane as the eluent at the flow rate of 0.5 ml/min. Under these conditions, (+)- and (−)-enantiomers were eluted at the retention time of 20.8 and 16.7 min, respectively.

(+)-Enantiomer: $[α]_D$ +43.2° (c=0.210, MeOH); (−)-Enantiomer: $[α]_D$ −49.0° (c=0.220, MeOH).

(2) (+)-1-(2-Diethylaminoethyl)-4-trifluoromethyl-6-(4-morpholinocarbonyl-1-butynyl)-3-hydroxy-3-(2-chlorophenyl)oxindole The title compound (246 mg) was prepared from (+)-1-(2-diethylaminoethyl)-4-trifluoromethyl-6-iodo-3-hydroxy-3-(2-chlorophenyl)oxindole (300 mg, 0.543 mmol) and 4-morpholinocarbonyl-1-butyne by the procedure similar to that described in Reference Example 21. The hydrochloride of the title compound was obtained by treating with 4 N HCl in dioxane followed by concentration to dryness. The NMR spectra of the title compound exhibited the same as in Example 70. $[α]_D$ +58.3° (c=0.252, MeOH).

Example 73

(+)-1-(2-Diethylaminoethyl)-4-trifluoromethyl-6-[3-(N-ethylureido)-1-propynyl]-3-hydroxy-3-(2-chlorophenyl)oxindole (Optical Isomer of the Compound of Example 93)

(1) N-Ethyl-N'-propargylurea

To a solution of propargylamine (2 mL, 31.2 mmol) in THF (100 mL) was added dropwise ethyl isothionate (2.47 mL, 31.2 mmol) at 0° C. and the mixture was stirred for 30 min at room temperature. The solvent was evaporated and the residual solid was washed with ether to give the title compound (3.43 g, 87%).

$^1$H-NMR (CDCl$_3$) δ 4.75 (br, 2H), 4.02 (d, 1H, J=12.0 Hz), 3.96 (d, 1H, J=12.0 Hz), 3.23 (q, 2H, J=7.3 Hz), 2.22 (m, 1H), 1.14 (t, 3H, J=7.3 Hz).

(2) (+)-1-(2-Diethylaminoethyl)-4-trifluoromethyl-6-[3-(N-ethylureido)-1-propynyl]-3-hydroxy-3-(2-chlorophenyl)oxindole The title compound (232 mg) was prepared from (+)-1-(2-diethylaminoethyl)-4-trifluoromethyl-6-iodo-3-hydroxy-3-(2-chlorophenyl)oxindole of Example 72(1) (347 mg, 0.628 mmol) and N-ethyl-N'-propargylurea by the procedure similar to that described in Reference Example 21. The hydrochloride of the title compound was obtained by treating with 4 N HCl in dioxane followed by concentration to dryness.

$^1$H-NMR (DMSO-d$_6$) δ 10.36 (brs, 1H), 8.06 (d, 1H, J=6.9 Hz), 7.65 (s, 1H), 5 7.47 (dd, 1H, J=7.6, 7.6 Hz), 7.14–7.39 (m, 4H), 6.33 (brs, 1H), 6.06 (brs, 1H), 4.11–4.33 (m, 4H), 3.20–3.45 (m, 6H), 3.03 (q, 2H, J=7.1 Hz), 1.25 (t, 6H, J=7.1 Hz), 1.00 (t, 3H, J=7.1 Hz). $[α]_D$ +63.9° (c=0.504, MeOH).

Example 74

(+)-1-(2-Diethylaminoethyl)-4-trifluoromethyl-6-carbamoyl-3-hydroxy-3-(2-chlorophenyl)oxindole (Optical Isomer of the Compound of Example 78)

(1) (+)-1-(2-Diethylaminoethyl)-4-trifluoromethyl-6-cyano-3-hydroxy-3-(2-chlorophenyl)oxindole The title compound (335 mg, 63%) was prepared from (+)-1-(2-diethylaminoethyl)-4-trifluoromethyl-6-iodo-3-hydroxy-3-(2-chlorophenyl)oxindole of Example 72(1) (645 mg, 1, 17 mmol) by the procedure similar to that described in Example 55.

$^1$H-NMR (CDCl$_3$) δ 8.07 (d, 1H, J=7.6 Hz), 7.57 (s, 1H), 7.40–7.47 (m, 2H), 7.33 (ddd, 1H, J=1.5, 7.6, 7.6 Hz), 7.24 (dd, 1H, J=1.5, 7.9 Hz), 4.03–4.13 (m, 1H), 3.73–3.83 (m, 1H), 2.59–2.78 (m, 6H), 1.01 (t, 6H, J=7.1 Hz). $[α]_D$ +72.8° (c=0.338, MeOH).

(2) (+)-1-(2-Diethylaminoethyl)-4-trifluoromethyl-6-carbamoyl-3-hydroxy-3-(2-chlorophenyl)oxindole The title compound (248 mg, 66%) was prepared from (+)-1-(2-diethylaminoethyl)-4-trifluoromethyl-6-cyano-3-hydroxy-3-(2-chlorophenyl)oxindole (289 mg, 0.64 mmol) by the procedure similar to that described in Example 56.

$^1$H-NMR (DMSO-d$_6$: hydrochloride) δ 10.41 (brs, 1H), 8.33 (brs, 1H), 8.15 (s, 1H), 8.08 (d, 1H, J=7.3 Hz), 7.84 (s, 1H), 7.77 (brs, 1H), 7.48 (ddd, 1H, J=1.7, 7.6, 7.6 Hz), 7.11–7.40 (m, 4H), 4.16–4.36 (m, 2H), 3.25–3.51 (m, 6H), 1.26 (t, 6H, J=7.3 Hz). $[α]_D$ +75.7+ (c=0.412, MeOH).

Example 75

(+)-1-(2-Diethylaminoethyl)-4-trifluoromethyl-6-(3-methanesulfonylamino-1-propynyl)-3-hydroxy-3-(2-chlorophenyl)oxindole The title compound (270 mg) was prepared from (+)-1-(2-diethylaminoethyl)-4-trifluoromethyl-6-iodo-3-hydroxy-3-(2-chlorophenyl)oxindole of Example 72(1) (347 mg, 0.628 mmol) and 1-methanesulfonylamino-2-propyne by the procedure similar to that described in Reference Example 21. The hydrochloride of the title compound was obtained by treating with 4 N HCl in dioxane followed by concentration to dryness.

$^1$H-NMR (DMSO-d$_6$: hydrochloride) δ 10.40 (brs, 1H), 8.06 (d, 1H, J=7.6 Hz), 7.67–7.72 (m, 2H), 7.47 (dd, 1H, J=7.6, 7.6 Hz), 7.14–7.40 (m, 5H), 4.11–4.37 (m, 4H), 3.20–3.40 (m, 6H), 3.05 (s, 3H), 1.25 (t, 6H, J=7.3 Hz). $[α]_D$ +68.1° (c=0.228, MeOH).

Example 76

(−)-1-(2-Diethylaminoethyl)-4-trifluoromethyl-6-carbamoyl-3-hydroxy-3-(2-naphthyl)oxindole (Optical Isomer of the Compound of Example 56)

(1) (+)- and (−)-1-(2-Diethylaminoethyl)-4-trifluoromethyl-6-iodo-3-hydroxy-3-(2-naphthyl)oxindole Racemic compound 1-(2-diethylaminoethyl)-4-trifluoromethyl-6-iodo-3-hydroxy-3-(2-naphthyl)oxindole of Example 48 was separated to (+)- and (−)-enantiomers by using a preparative HPLC on a Chiralpak OD™ with 10% isopropanol/hexane as the eluent. The enantiomeric excess was determined by using HPLC on a Chiralpak OD™ (250×4.6 mm) with 12% isopropanol/hexane as the eluent at the flow rate of 0.5 ml/min. Under these conditions, (+)- and (−)-enantiomers were eluted at the retention time of 16.0 and 18.7 min, respectively.

(+)-Enantiomer: $[\alpha]_D$ +4.25° (c=0.574, MeOH); (−)-Enantiomer: $[\alpha]_D$ −1.82° (c 0.440, MeOH).

(2) Optically Active 1-(2-Diethylaminoethyl)-4-trifluoromethyl-6-cyano-3-hydroxy-3-(2-naphthyl)oxindole The title compound (298 mg, 59%) was prepared from (−)-1-(2-diethylaminoethyl)-4-trifluoromethyl-6-iodo-3-hydroxy-3-(2-naphthyl)oxindole (619 mg, 1.09 mmol) by the procedure similar to that described in Example 55. The NMR spectra of the title compound exhibited the same as in Example 55.

(3) (−)-1-(2-Diethylaminoethyl)-4-trifluoromethyl-6-carbamoyl-3-hydroxy-3-(2-naphthyl)oxindole The title compound (196 mg, 95%) was prepared from above optically active 1-(2-diethylaminoethyl)-4-trifluoromethyl-6-cyano-3-hydroxy-3-(2-naphthyl)oxindole (185 mg, 0.396 mmol) by the procedure similar to that described in Example 56.

$^1$H-NMR (DMSO-$d_6$: hydrochloride) δ 10.26 (brs, 1H), 8.38 (brs, 1H), 8.21 (brs, 1H), 7.79–7.92 (m, 6H), 7.48–7.53 (m, 2H), 7.20 (d, 1H, J=9.9 Hz), 7.08 (s, 1H), 4.21 (m, 2H), 3.20–3.44 (m, 6H), 1.21 (t, 6H, J=7.1 Hz). $[\alpha]_D$ −12.2° (c=0.118, MeOH).

Example 77

(+)-1-(2-Diethylaminoethyl)-4-trifluoromethyl-6-[4-(N-hydroxyethylcarbamoyl)-1-butynyl]-3-hydroxy-3-(2-chlorophenyl)oxindole The title compound (740 mg) was prepared from (+)-1-(2-diethylaminoethyl)-4-trifluoromethyl-6-iodo-3-hydroxy-3-(2-chlorophenyl)oxindole of Example 72(1) (102 mg, 0.185 mmol) and N-hydroxyethyl-4-pentynamide by the procedure similar to that described in Reference Example 21. The hydrochloride of the title compound was obtained by treating with 4 N HCl in dioxane followed by concentration to dryness.

$^1$H-NMR (DMSO-$d_6$: hydrochloride) δ 10.30 (brs, 1H), 8.01–8.09 (m, 2H), 7.64 (s, 1H), 7.46 (ddd, 1H, J=1.5, 7.4, 7.4 Hz), 7.14–7.40 (m, 4H), 4.70 (brs, 1H), 4.13–4.31 (m, 2H), 3.10–3.48 (m, 10H), 2.68 (t, 2H, J=7.3 Hz), 2.40 (t, 2H, J=7.3 Hz), 1.24 (t, 6H, J=7.1 Hz). $[\alpha]_D$ +66.2° (c=0.172, MeOH).

Example 78

1-(2-Diethylaminoethyl)-4-trifluoromethyl-6-carbamoyl-3-hydroxy-3-(2-chlorophenyl)oxindole (1) 1-(2-Diethylaminoethyl)-4-trifluoromethyl-6-cyano-3-hydroxy-3-(2-chlorophenyl)oxindole The title compound (316 mg, 64%) was prepared from 1-(2-diethylaminoethyl)-4-trifluoromethyl-6-iodo-3-hydroxy-3-(2-chlorophenyl)oxindole (600 mg, 1.09 mmol) by the procedure similar to that described in Example 74(1). The NMR spectra of the title compound exhibited the same as in Example 74(1).

(2) 1-(2-Diethylaminoethyl)-4-trifluoromethyl-6-carbamoyl-3-hydroxy-3-(2-chlorophenyl)oxindole The title compound (297 mg, quant.) was prepared from 1-(2-diethylaminoethyl)-4-trifluoromethyl-6-cyano-3-hydroxy-3-(2-chlorophenyl)oxindole (261 mg, 0.578 mmol) by the procedure similar to that described in Example 56. The NMR spectra of the title compound exhibited the same as in Example 74(2).

Example 79

1-(2-Diethylaminoethyl)-4-trifluoromethyl-6-ethoxycarbonyl-3-hydroxy-3-(2-naphthyl)oxindole A mixture of 1-(2-diethylaminoethyl)-4-trifluoromethyl-6-iodo-3-hydroxy-3-(2-naphthyl)oxindole of Example 48 (300 mg, 0.527 mmol), triethylamine (0.15 mL, 1.08 mmol), and (PPh$_3$)$_2$PdCl$_2$ (40 mg, 0.087 mmol) in a mixed solvent of ethanol (1.5 mL) and toluene (1.5 mL) was stirred for 7 h at 60° C. under CO atmosphere. Sat. aqueous NaHCO$_3$ was added and the mixture was extracted with ethyl acetate. The extracts were dried over MgSO$_4$ and concentrated. The residue was purified by silica gel column chromatography with 50:1 chloroform/methanol to give the title compound (273 mg, quant.).

$^1$H-NMR (CDCl$_3$) δ 8.06 (s, 1H), 7.90 (s, 1H), 7.87 (d, 1H, J=2.0 Hz), 7.72–7.81 (m, 3H), 7.44–7.49 (m, 2H), 7.21 (dd, 1H, J=2.0, 8.7 Hz), 4.47 (q, 2H, J=7.1 Hz), 3.78–3.99 (m, 2H), 2.74 (t, 2H, J=6.3 Hz), 2.57 (q, 4H, J=6.9 Hz), 1.45 (t, 3H, J=7.1 Hz), 0.95 (t, 6H, J=6.9 Hz).

Example 80

1-(2-Diethylaminoethyl)-4-trifluoromethyl-6-N,N-dimethylcarbamoyl-3-hydroxy-3-(2-naphthyl)oxindole To a solution of 1-(2-diethylaminoethyl)-4-trifluoromethyl-6-ethoxycarbonyl-3-hydroxy-3-(2-naphthyl)oxindole (43.4 mg, 0.0843 mmol) in a mixed solvent of methanol (0.2 mL) and THF (0.2 mL) was added 4 N aqueous NaOH (0.13 mL, 0.52 mL) and the mixture was stirred for 2 h at room temperature. The solvent was removed in vacuo and 4 N HCl in dioxane was added. The solvent was evaporated in vacuo again. The residue was dissolved in DMF (1 mL) and dimethylamine hydrochloride (125 mg, 0.153 mmol), 1-hydroxybenzotriazole (220 mg, 0.163 mmol), WSC HCl (309 mg, 0.161 mmol), and triethylamine (0.1 mL, 0.717 mmol). The mixture was stirred for 64 h at room temperature and sat. aqueous NaHCO$_3$ was added. The mixture was extracted with ethyl acetate-toluene and the extracts were washed with sat. aqueous NaHCO$_3$, dried over MgSO$_4$, and concentrated. The residue was purified by silica gel column chromatography with 50:1 to 20:1 chloroform/methanol to give the title compound (206 mg). The hydrochloride of the title compound was obtained by treating with 4 N HCl in dioxane followed by concentration to dryness.

$^1$H-NMR (DMSO-$d_6$: hydrochloride) δ 10.37 (brs, 1H), 7.83–7.94 (m, 4H), 7.79 (s, 1H), 7.49–7.52 (m, 2H), 7.41 (s, 1H), 7.20 (dd, 1H, J=2.0, 8.6 Hz), 7.06 (s, 1H), 4.20 (m, 2H), 3.00–3.48 (m, 6H), 3.05 (s, 3H), 3.03 (s, 3H), 1.20 (t, 6H, J=7.1 Hz).

Example 81

1-(2-Diethylaminoethyl)-4-trifluoromethyl-6-N-hydroxyethylcarbamoyl-3-hydroxy-3-(2-naphthyl)oxindole The title compound (18.7 mg, 26%) was prepared from 1-(2-diethylaminoethyl)-4-trifluoromethyl-6-ethoxycarbonyl-3-hydroxy-3-(2-naphthyl)oxindole (65.9 mg, 0.128 mmol) and 2-ethanolamine by the procedure similar to that described in Example 80.

$^1$H-NMR (DMSO-$d_6$: hydrochloride) δ 10.14 (brs, 1H), 8.95 (t, 1H, J=5.3 Hz), 8.21 (s, 1H), 7.79–7.92 (m, 6H), 7.48–7.52 (m, 2H), 7.20 (dd, 1H, J=1.5, 8.4 Hz), 7.10 (s, 1H), 4.18–4.23 (m, 2H), 3.17–3.72 (m, 10H), 1.21 (t, 6H, J=7.3 Hz).

Example 82

1-(2-Diethylaminoethyl)-4-trifluoromethyl-6-hydroxyethyl-3-hydroxy-3-(2-naphthyl)oxindole To a solution of 1-(2-diethylaminoethyl)-4-trifluoromethyl-6-ethoxycarbonyl-3-hydroxy-3-(2-naphthyl)oxindole (605 mg, 0. 118 mmol) in toluene (1 mL) was added dropwise 1.01 N diisobutylaluminium hydride in toluene (0.36 mL, 0.364 mmol). The mixture was allowed to warm to room temperature over 4 h. Sat. aqueous $NaHCO_3$ and ethyl acetate were added. Insoluble materials were removed by filtration and the organic layer was separated, dried over $MgSO_4$, and concentrated. The residue was purified by silica gel column chromatography with 30:1 to 15:1 chloroform/methanol to give the title compound (5 mg, 9%).

$^1$H-NMR ($CDCl_3$) δ 7.89 (s, 1H), 7.72–7.82 (m, 3H), 7.44–7.49 (m, 2H), 7.31 (s, 2H), 7.22 (dd, 1H, J=2.0, 8.6 Hz), 4.82 (s, 2H), 3.79–3.92 (m, 2H), 2.62–2.84 (m, 2H), 2.60 (q, 4H, J=7.1 Hz), 0.97 (t, 6H, J=7.1 Hz).

Example 83

1-(2-Diethylaminoethyl)-4-trifluoromethyl-6-N-methylcarbamoyl-3-hydroxy-3-(2-naphthyl)oxindole The title compound (10.4 mg, 20%) was prepared from 1-(2-diethylaminoethyl)-4-trifluoromethyl-6-ethoxycarbonyl-3-hydroxy-3-(2-naphthyl)oxindole (50.3 mg, 0.0978 mmol) and methylamine hydrochloride by the procedure similar to that described in Example 80.

$^1$H-NMR (DMSO-$d_6$: hydrochloride) δ 10.16 (brs, 1H), 8.94 (br, 1H), 8.19 (s, 1H), 7.79–7.92 (m, 5H), 7.48–7.52 (m, 2H), 7.17–7.25 (m, 1H), 7.10 (s, 1H), 4.18–4.22 (m, 2H), 3.20–3.44 (m, 6H), 2.87 (d, 3H, J=4.3 Hz), 1.21 (t, 6H, J=7.3 Hz).

Example 84

1-(2-Diethylaminoethyl)-3-hydroxy-3(2-chlorophenyl)-4-bromo-6-carbamoyloxindole (1) 1-(2-Diethylaminoethyl)-3-hydroxy-3-(2-chlorophenyl)-4-bromo-6-cyanooxindole To $Pd_2(dba)_3CHCl_3$ (60.1 mg, 5 mol %) and $PPh_3$ (60.9 mg, 20 mol %) under a nitrogen atmosphere was added anhydrous DMF (0.5 mL). The resulting precipitate was stirred at room temperature for 30 minutes during which time the colour changed from red to yellow/orange. To this was added 1-(2-diethylaminoethyl)-3-hydroxy-3-(2-chlorophenyl)-4-bromo-6-iodooxindole (626.4 mg, 1.16 mmol) dissolved in anhydrous DMF (1.0 mL). To the resulting red solution was then added $Zn(CN)_2$. The resulting precipitate was then heated to 60° C. (bath temperature) and stirring was continued at that temperature for 4 hours. The mixture was allowed to cool to room temperature and diluted with EtOAc:toluene (1:1, 10 mL). The mixture was washed with $H_2O$ (6 mL). The aqueous phase was then extracted with EtOAc:toluene (1:1, 5 mL×5). The organic phases were combined and dried (anhydrous $MgSO_4$). After filtration the solvent was removed in vacuo. The orange solid obtained was then purified by flash chromatography (silica gel, eluting 1% to 2% to 3%MeOH in $CHCl_3$) to give the title compound as a light brown/orange solid (462.6 mg, 91%).

$^1$H-NMR ($CDCl_3$, 270 MHz) δ 1.030 (6H, t, J=7.3 Hz), 2.666 (5H, m), 2.763 (1H, m), 3.679 (1H, ddd, J=11.6, 5.9 and 5.9 Hz), 4.109 (1H, ddd, J=14.6, 5.9 and 5.9 Hz), 7.140 (1H, d, J=1.3 Hz), 7.272–7.360 (2H, m), 7.410 (1H, d, J=1.0 Hz), 7.423 (1H, m), 8.197 (1H, dd, J=7.9 and 1.6 Hz).

(2) 1-(2-Diethylaminoethyl)-3-hydroxy-3(2-chlorophenyl)-4-bromo-6-carbamoyloxindole To 1-(2-diethylaminoethyl)-3-hydroxy-3-(2-chlorophenyl)-4-bromo-6-cyanooxindole (462.6 mg, 1.06 mmol) dissolved in anhydrous t-BuOH (30 mL) at 50° C. was added powdered KOH (1.2 g, 20 eq). The resulting solution was stirred for 1 hour and then cooled to room temperature. Ice was added and the mixture extracted with EtOAc (3×20 mL). The extracts were combined and dried (anhydrous $MgSO_4$). After filtration, the solvent was removed in vacuo to give a light brown solid. Purification was carried out by column chromatography (silica gel, eluting EtOAc:EtOH:$Et_3N$, 80:20:2) to yield the title compound as a white solid (346.5 mg, 69%).

$^1$H-NMR ($CDCl_3$, 270 MHz) δ 1.025 (6H, t, J=7.3 Hz), 2.619 (2H, q, J=6.9 Hz), 2.638 (2H, q, J=7.3 Hz), 2.725 (1H, m), 2.816 (1H, m), 3.836 (1H, m), 3.958 (1H, m), 5.828 (1H, brs), 6.486 (1H, brs), 7.201–7.344 (2H, m), 7.412 (1H, ddd, J=7.6, 1.3 and 1.3 Hz), 7.508 (2H, m), 8.236 (1H, dd, J=7.9 and 1.3 Hz).

Example 85

1-(2-Diethylaminoethyl)-3-hydroxy-3-(2-chlorophenyl)-4-bromo-6-[3-(N-ethylureido)-1-propynyl]oxindole To 1-(2-diethylaminoethyl)-3-hydroxy-3-(2-chlorophenyl)-4-bromo-6-iodooxindole (21.0 mg, 3.89×$10^{-5}$ mol), N-ethyl-N'-propargylurea (7.36 mg, 1.5 eq.), $Pd(PPh_3)_2Cl_2$ (4.10 mg, 15 mol %) and CuI (1.10 mg, 15 mol %) under a nitrogen atmosphere was added anhydrous $Et_3N$ (0.5 mL), anhydrous toluene (0.5 mL) and anhydrous THF (0.5 mL). The resulting yellow mixture was heated to 50° C. (bath temperature) and stirred at that temperature for 2 hours. The solvent was then removed in vacuo to give a yellow solid. Purification was carried out by column chromatography (silica gel, 10% MeOH in $CHCl_3$) to yield the title compound (18.8 mg, 86%) as a light brown solid.

$^1$H-NMR ($CDCl_3$, 270 MHz) δ 0.958 (6H, t, J=7.25 Hz), 0.993 (3H, t, J=7.3 Hz), 2.486–2.637 (3H, m), 3.014 (3H, m), 3.757 (1H, brt, J=6.6 Hz), 3.877 (0.67H, brd, J=5.6 Hz), 4.062 (1.33H, brd, J=5.9 Hz), 5.991 (1H, brt, J=5.6 Hz), 6.247 (1H, brt, J=5.6 Hz), 7.096 (1H, d, J=1.3 Hz), 7.128 (1H, d, J=1.3 Hz), 7.310 (1H, td, J=7.9 and 1.65 Hz), 7.359 (1H, td, J=7.9 and 1.65 Hz), 7.449 (1H, td, J=7.3 and 1.65 Hz), 8.126 (1H, dd, J=7.9 and 1.65 Hz).

Example 86

1-(2-Diethylaminoethyl)-4-bromo-6-[3-(2-oxo-1-imidazolidinyl)-1-propynyl]-3-hydroxy-3-(2-chlorophenyl)oxindole To 1-(2-diethylaminoethyl)-3-hydroxy-3-(2-chlorophenyl)-4-bromo-6-iodooxindole (25.0 mg, 4.64×$10^{-5}$ mol), 3-(2-oxo-1-imidazolidinyl)-1-propyne (8.6 mg, 1.5 eq.), $Pd(PPh_3)_2Cl_2$ (4.88 mg, 15 mol %) and CuI (1.32 mg, 15 mol %) under a nitrogen atmosphere was added anhydrous $Et_3N$ (0.5 mL), anhydrous toluene (0.5 mL) and anhydrous THF (0.5 mL). The resulting yellow mixture was heated to 50° C. (bath temperature) and stirred at that temperature for 1 hour 20 minutes. The solvent was then removed in vacuo to give a yellow solid. Purification was carried out by column chromatography (silica gel, 6% MeOH in $CHCl_3$) to yield the title compound (23.9 mg, 92%) as a light brown solid.

¹H-NMR (CDCl₃, 270 MHz) δ 1.183 (6H, t, J=7.3 Hz), 2.920 (5H, m), 3.122 (1H, m), 3.481 (3H, m), 3.602 (2H, m), 4.043 (1H, m), 4.194 (2H, s), 4.703 (1H, brs), 7.111–7.432 (5H, m), 8.226 (1H, dd, J=7.43 and 1.65 Hz).

Example 87

1-(2-Diethylaminoethyl)-4-bromo-6-[3-(2-oxo-1,3-oxazolin-3-yl)-1-propynyl]-3-hydroxy-3-(2-chlorophenyl)oxindole To 1-(2-diethylaminoethyl)-3-hydroxy-3-(2-chlorophenyl)-4-bromo-6-iodooxindole (31.5 mg, 5.84×10⁻⁵ mol), 3-(2-Oxo-1,3-oxazolin-3-yl)-1-propyne (10.95 mg, 1.5 eq.), Pd(PPh₃)₂Cl₂ (6.15 mg, 15 mol %) and CuI (1.7 mg, 15 mol %) under a nitrogen atmosphere was added anhydrous Et₃N (0.5 mL), anhydrous toluene (0.5 mL) and anhydrous THF (0.5 mL). The resulting yellow mixture was heated to 50° C. (bath temperature) and stirred at that temperature for 1 hour and 20 minutes. The solvent was then removed in vacuo to give a yellow solid. Purification was carried out by column chromatography (silica gel, 3% MeOH in CHCl₃) to yield the title compound (24.9 mg, 76%) as a white solid. The hydrochloride of the title compound was obtained by treating with 4 N HCl in dioxane followed by concentration to dryness.

¹H-NMR (DMSO-d₆, 270 MHz: Hydrochloride) δ 1.234 (6H, brt, J=6.6 Hz), 3.315 (8H, m), 3.683 (2H, t, J=7.6 Hz), 4.116 (1H, m), 4.201 (1H, m), 4.310 (2H, s), 7.253–7.497 (5H, m), 8.146 (1H, dd, J=7.4 and 1.65 Hz).

Example 88

1-(2-Diethylaminoethyl)-3-(2-chlorophenyl)-3-hydroxy-4-chloro-6-carboxamidooxindole (1) 1-(2-Diethylaminoethyl)-3-(2-chlorophenyl)-3-hydroxy-4-chloro-6-cyanooxindole To Pd₂(dba)₃CHCl₃ (5.69 mg, 5 mol %) and triphenylphosphine (5.76 mg, 20 mol %) under a nitrogen atmosphere was added anhydrous DMF (0.5 mL). The mixture was stirred at room temperature for 30 minutes to give orange/yellow mixture. To this was then added 1-(2-diethylaminoethyl)-3-hydroxy-3-(2-chlorophenyl)-4-chloro-6-iodooxindole (57.0 mg, 1.1×10⁻⁴ mol) followed by Zn(CN)₂ (17.2 mg, 0.8 eq., 60%). The resulting suspension was heated to 60° C. (bath temperature) and stirred at that temperature for 3 hours. The mixture was allowed to cool and diluted with EtOAc:toluene (10 mL, 1:1). The mixture was washed with H₂O (2×10 mL) and dried (anhydrous MgSO₄). After filtration the solvent was removed in vacuo to give the crude title compound.

¹H-NMR (CDCl₃, 270 MHz) δ 1.031 (6H, t, J=7.3 Hz), 2.6494 (6H, m), 3.732 (1H, m), 4.075 (1H, m), 7.231–7.480 (5H, m), 8.176 (1H, d, J=7.9 Hz).

(2) 1-(2-Diethylaminoethyl)-3-(2-chlorophenyl)-3-hydroxy-4-chloro-6-carboxamidooxindole The crude 1-(2-diethylaminoethyl)-3-(2-chlorophenyl)-3-hydroxy-4-chloro-6-cyanooxindole (1.1×10⁻⁴ mol) was dissolved in anhydrous t-BuOH (2 mL) and warmed to 50° C. (bath temperature), while stirring under a nitrogen atmosphere. Solid KOH (123 mg, 20 eq.) was added and the mixture stirred rapidly at 50° C. for 1 hour. The mixture was allowed to cool and ice (ca. 10 g) was added. The two phase mixture was then extracted with EtOAc (2×20 mL). The extracts were combined and dried (anhydrous MgSO₄). After filtration, the solvent was removed in vacuo. Purification was carried out by flash chromatography (silica gel, eluting 5% MeOH in CHCl₃ and EtOAc:EtOH:Et₃N, 80:10:2) to give the title compound (21.1 mg, 44% (two steps)).

¹H-NMR (CDCl₃, 270 MHz) δ 1.046 (6H, t, J=7.3 Hz), 2.676 (5H, m), 2.866 (1H, m), 3.816 (1H, m), 4.054 (1H, m), 5.800 (1H, brs), 6.522 (1H, brs), 7.160–7.307 (2H, m), 7.342 (1H, d, J=1.0 Hz), 7.414 (1H, dt, J=6.3 and 1.65 Hz), 7.464 (1H, s), 8.217 (1H, dd, J=6.6 and 1.0 Hz).

Example 89

1-(2-Diethylaminoethyl)-4-trifluoromethyl-6-[3-(2-oxo-1-imidazolidinyl)-1-propynyl]-3-hydroxy-3-(2-chlorophenyl)oxindole (1) 3-(2-oxo-1-Imidazolidinyl)-1-propyne To a suspension of ethylene urea (2.0 g, 23.2 mmol) in THF (80 mL) was added dropwise 1.47 N n-BuLi in hexane (15.8 mL, 23.2 mmol) at room temperature. 3-Bromopropyne (2.0 mL, 22.4 mmol) was added and the mixture was stirred for 30 min at room temperature then for 2 h at 50° C. Aqueous 5% KHSO₄ was added and the mixture was extracted with ethyl acetate. The Organic layers were dried over MgSO₄ and concentrated. The residue was purified by silica gel column chromatography with 1:1 to 0:1 hexane/ethyl acetate to give the title compound (641 mg, 22%).

¹H-NMR (CDCl₃) δ 4.74 (brs, 1H), 4.02 (d, 2H, J=2.4 Hz), 3.41–3.57 (m, 4H), 2.24 (t, 1H, J=2.4 Hz).

(2) 1-(2-Diethylaminoethyl)-4-trifluoromethyl-6-[3-(2-oxo-1-imidazolidinyl)-1-propynyl]-3-hydroxy-3-(2-chlorophenyl)oxindole A mixture of 1-(2-diethylaminoethyl)-4-trifluoromethyl-6-iodo-3-hydroxy-3-(2-chlorophenyl)oxindole (720 mg, 0.13 mmol), 3-(2-oxo-1-imidazolidinyl)-1-propyne (280 mg, 0.226 mmol), triethylamine (1 mL), CuI (12.8 mg, 0.0372 mmol), and (PPh₃)₂PdCl₂ (22.6 mg, 0.0322 mmol) in a mixed solvent of THF (0.5 mL) and toluene (0.5 mL) was stirred for 3 h at 50° C. Water and sat. aqueous NaHCO₃ were added and the mixture was extracted with ethyl acetate. The extracts were dried over MgSO₄ and concentrated. The residue was purified by silica gel column chromatography with 30:1 to 20:1 chloroform/methanol to give the title compound (625 mg). The compound was dissolved in dioxane (4 mL) and 4 N HCl in dioxane (1.5 mL) was added. The solvent was evaporated azeotropically with toluene. The residual solid was washed with ether and dried in vacuo to give the hydrochloride (583 mg, 77%).

¹H-NMR (DMSO-d₆: hydrochloride) δ 10.30 (brs, 1H), 8.06 (d, 1H, J=7.3 Hz), 7.71 (s, 1H), 7.16–7.49 (m, 5H), 6.63 (s, 1H), 4.12–4.33 (m, 4H), 3.26–3.50 (m, 10H), 1.24 (t, 6H, J=7.1 Hz).

Example 90

1-(2-Diethylaminoethyl)-4-trifluoromethyl-6-[3-(2-oxo-1,3-oxazolin-3-yl)-1-propynyl]-3-hydroxy-3-(2-chlorophenyl)oxindole (1) 3-(2-oxo-1,3-Oxazolin-3-yl)-1-propyne To a suspension of 2-oxazoline (1.0 g, 11.5 mmol) in THF (40 mL) was added 60% NaH (460 mg, 11.5 mmol) and 3-bromopropyne (1. 0 mL, 11.2 mmol). The mixture was stirred for 1 h at 50° C. then for 3 h at 60° C., poured into aqueous 5% KHSO₄, and extracted with ethyl acetate. The Organic layers were dried over MgSO₄ and concentrated. The residue was purified by silica gel column chromatography with 1:1 hexane/ethyl acetate to give the title compound (1.02 g, 71%).

¹H-NMR (CDCl₃) δ 4.37 (dd, 2H, J=7.1, 8.7 Hz), 4.10 (d, 2H, J=2.4 Hz), 3.67 (dd, 2H, J=7.1, 8.7 Hz), 2.31 (t, 1H, J=2.4 Hz).

(2) 1-(2-Diethylaminoethyl)-4-trifluoromethyl-6-[3-(2-oxo-1,3-oxazolin-3-yl)-1-propynyl]-3-hydroxy-3-(2-chlorophenyl)oxindole A mixture of 1-(2-diethylaminoethyl)-4-trifluoromethyl-6-iodo-3-hydroxy-3-(2-chlorophenyl)oxindole (796 mg, 0.144 mmol), 3-(2-oxo-1,3-oxazolin-3-yl)-1-propyne (464 mg, 0.371 mmol), CuI (10.8 mg, 0.0567 mmol), and $(PPh_3)_2PdCl_2$ (18.6 mg, 0.0265 mmol) in triethylamine (1 mL) was stirred for 4.5 h at 50° C. Water and sat. aqueous $NaHCO_3$ were added and the mixture was extracted with ethyl acetate. The extracts were dried over $MgSO_4$ and concentrated. The residue was purified by silica gel column chromatography with 80:1 to 50:1 chloroform/methanol to give the title compound (738 mg). The compound was dissolved in dioxane (2 mL) and 4 N HCl in dioxane (1 mL) was added. The solvent was evaporated azeotropically with toluene. The residual solid was washed with ether and dried in vacuo to give the hydrochloride (528 mg, 63%).

$^1$H-NMR (DMSO-$d_3$: hydrochloride) δ 10.48 (brs, 1H), 8.06 (d, 1H, J=7.9 Hz), 7.78 (s, 1H), 7.28–7.49 (m, 5H), 4.07–4.38 (m, 6H), 3.71 (dd, 2H, J=8.1, 8.1 Hz), 3.26–3.44 (m, 6H), 1.25 (t, 6H, J=7.1 Hz).

Example 91

1-(2-Diethylaminoethyl)-4-trifuoromethyl-6-carbamoyl-3-hydroxy-3-(2,4-dichlorophenyl) oxindole (1) (2-Diethylaminoethyl)-4-trifluoromethyl-6-iodo-3-hydroxy-3-(2,4-dichlorophenyl)oxindole To a solution of 1-(2-diethylaminoethyl)-4-trifluoromethyl-6-iodoisatin (150 mg, 0.341 mmol) in a mixed solvent of diethyl ether (2 mL) and toluene (1 mL) was added dropwise a freshly prepared 0.794 N 2,4-dichlorophenyl magnesium iodide in ether (0.45 mL, 0.387 mmol) at room temperature. The mixture was stirred for 1 h at the same temperature and the reaction was quenched with aqueous $NaHCO_3$. The mixture was extracted with ethyl acetate and the extracts were dried over $MgSO_4$ and concentrated. The residue was purified by silica gel column chromatography with 80:1 to 50:1 chloroform/methanol to give the title compound (111 mg, 55%).

$^1$H-NMR (CDCl$_3$) δ 8.03 (d, 1H, J=8.4 Hz), 7.61 (s, 1H), 7.54 (s, 1H), 7.39 (dd, 1H, J=2.0, 8.4 Hz), 7.26 (d, 1H, J=2.0 Hz), 3.98–4.08 (m, 1H), 3.68–3.80 (m, 1H), 2.51–2.79 (m, 6H), 1.02 (t, 6H, J=7.3 Hz).

(2) 1-(2-Diethylaminoethyl)-4-trifluoromethyl-6-cyano-3-hydroxy-3-(2,4-dichlorophenyl)oxindole The title compound (412 mg, 64%) was prepared from 1-(2-diethylaminoethyl)-4-trifluoromethyl-6-iodo-3-hydroxy-3-(2,4-dichlorophenyl)oxindole (782 mg, 0.138 mmol) by the procedure similar to that described in Example 55.

$^1$H-NMR (CDCl$_3$) δ 8.04 (d, 1H, J=8.6 Hz), 7.58 (d, 1H, J=0.7 Hz), 7.42 (d, 1H, J=0.7 Hz), 7.41 (dd, 1H, J=1.8, 8.6 Hz), 7.26 (d, 1H, J=1.8 Hz), 4.06–4.17 (m, 1H), 3.68–3.78 (m, 1H), 2.53–2.86 (m, 6H), 1.00 (t, 6H, J=7.1 Hz).

(3) 1-(2-Diethylaminoethyl)-4-trifluoromethyl-6-carbamoyl-3-hydroxy-3-(2,4-dichlorophenyl)oxindole To a solution of 1-(2-diethylaminoethyl)-4-trifluoromethyl-6-cyano-3-hydroxy-3-(2,4-dichlorophenyl) oxindole (315 mg, 0.648 mmol) in t-butanol (5 mL) was added powdered KOH (ca. 300 mg) at 50° C. The mixture was stirred for 30 min at the same temperature and passed through a celite pad. The celite was washed with THF and the filtrate was concentrated. The residue was dispersed between water and ethyl acetate and the organic layer was separated. The organic layer was dried over $MgSO_4$ and concentrated to give the title compound (248 mg, 66%). The compound was dissolved in dioxane (2.5 mL) and 4 N HCl in dioxane (0.5 mL) was added. The solvent was evaporated azeotropically with toluene to dryness to give the hydrochloride (331 mg, 94%).

$^1$H-NMR (DMSO-$d_6$: hydrochloride) δ 10.37 (brs, 1H), 8.35 (brs, 1H), 8.15 (s, 1H), 8.08 (d, 1H, J=8.9 Hz), 7.85 (s, 1H), 7.80 (brs, 1H), 7.50–7.61 (m, 3H), 4.13–4.39 (m, 2H), 3.16–3.47 (m, 6H), 1.26 (t, 6H, J=7.3 Hz).

Example 92

1-(2-Diethylaminoethyl)-4-trifluoromethyl-6-carbamoyl-3-hydroxy-3-(2,4-difluorophenyl) oxindole (1) 1-(2-Diethylaminoethyl)-4-trifluoromethyl-6-iodo-3-hydroxy-3-(2,4-difluorophenyl)oxindole To a solution of 1-bromo-2,4-difluorobenzene (0.13 mL, 1.15 mmol) in THF (7.5 mL) was added dropwise 1.47 N BuLi in hexane (0.77 mL, 1.13 mmol) at −78° C. and the mixture was stirred for 15 min. To the resulting solution was added dropwise a solution of 1-(2-diethylaminoethyl)-4-trifluoromethyl-6-iodoisatin (500 mg, 1.14 mmol) in THF (6 mL) over 15 min at −78° C. The mixture was stirred for 40 min at the same temperature and the reaction was quenched with aqueous $NaHCO_3$. The mixture was extracted with ethyl acetate and the extracts were dried over $MgSO_4$ and concentrated. The residue was purified by silica gel column chromatography with 80:1 to 50:1 chloroform/methanol to give the title compound (576 mg, 91%).

$^1$H-NMR (CDCl$_3$) δ 7.63 (s, 1H), 7.58 (s, 1H), 7.46–7.54 (m, 1H), 7.25–7.33 (m, 1H), 6.83–6.90 (m, 2H), 3.78–3.88 (m, 2H), 2.71 (t, 2H, J=6.4 Hz), 2.59 (q, 4H, J=7.1 Hz), 1.02 (dt, 6H, J=2.1, 7.1 Hz).

(2) 1-(2-Diethylaminoethyl)-4-trifluoromethyl-6-cyano-3-hydroxy-3-(2,4-difluorophenyl)oxindole The title compound (278 mg, 85%) was prepared from 1-(2-diethylaminoethyl)-4-trifluoromethyl-6-iodo-3-hydroxy-3-(2,4-difluorophenyl)oxindole (400 mg, 0.722 mmol) by the procedure similar to that described in Example 91(2).

$^1$H-NMR (CDCl$_3$) δ 7.51–7.60 (m, 2H), 7.49 (s, 1H), 7.26–7.36 (m, 1H), 6.82–6.93 (m, 2H), 3.77–3.94 (m, 2H), 2.72 (dt, 2H, J=2.4, 6.3 Hz), 2.58 (q, 4H, J=7.1 Hz), 0.99 (dt, 6H, J=2.2, 7.1 Hz).

3) 1-(2-Diethylaminoethyl)-4-trifluoromethyl-6-carbamoyl-3-hydroxy-3-(2,4-difluorophenyl)oxindole The title compound (234 mg, 88%) was prepared from 1-(2-diethylaminoethyl)-4-trifluoromethyl-6-cyano-3-hydroxy-3-(2,4-difluorophenyl)oxindole (238 mg, 0.525 mmol) by the procedure similar that described in Example 91.

$^1$H-NMR (DMSO-$d_6$: hydrochloride) δ 10.36 (brs, 1H), 8.34 (s, 1H), 8.15 (s, 1H), 7.73–7.87 (m, 2H), 6.99–7.47 (m, 4H), 4.19–4.35 (m, 2H), 3.21–3.40 (m, 6H), 1.25 (t, 6H, J=7.1 Hz).

Example 93

1-(2-Diethylaminoethyl)-4-trifluoromethyl-6-[3-(N-ethylureido)-1-propynyl]-3-hydroxy-3-(2-chlorophenyl)oxindole The title compound (206 mg, 48%) was prepared from 1-(2-diethylaminoethyl)-4-trifluoromethyl-6-iodo-3-hydroxy-3-(2-chlorophenyl)oxindole (408 mg, 0.738 mmol) by the procedure similar to that described in Example 73. The NMR spectra of the title compound exhibited the same as in Example 73.

Example 94

1-(2-Diethylaminoethyl)-4-trifluoromethyl-6-carbamoyl-3-hydroxy-3-(2,5-dichlorophenyl)oxindole (1) 1-(2-Diethylaminoethyl)-4-trifluoromethyl-6-iodo-3-hydroxy-3-(2,5-dichlorophenyl)oxindole The title compound (137 mg, 51%) was prepared from 1-(2-diethylaminoethyl)-4-trifluoromethyl-6-iodoisatin (200 mg, 0.454 mmol) and 2,5-dichlorobromobenzene by the procedure similar to that described Example 92(1).

$^1$H-NMR (CDCl$_3$) δ 8.08 (brs, 1H), 7.61 (s, 1H), 7.55 (s, 1H), 7.27 (dd, 1H, J=2.4, 8.6 Hz), 7.15 (d, 1H, J=8.6 Hz), 3.93–4.03 (m, 1H), 3.70–3.80 (m, 1H), 2.53–2.82 (m, 6H), 1.02 (t, 6H, J=7.1 Hz).

(2) 1-(2-Diethylaminoethyl)-4-trifluoromethyl-6-cyano-3-hydroxy-3-(2,5-dichlorophenyl)oxindole The title compound (585 mg, 81%) was prepared from 1-(2-diethylaminoethyl)-4-trifluoromethyl-6-iodo-3-hydroxy-3-(2,5-dichlorophenyl)oxindole (870 mg, 1.48 mmol) by the procedure similar to that described in Example 91(2).

$^1$H-NMR (CDCl$_3$) δ 8.08 (brs, 1H), 7.58 (s, 1H), 7.46 (s, 1H), 7.30 (dd, 1H, J=2.5, 8.3 Hz), 7.17 (d, 1H, J=8.3 Hz), 4.01–4.11 (m, 1H), 3.72–3.82 (m, 1H), 2.49–2.86 (m, 6H), 0.99 (t, 6H, J=7.1 Hz).

(3) 1-(2-Diethylaminoethyl)-4-trifluoromethyl-6-carbamoyl-3-hydroxy-3-(2,5-dichlorophenyl)oxindole The title compound (34.8 mg, 75%) was prepared from 1-(2-diethylaminoethyl)-4-trifluoromethyl-6-cyano-3-hydroxy-3-(2,5-dichlorophenyl)oxindole (41.7 mg, 0.0857 mmol) by the procedure similar to that described in Example 91.

$^1$H-NMR (DMSO-d$_6$: hydrochloride) δ 10.36 (brs, 1H), 8.35 (brs, 1H), 8.16 (s, 1H), 8.04 (d, 1H, J=2.6 Hz), 7.85 (s, 1H), 7.80 (brs, 1H), 7.63 (s, 1H), 7.48 (dd, 1H, J=2.6, 8.6 Hz), 7.37 (d, 1H, J=8.6 Hz), 4.16–4.39 (m, 2H), 3.24–3.45 (m, 6H), 1.26 (t, 6H, J=7.1 Hz).

Example 95

Optically Active 1-(2-Diethylaminoethyl)-4-trifluoromethyl-6-iodo-3-amino-3-(2-naphthyl)oxindole The title compound (206 mg, 48%) was prepared from (+)-1-(2-diethylaminoethyl)-4-trifluoromethyl-6-iodo-3-hydroxy-3-(2-naphthyl)oxindole of Example 76(1) (239 mg, 0.42 mmol) by the procedure similar to that described in Example 61(1). The NMR spectra of the title compound exhibited the same as in Example 61(1).

Example 96

Optically Active 1-(2-Diethylaminoethyl)-4-trifluoromethyl-6-carbamoyl-3-amino-3-(2-naphthyl)oxindole (1) Optically Active 1-(2-Diethylaminoethyl)-4-trifluoromethyl-6-cyano-3-amino-3-(2-naphthyl)oxindole The title compound (172 mg, 43%) was prepared from optically active 1-(2-diethylaminoethyl)-4-trifluoromethyl-6-iodo-3-amino-3-(2-naphthyl)oxindole of Example 95 (485 mg, 0.0855 mmol) by the procedure similar to that described in Example 91(2).

$^1$H-NMR (CDCld$_3$) δ 7.71–7.83 (m, 4H), 7.63 (s, 1H), 7.46–7.53 (m, 3H), 7.10 (dd, 1H, J=2.0, 8.6 Hz), 3.91–3.99 (m, 1H), 3.66–3.76 (m, 1H), 2.67–2.72 (m, 2H), 2.53 (q, 4H, J=7.2 Hz), 2.52 (brs, 2H), 0.93 (t, 6H, J=7.2 Hz).

(2) Optically Active 1-(2-Diethylaminoethyl)-4-trifluoromethyl-6-carbamoyl-3-amino-3-(2-naphthyl)oxindole The title compound (151 mg, 79%) was prepared from optically active 1-(2-diethylaminoethyl)-4-trifluoromethyl-6-cyano-3-amino-3-(2-naphthyl)oxindole (160 mg, 0.0343 mmol) by the procedure similar to that described in Example 91.

$^1$H-NMR (DMSO-d$_6$: hydrochloride) δ 10.31 (brs, 1H), 8.48 (brs, 1H), 8.36 (s, 1H), 8.00 (s, 1H), 7.82–7.94 (m, 5H), 7.50–7.61 (m, 2H), 7.16 (d, 1H, J=8.6 Hz), 4.18–4.41 (m, 2H), 3.13–3.81 (m, 6H), 1.23 (t, 6H, J=7.1 Hz).

Example 97

1-(2-Diethylaminoethyl)-3-hydroxy-3-(3-pyridyl)-4-bromooxindole

To a solution of n-BuLi (0.16 mL, 1.0 eq, 1.53 M in hexanes) at −78° C., in anhydrous Et$_2$O (1.0 mL), and under a nitrogen atmosphere was added a solution of 3-bromopyridine (40.8 mg, 0.0249 mL, 1.05 eq) in anhydrous Et$_2$O (0.5 mL). The resulting light yellow coloured precipitate was stirred at −78° C. for 30 minutes and then a solution of isatin 1-(2-diethylaminoethyl)-4-bromoisatin (80.0 mg, 2.46×10$^{-4}$), in anhydrous Et$_2$O (1.5 mL) was added dropwise. The solution was stirred for a further 7.5 hours. Saturated aqueous NH$_4$Cl (1.5 mL) was added to the resulting brown coloured reaction mixture and the reaction was allowed to warm to room temperature. The mixture was extracted with EtOAc and the combined extracts were dried (anhydrous Na$_2$SO$_4$). After filtration, the solvent was removed in vacuo. Purification was carried out by column chromatography (silica gel, 1% to 1.5% to 2% MeOH in CHCl$_3$) to yield the title compound as a light yellow oil (35.5 mg, 36%).

$^1$H-NMR (CDCl$_3$, 270 MHz) δ 0.946 (6H, t, J=7.3 Hz), 2.561 (4H, q, J=7.3 Hz), 2.706 (4H, m), 3.784 (2H, t, J=6.6 Hz), 6.916 (1H, dd, J=7.3 and 1.0 Hz), 7.174–7.305 (3H, m), 7.928 (1H, td, J=8.25 and 2.0 Hz), 8.413 (1H, d, J=2.0 Hz), 8.475 (1H, dd, J=4.95 and 1.3 Hz).

Example 98

1-(2-Diethylaminoethyl)-3-hydroxy-3-(3-quinolinyl)-4-bromooxindole

To 3-bromoquinoline (56.3 mg, 1.1 eq) in anhydrous Et$_2$O (1.0 mL) at −50° C. (internal temperature) and under a nitrogen atmosphere was added n-BuLi (0.18 mL, 1.1 eq, 1.53 M in hexanes). Stirring was continued for minutes and then to the resulting red/brown coloured precipitate was added 1-(2-diethylaminoethyl)-4-bromoisatin (80.0 mg, 2.46×10$^{-4}$ mol) in anhydrous Et$_2$O (2.0 mL) and the resulting dark blue coloured mixture was stirred for a further 8.5 hours at −50° C. Saturated aqueous NH$_4$Cl (1.5 mL) was added and the mixture was allowed to warm to room temperature. The mixture was extracted with EtOAc and the combined extracts were dried (anhydrous Na$_2$SO$_4$). After filtration, the solvent was removed in vacuo. Purification was carried out by flash chromatography (silica gel, eluting 2% MeOH in CHCl$_3$) to yield the title compound as a yellow oil (5.3 mg, 5%).

$^1$H-NMR (CDCl$_3$, 270 MHz) δ 0.964 (6H, t, J=7.3 Hz), 2.592 (2H, q, J=7.3 Hz), 2.604 (2H, q, J=7.3 Hz), 2.747 (2H, m), 3.830 (2H, m), 6.966 (1H, dd, J=7.1 and 1.0 Hz), 7.228–7.283 (2H, m), 7.549 (1H, t, J=8.25 Hz), 7.710 (1H, ddd, J=6.9, 1.3 and 1.3 Hz), 7.845 (1H, d, J=8.2 Hz), 8.443 (1H, d, J=2.3 Hz), 8.654 (1H, d, J=2.3 Hz).

Example 99

1-(2-Diethylaminoethyl)-3-hydroxy-3-(2-benzo[b]thienyl)-4-bromooxindole

To benzo[b]thiophene (86.8 mg, 2.1 eq) in anhydrous THF (2 mL) at −40° C. (bath temperature) was added n-BuLi (0.423 mL, 1.53 M in hexanes, 2.1 eq). The resulting colourless solution was stirred for 30 minutes, after which 1-(2-diethylaminoethyl)-4-bromoisatin (100.0 mg, 3.08× $10^{-4}$ mol) in anhydrous THF (2 mL) was added. Stirring was continued at −40° C. for 9 hours. Saturated aqueous $NH_4Cl$ (1.5 mL) was added and the mixture was allowed to warm to room temperature. The mixture was extracted with EtOAc and the combined extracts were dried (anhydrous $Na_2SO_4$). After filtration, the solvent was removed in vacuo. Purification was carried out by column chromatography (silica gel, eluting 1%–2% MeOH in $CHCl_3$) to give the title compound as a yellow oil (43.0 mg, 30%).

$^1$H-NMR ($CDCl_3$, 270 MHz) δ 0.970 (6H, t, J=7.3 Hz), 2.564 (2H, q, J=6.9 Hz), 2.578 (2H, q, J=7.3 Hz), 2.727 (2H, m), 3.792 (2H, m), 6.948 (1H, dd, J=6.9 and 2.3 Hz), 7.186 (1H, s), 7.305 (4H, m), 7.678 (1H, ddd, J=4.6, 3.7 and 3.0 Hz), 7.778 (1H, m).

Example 100

1-(2-Diethylaminoethyl)-3-hydroxy-3-(2-benzo[b]furanyl)-4-bromooxindole

To benzo[b]furan (76.4 mg, 2.1 eq) in anhydrous THF (2 mL) at −40° C. (bath temperature) was added n-BuLi (0.423 mL, 1.53 M in hexanes, 2.1 eq). The resulting light yellow coloured solution was stirred for 30 minutes, after which 1-(2-diethylaminoethyl)-4-bromoisatin (100.0 mg, 3.08× $10^{-4}$ mol) in anhydrous THF (2 mL) was added. Stirring was continued at −40° C. for 9 hours. Saturated aqueous $NH_4Cl$ (1.5 mL) was added and the mixture was allowed to warm to room temperature. The mixture was extracted with EtOAc and the combined extracts were dried (anhydrous $Na_2SO_4$). After filtration, the solvent was removed in vacuo. Purification was carried out by column chromatography (silica gel, eluting 1%–2% MeOH in $CHCl_3$) to give the title compound as a yellow oil (29.0 mg, 21%).

$^1$H-NMR ($CDCl_3$, 270 MHz) δ 0.992 (6H, t, J=6.9 Hz), 1.256 (1H, brs), 2.581 (2H, q, J=7.3 Hz), 2.596 (2H, q, J=6.9 Hz), 2.736 (2H, m), 3.836 (2H, m), 6.919 (1H, s), 6.943 (1H, dd, J=7.3 and 10.3 Hz), 7.249 (4H, m), 7.374 (1H, d, J=7.9 Hz), 7.552 (1H, m).

Example 101

1-(2-Diethylaminoethyl)-3-hydroxy-3-(3-benzo[b]thienyl)-4-bromooxindole

To 3-bromobenzo[b]thiophene (146.5 mg, 2.2 eq) in anhydrous THF (2 mL) at −40° C. (bath temperature) was added t-BuLi (0.40 mL, 1.70 M in pentane, 2.1 eq). The resulting light yellow coloured solution was stirred for 30 minutes, after which 1-(2-diethylaminoethyl)-4-bromoisatin (100.0 mg, 3.08×$10^{-4}$ mol) in anhydrous THF (2 mL) was added. Stirring was continued at −40° C. for 9 hours. Saturated aqueous $NH_4Cl$ (1.5 mL) was added and the mixture was allowed to warm to room temperature. The mixture was extracted with EtOAc and the combined extracts were dried (anhydrous $Na_2SO_4$). After filtration, the solvent was removed in vacuo. Purification was carried out by column chromatography (silica gel, eluting 1%–2% MeOH in $CHCl_3$) to give the title compound as a yellow/brown powder (119.3 mg, 84%).

$^1$H-NMR ($CDCl_3$, 270 MHz) δ 1.025 (6H, t, J=7.3 Hz), 2.616 (2H, q, J=7.3 Hz), 2.656 (2H, q, J=7.2 Hz), 2.705 (1H, m), 2.884 (1, ddd, J=13.5, 7.9 and 7.9 Hz), 3.732 (1H, ddd, J=12.5, 7.6 and 4.9 Hz), 4.061 (1H, ddd, J=14.2, 7.6 and 7.6 Hz), 6.930 (1H, d, J=7.3 Hz), 7.248 (3H, m), 7.393 (2H, m), 7.689 (1H, ddd, J=4.3, 2.6 and 2.6 Hz), 7.845 (1H, ddd, J=4.3, 2.6 and 2.6 Hz).

Example 102

1-(2-Diethylaminoethyl)-3-hydroxy-3-(3-thienyl)-4-bromooxindole

To 3-bromothiophene (105.5 mg, 2.1 eq) in anhydrous THF (2 mL) under a nitrogen atmosphere and with stirring was added t-BuLi (0.38 mL, 2.1 eq, 1.7 M in pentane) at −40° C. (bath temperature). Stirring was continued for 30 minutes after which 1-(2-diethylaminoethyl)-4-bromoisatin (100.0 mg, 3.08×$10^{-4}$ mol) in anhydrous THF (2 mL) was added dropwise. The resulting red colored solution was stirred at −40° C. for 8 hours. Saturated aqueous $NH_4Cl$ (1.5 mL) was added and the reaction mixture was allowed to warm to room temperature. The mixture was extracted with EtOAc and the combined extracts were dried (anhydrous $Na_2SO_4$). After filtration the solvent was removed in vacuo. Purification was carried out by column chromatography (silica gel, eluting 1% to 2% MeOH in $CHCl_3$) to give the title compound as a light brown foam (124.5 mg, 99%).

$^1$H-NMR ($CDCl_3$, 270 MHz) δ 1.037 (6H, t, J=7.3 Hz), 2.660 (4H, m), 2.724 (1H, m), 2.872 (1H, m), 3.736 (1H, ddd, J=14.2, 7.9 and 5.3 Hz), 4.017 (1H, ddd, J=14.5, 7.6 and 7.6 Hz), 6.893 (1H, d, J=5.3 Hz), 6.902 (1H, dd, J=7.3 and 1.0 Hz), 7.157–7.269 (3H, m), 7.301 (1H, d, J=5.3 Hz).

Example 103

1-(2-Diethylaminoethyl)-3-hydroxy-3-(3-furyl)-4-bromooxindole

To 3-bromofuran (95.1 mg, 2.1 eq) in anhydrous THF (2 mL) under a nitrogen atmosphere and with stirring was added t-BuLi (0.38 mL, 2.1 eq, 1.7 M in pentane) at −78° C. (bath temperature). Stirring was continued for 1 hour after which 1-(2-diethylaminoethyl)-4-bromoisatin (100.0 mg, 3.08×$10^{-4}$ mol) in anhydrous THF (2 mL) was added dropwise. The resulting red coloured solution was stirred at −40° C. for 8 hours. Saturated aqueous $NH_4Cl$ (1.5 mL) was added and the reaction mixture was allowed to warm to room temperature. The mixture was extracted with EtOAc and the combined extracts were dried (anhydrous $Na_2SO_4$). After filtration the solvent was removed in vacuo. Purification was carried out by column chromatography (silica gel, eluting 1% to 2% MeOH in $CHCl_3$) to give the title compound as a yellow solid (103.3 mg, 85%).

$^1$H-NMR ($CDCl_3$, 270 MHz) δ 1.207 (6H, t, J=7.3 Hz), 2.618 (4H, q, J=7.3 Hz), 2.746 (2H, m), 3.809 (2H, m), 6.431 (1H, d, J=2.0 Hz), 6.913 (1H, dd, J=7.3 and 1.6 Hz), 7.178–7.274 (3H, m), 7.398 (1H, d, J=2.0 Hz).

Example 104

1-(2-Diethylaminoethyl)-3-hydroxy-3-(2-indolyl)-4-bromooxindole

To indole (39.7 mg, 1.1 eq) in anhydrous THF (2 mL) under a nitrogen atmosphere and with stirring was added n-BuLi (0.22 mL, 1.1 eq, 1.53 M in hexanes) at −78° C. (bath temperature). Stirring was continued for 1 hour after which $CO_2$ (g) was bubbled through the solution for ca. 30 minutes. The reaction mixture was then allowed to warm to room temperature and stirred at room temperature for a further 30 minutes. The solvent was removed in vacuo to give a white/light yellow solid which was left under vacuum (10 mmHg) for 17 hours. To the thus dried solid under a nitrogen atmosphere was added anhydrous THF (2 mL). The resulting clear solution was cooled to −78° C. (bath temperature) and t-BuLi (0.20 mL, 1.1 eq, 1.7 M in pentane) added dropwise. The colourless solution was stirred for 1 hour and 1-(2-diethylaminoethyl)-4-bromoisatin (100.0 mg, $3.08 \times 10^{-4}$ mol) in anhydrous THF (2 mL) was added dropwise. The resulting red coloured solution was stirred at −40° C. for 7.5 hours. To the solution was added $H_2O$ (1.5 mL) and the mixture allowed to warm to room temperature. Saturated aqueous $NH_4Cl$ (1.5 mL) was then added. The mixture was extracted with EtOAc and the combined extracts were dried (anhydrous $Na_2SO_4$). After filtration the solvent was removed in vacuo. Purification was carried out by column chromatography (silica gel, eluting 1% to 1.5% MeOH in $CHCl_3$) to give the title compound as a red oil (39.4 mg, 29%).

$^1$H-NMR ($CDCl_3$, 270 MHz) δ 0.936 (6H, m, J=6.9 Hz), 2.564 (2H, q, J=7.3 Hz), 2.622 (2H, q, J=7.3 Hz), 2.735 (2H, m), 3.662 (1H, ddd, J=11.9, 5.6 and 5.6 Hz), 3.966 (1H, ddd, J=14.2, 6.9 and 6.9 Hz), 6.406 (1H, d, J=2.0 Hz), 6.883 (1H, dd, J=5.9 and 3.0 Hz), 7.047 (1H, t, J=7.3 Hz), 7.145 (1H, dt, J=7.7 and 1.0 Hz), 7.203–7.534 (4H, m), 9.530 (1H, brs).

Example 105

1-(2-Diethylaminoethyl)-3-hydroxy-3-(2-benzothiazolyl)-4-bromooxindole

To benzothiazole (83.3 mg, 2.0 eq) in anhydrous THF (2 mL) under a nitrogen atmosphere and with stirring was added n-BuLi (0.40 mL, 2.0 eq, 1.53 M in hexanes) at −78° C. (bath temperature). The resulting bright yellow coloured reaction mixture was stirred for 1 hour after which 1-(2-diethylaminoethyl)-4-bromoisatin (100.0 mg, $3.08 \times 10^{-4}$ mol) in anhydrous THF (2 mL) was added dropwise. The resulting red coloured solution was stirred at −78° C. for 7.5 hours. Saturated aqueous $NH_4Cl$ (1.5 mL) was added and the reaction mixture was allowed to warm to room temperature. The mixture was extracted with EtOAc and the combined extracts were dried (anhydrous $Na_2SO_4$). After filtration the solvent was removed in vacuo. Purification was carried out by column chromatography (silica gel, eluting 1% to 3% MeOH in $CHCl_3$) to give the title compound as a light yellow solid (20.7 mg, 15%).

$^1$H-NMR ($CDCl_3$, 270 MHz) δ 1.014 (6H, t, J=7.25 Hz), 1.256 (1H, brs), 2.622 (2H, q, J=6.9 Hz), 2.632 (2H, q, J=7.3 Hz), 2.699 (1H, m), 2.807 (1H, m), 3.814 (1H, m), 3.881 (1H, m), 6.981 (1H, d, J=7.6 Hz), 7.244 (2H, m), 7.308–7.488 (2H, m), 7.869 (1H, dd, J=8.25 and 1.3 Hz), 7.982 (1H, ddd, J=6.9, 0.7 and 0.7 Hz).

Example 106

1-(2-Diethylaminoethyl)-4-trifluoromethyl-6-cyano-3-hydroxy-3-(2-fluorophenyl)oxindole The title compound (10.9 mg, 74%) was prepared from 1-(2-diethylaminoethyl)-4-trifluoromethyl-6-iodo-3-hydroxy-3-(2-fluorophenyl)oxindole of Example 62(1) (18.1 mg) by the procedure similar to that described in Example 55.

$^1$H-NMR ($CDCl_3$, 300 MHz) δ 1.02 (6H, t, J=7.1 Hz), 2.88–2.57 (6H, m), 4.02–3.79 (2H, m), 6.93–6.86 (1H, m), 7.36–7.22 (2H, m), 7.47 (1H, s), 7.57 (1H, s), 7.91 (1H, t, J=7.1 Hz).

Example 107

1-(2-Diethylaminoethyl)-4-trifluoromethyl-6-carbamoyl-3-hydroxy-3-(2-fluorophenyl)oxindole The title compound was prepared from 1-(2-diethylaminoethyl)-4-trifluoromethyl-6-cyano-3-hydroxy-3-(2-fluorophenyl)oxindole of Example 106 by the procedure similar to that described in Example 56.

$^1$H-NMR (DMSO-$d_6$, 300 MHz) δ 1.22 (6H, brs), 3.37–3.20 (6H, m), 4.30–4.10 (2H, m), 7.06–6.97 (1H, m), 7.42–7.20 (3H, m), 7.85–7.70 (2H, m), 7.92 (2H, t, J=6.9 Hz), 8.27 (1H, s), 9.48 (1H, brs).

Example 108

1-(2-Diethylaminoethyl)-4,6-dichloro-3-amino-3-(2-naphthyl)oxindole

The title compound was prepared from 1-(2-diethylaminoethyl)-4,6-dichloro-3-hydroxy-3-(2-naphthyl)oxindole by the procedure similar to that described in Example 61(1).

$^1$H-NMR (DMSO-$d_6$, 300 MHz: hydrochloride) δ 1.18 (6H, t, J=7.2 Hz), 3.22 (4H, q, J=7.2 Hz), 3.30–3.45 (2H, m), 4.15 (2H, d, J=7.2 Hz), 7.31 (1H, dd, J=8.6, 1.8 Hz), 7.43 (1H, d, J=1.5 Hz), 7.56–7.61 (2H, m), 7.64 (1H, d, J=1.7 Hz), 7.91–7.96 (4H, m).

Example 109

1-(2-Diethylaminoethyl)-4-trifluoromethyl-6-(4-morpholinocarbonyl-1-butynyl)-3-hydroxy-3-(phenyl)oxindole (1) 1-(2-Diethylaminoethyl)-4-trifluoromethyl-6-iodo-3-hydroxy-3-(phenyl)oxindole The title compound (53%) was prepared from 1-(2-diethylaminoethyl)-6-iodo-4-trifluoromethylisatin and phenylmagnesium bromide by the procedure similar to that described in Example 1. The compound obtained was further purified by reverse phase HPLC with water-acetonitrile-trifluoroacetic acid.

$^1$H-NMR ($CDCl_3$, 300 MHz: trifluoroacetate) δ 0.95 (6H, t, J=7.2 Hz), 2.51–2.58 (4H, m), 2.63–2.68 (2H, m), 3.59–3.73 (1H, m), 3.80–3.89 (1H, m), 4.05 (1H, br), 7.23–7.33 (5H, m), 7.57 (1H, s), 7.65 (1H, s).

(2) 1-(2-Diethylaminoethyl)-4-trifluoromethyl-6-(4-morpholinocarbonyl-1-butynyl)-3-hydroxy-3-(phenyl)oxindole The title compound (65.2 mg, 88%) was prepared from 1-(2-diethylaminoethyl)-4-trifluoromethyl-6-iodo-3-hydroxy-3-(phenyl)oxindole (57.2 mg) and 4-morpholinocarbonyl-1-butyne (31.1 mg) by the procedure similar to that described in Reference Example 21. The compound obtained was further purified by reverse phase HPLC with water-acetonitrile-trifluoroacetic acid.

$^1$H-NMR (DMSO-$d_6$, 300 MHz: trifluoroacetate) δ 1.14–1.19 (6H, m), 2.68 (4H, s), 3.18–3.21 (4H, m), 3.28–3.29 (2H, m), 3.50–3.59 (6H, m), 3.98–4.15 (2H, m), 6.86 (1H, br), 7.15–7.18 (2H, m), 7.25–7.29 (3H, m), 7.35 (1H, s), 7.61 (1H, s), 9.50 (1H, br).

Example 110

1-Methyl-4,6-dichloro-3-(3-diethylaminopropoxy)-(2-naphthyl)oxindole (1) 1-Methyl-4,6-dichloroisatin A mixture of 60% NaH (20.5 mg), 4,6-dichloroisatin (947 mg), and iodomethane (0.328 mL) in THF (20 mL) were stirred overnight at room temperature, poured into 1 N hydrochloric acid, and extracted with ethyl acetate. The extracts were washed with sat. aqueous NaCl, dried over $MgSO_4$, and concentrated. The residue was washed with hexane to give the title compound (849 mg, 84%).

$^1$H-NMR (DMSO-$d_6$, 300 MHz) δ 3.12–3.11 (3H, m), 7.33–7.30 (2H, m).

(2) 1-Methyl-4,6-dichloro-3-hydroxy-(2-naphthyl)oxindole

The title compound (59.1 mg, 1.5%) was prepared from 1-methyl-4,6-dichloroisatin (250 mg) and 2-naphthyl magnesium bromide by the procedure similar to that described in Example 1.

$^1$H-NMR (CDCl$_3$, 300 MHz) δ 3.18 (3H, s), 3.96 (1H, brs), 6.85 (1H, d, J=1.8 Hz), 7.05 (1H, d, J=1.7 Hz), 7.28 (1H, dd, J=8.8, 2.0 Hz), 7.50–7.42 (2H, m), 7.81–7.73 (3H, m), 7.91 (1H, d, J=1.8 Hz).

(3) 1-Methyl-4,6-dichloro-3-(3-diethylaminopropoxy)-(2-naphthyl)oxindole

The title compound (5.0 mg, 5%) was prepared from 1-methyl-4,6-dichloro-3-hydroxy-(2-naphthyl)oxindole (59.1 mg) by the procedure similar to that described in Example 47. The compound obtained was further purified by reverse phase HPLC with water-acetonitrile-trifluoroacetic acid.

$^1$H-NMR (DMSO-$d_6$, 300 MHz: trifluoroacetate) δ 1.19 (6H, t, J=7.0 Hz), 2.03–1.89 (2H, m), 3.22 (3H, s), 3.40–3.07 (8H, m), 7.35–7.29 (2H, m), 7.53–7.46 (3H, m), 7.91–7.84 (4H, m).

Example 111

1-(5-Aminopentyl)-4-bromo-6-carbamoyl-3-hydroxy-3-(2-naphthyl)oxindole (1) 5-t-Butyldimethylsilyloxy-1-pentanol Sixty % NaH in mineral oil (1 g, 25 mmol) was washed with hexane and suspended in THF (50 mL). To the suspension was added dropwise 1,5-pentanediol (2.62 mL, 25 mmol) at 0° C. and the mixture was stirred for 30 min. t-Butyldimethylsilyl chloride (3.77 g, 25 mmol) was added and the mixture was stirred for 1 h at room temperature. The mixture was dispersed between ether and 5% $K_2CO_3$ and the organic layer was separated. The layer was dried over $MgSO_4$ and concentrated. The residue was purified by silica gel column chromatography with 4:1 to 1:1 hexane/ethyl acetate to give the title compound (3/16 g, 58%).

$^1$H-NMR (CDCl$_3$) δ 3.60–3.67 (m, 4H), 1.37–1.65 (m, 6H), 0.89 (s, 9H), 0.05 (s, 6H).

(2) 5-t-Butyldimethylsilyloxy-1-iodopentane

To a mixture of imidazole (1.13 g, 16.6 mmol), triphenyl phosphine (2.16 g, 8.24 mmol), and iodine (1.92 g, 7.56 mmol) in a mixed solvent of toluene (40 mL) and acetonitrile (4 mL) was added 5-t-butyldimethylsilyloxy-1-pentanol (1.5 g, 6.87 mmol). The mixture was stirred for 1 h at room temperature and aqueous $Na_2SO_3$ was added. The mixture was extracted with ethyl acetate and the extracts were dried over $MgSO_4$ and concentrated. The residue was purified by silica gel column chromatography with 10:1 hexane/ethyl acetate to give the title compound (1.55 g, 69%).

$^1$H-NMR (CDCl$_3$) δ 3.61 (t, 2H, J=6.1 Hz), 3.20 (t, 2H, J=7.1 Hz), 1.85 (tt, 2H, J=7.1, 7.1 Hz), 1.41–1.57 (m, 4H), 0.90 (s, 9H), 0.05 (s, 6H).

(3) 1-(5-t-Butyldimethylsilyloxypentyl)-4-bromo-6-iodoisatin

To a mixture of 4-bromo-6-iodoisatin (450 mg, 1.32 mmol) and 60% NaH (60 mg, 1.5 mmol) was added 5-t-butyldimethylsilyloxy-1-iodopentane (600 mg, 1.83 mmol). The mixture was stirred for 4 h at 50° C. and water and 5% $KHSO_4$ was added. The mixture was extracted with toluene-ethyl acetate and the extracts were washed with 5% $KHSO_4$, dried over $MgSO_4$, and concentrated. The residue was purified by silica gel column chromatography with 6:1 hexane/ethyl acetate to give the title compound (615 mg, 86%).

$^1$H-NMR (CDCl$_3$) δ 7.74 (s, 1H), 7.50 (s, 1H), 3.74 (t, 2H, J=7.4 Hz), 3.62 (t, 2H, J=6.1 Hz), 1.41–1.75 (m, 6H), 0.87 (s, 9H), 0.04 (s, 6H).

(4) 1-(5-t-Butyldimethylsilyloxypentyl)-4-bromo-6-iodo-3-hydroxy-3-(2-naphthyl)oxindole The title compound (463 mg, 75%) was prepared from 1-(5-t-butyldimethylsilyloxypentyl)-4-bromo-6-iodoisatin (500 mg, 0.923 mmol) and 2-naphthylmagnesium bromide by the procedure similar to that described in Example 1.

$^1$H-NMR (CDCl$_3$) δ 7.73–7.86 (m, 4H), 7.70 (s, 1H), 7.46–7.49 (m, 3H), 7.13 (dd, 1H, J=2.0, 8.6 Hz), 3.74–3.84 (m, 1H), 3.61–3.69 (m, 1H), 3.55 (t, 2H, J=6.3 Hz), 1.69–1.74 (m, 2H), 1.35–1.57 (m, 4H), 0.86 (s, 9H), 0.01 (s, 6H).

(5) 1-(5-Hydroxypentyl)-4-bromo-6-iodo-3-hydroxy-3-(2-naphthyl)oxindole

To a solution of 1-(5-t-butyldimethylsilyloxypentyl)-4-bromo-6-iodo-3-hydroxy-3-(2-naphthyl)oxindole (450 mg, 0.67 mmol) in THF (5 mL) was added 1 N n-tetrabutylammonium fluoride in THF (1 mL, 1 mmol) and the mixture was stirred for 4 h at room temperature. 5% $KHSO_4$ was added and the mixture was extracted with ethyl acetate. The extracts were dried over $MgSO_4$ and concentrated. The residue was purified by silica gel column chromatography with 1:1 to 0:1 hexane/ethyl acetate to give the title compound (349 mg, 94%).

$^1$H-NMR (CDCl$_3$) δ 7.73–7.86 (m, 4H), 7.70 (d, 1H, J=1.0 Hz), 7.44–7.51 (m, 3H), 7.14 (dd, 1H, J=1.8, 8.7 Hz), 3.61–3.83 (m, 3H), 3.57 (dt, 2H, J=1.4, 6.3 Hz), 1.38–1.77 (m, 6H).

(6) 1-(5-Methanesulfonyloxypentyl)-4-bromo-6-iodo-3-hydroxy-3-(2-naphthyl)oxindole To a solution of 1-(5-hydroxypentyl)-4-bromo-6-iodo-3-hydroxy-3-(2-naphthyl)oxindole (155 mg, 0.279 mmol) and triethylamine (0.06 mL, 0.43 mmol) in dichloromethane (5 mL) was added methanesulfonyl chloride (0.025 mL, 0.323 mmol) at 0° C. The mixture was stirred for 5 min at the same temperature and water was added. The mixture was extracted with ethyl acetate and the extracts were dried over $MgSO_4$ and concentrated. The residue was purified by silica gel column chromatography with 3:2 hexane/ethyl acetate to give the mixture (116 mg) of the title compound and dimesylate.

$^1$H-NMR (CDCl$_3$) δ 7.75–7.86 (m, 4H), 7.71 (d, 1H, J=0.7 Hz), 7.46–7.50 (m, 3H), 7.13 (dd, 1H, J=2.0, 8.6 Hz), 4.14 (t, 2H, J=6.3 Hz), 3.63–3.84 (m, 2H), 2.89 (s, 3H), 1.70–1.79 (m, 4H), 1.39–1.50 (m, 2H).

(7) 1-(5-di-t-Butoxycarbonylaminopentyl)-4-bromo-6-iodo-3-hydroxy-3-(2-naphthyl)oxindole A mixture of crude 1-(5-methanesulfonyloxypentyl)-4-bromo-6-iodo-3-hydroxy-3-(2-naphthyl)oxindole (85.9 mg), di-t-butyl iminodicarboxylate (102 mg, 0.469 mmol), $K_2CO_3$ (112 mg, 0.81 mmol), and a trace amount of KI in 2-butanone (2.5 mL) was heated at reflux for 3 h. Sat. aqueous NaCl was added and the mixture was extracted with ethyl acetate. The organic layers were dried over $MgSO_4$ and concentrated. The residue was purified by silica gel column chromatography with 4:1 hexane/ethyl acetate to give the title compound (101 mg).

$^1$H-NMR (CDCl$_3$) δ 7.70–7.87 (m, 5H), 7.45–7.52 (m, 3H), 7.12 (dd, 1H, J=2.0, 8.6 Hz), 3.60–3.82 (m, 2H), 3.53 (t, 2H, J=7.3 Hz), 1.32–1.85 (m, 6H), 1.48 (s, 18H).

(8) 1-(5-di-t-Butoxycatrbonylaminopentyl)-4-bromo-6-cyano-3-hydroxy-3-(2-naphthyl)oxindole The title compound (438 mg, 61% 2 steps) was prepared from 1-(5-di-t-butoxycarbonylaminopentyl)-4-bromo-6-iodo-3-hydroxy-3-(2-naphthyl)oxindole (81.5 mg, 0.108 mmol) by the procedure similar to that described in Example 55.

$^1$H-NMR (CDCl$_3$) δ 7.75–7.84 (m, 4H), 7.65 (s, 1H), 7.47–7.52 (m, 3H), 7.09 (dd, 1H, J=2.0, 8.6 Hz), 3.85 (s, 1H), 3.73–3.80 (m, 2H), 3.54 (t, 2H, J=7.3 Hz), 1.34–1.80 (m, 6H), 1.49 (s, 18H).

(9) 1-(5-t-Butoxycarbonylaminopentyl)-4-bromo-6-carbamoyl-3-hydroxy-3-(2-naphthyl)oxindole To a solution of 1-(5-di-t-butoxycarbonylaminopentyl)-4-bromo-6-cyano-3-hydroxy-3-(2-naphthyl)oxindole (400 mg, 0.612 mmol) in t-butanol (1.5 mL) was added powdered KOH (ca. 1 g) at 50° C. The mixture was stirred for 30 min at the same temperature and passed through a celite pad. The celite was washed with THF and the filtrate was concentrated. The residue was dispersed between water and ethyl acetate and the organic layer was separated. The organic layer was dried over MgSO$_4$ and concentrated. The residue was purified by silica gel column chromatography with 2:3 to 1:4 hexane/ethyl acetate to give the title compound (321 mg, 92%).

$^1$H-NMR (CDCl$_3$) δ 7.94 (s, 1H), 7.74–7.87 (m, 5H), 7.44–7.50 (m, 2H), 7.26 (brs, 1H), 7.15 (dd, 1H, J=2.0, 8.6 Hz), 5.81 (brs, 1H), 4.63 (br, 1H), 3.85 (brs, 1H), 3.68–3.81 (m, 2H), 3.13–3.19 (m, 2H), 1.72–1.86 (m, 2H), 1.38–1.54 (m, 4H), 1.42 (s, 9H).

(10) 1-(5-Aminopentyl)-4-bromo-6-carbamoyl-3-hydroxy-3-(2-naphthyl)oxindole

The hydrochloride of the title compound (220 mg, 85%) was obtained by treating 1-(5-t-butoxycarbonylaminopentyl)-4-bromo-6-carbamoyl-3-hydroxy-3-(2-naphthyl)oxindole (292 mg, 0.0511 mmol) with 4 N HCl in dioxane at room temperature for 2 h followed by concentration to dryness.

$^1$H-NMR (DMSO-d$_6$: hydrochloride) δ 8.40 (brs, 1H), 7.98 (s, 1H), 7.76–7.92 (m, 9H), 7.47–7.53 (m, 2H), 7.12 (d, 1H, J=8.6 Hz), 7.07 (s, 1H), 3.69–3.86 (m, 2H), 2.67–2.78 (m, 2H), 1.51–1.74 (m, 4H), 1.32–1.40 (m, 2H).

The structures of the compounds obtained in Examples 51 to 111 are shown below.

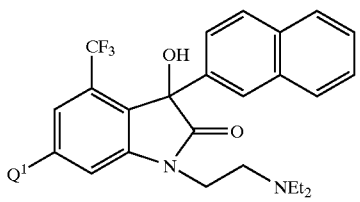

Example 51: Q$^1$ = 4-moropholinocarbonyl-1-butynyl
Example 52: Q$^1$ = 3-dimethylamino-1-propynyl
Example 53: Q$^1$ = 4-diethylcarbamoyl-1-butynyl
Example 54: Q$^1$ = 4-carboxy-1-butynyl
Example 55: Q$^1$ = cyano
Example 58: Q$^1$ = morpholinocarbonyl
Example 65: Q$^1$ = 4-carbamoyl-1-butynyl
Example 66: Q$^1$ = 3-amino-1-butynyl
Example 67: Q$^1$ = 3-ethylureido-1-propynyl
Example 68: Q$^1$ = 3-methanesulfonylamino-1-propynyl
Example 69: Q$^1$ = 4-(2-hydroxyethylcarbamoyl)-1-butynyl
Example 71: Q$^1$ = morpholinocarbonyl-ethynyl
Example 79: Q$^1$ = ethoxycarbonyl
Example 80: Q$^1$ = dimethylcarbamoyl
Example 81: Q$^1$ = (2-hydroxyethyl)carbamoyl
Example 82: Q$^1$ = hydroxymethyl
Example 83: Q$^1$ = methylcarbamoyl

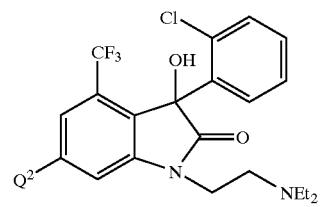

Example 70: Q$^2$ = 4-morpholinocarbonyl-1-butynyl
Example 75: Q$^2$ = 3-methanesulfonylamino-1-propynyl
Example 77: Q$^2$ = 4-(2-hydroxyethylcarbamoyl)1-butynyl
Example 89: Q$^2$ = 3-(2-oxo-1-imidazolidinyl)-1-propynyl
Example 90: Q$^2$ = 3-(2-oxo-1, 3-oxazolin-3-yl)-1-propynyl
Example 93: Q$^2$ = 3-ethylureido-1-propynyl

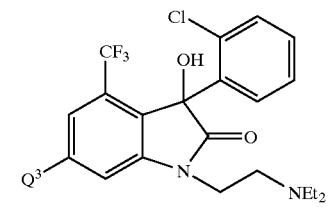

Example 84: Q$^3$ = cabamoyl
Example 85: Q$^3$ = 3-ethylureido-1-propynyl
Example 86: Q$^3$ = 3-(2-oxo-1-imidazolidinyl)-1-propynyl
Example 87: Q$^3$ = 3-(2-oxo-1, 3-oxazolin-3-yl)-1-propynyl

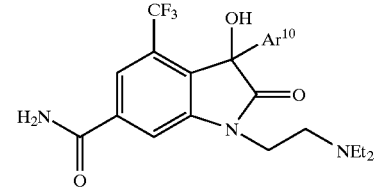

Example 56: Ar$^{10}$ = 2-naphthyl
Example 78: Ar$^{10}$ = 2-chlorophenyl
Example 91: Ar$^{10}$ = 2, 4-dichlorophenyl
Example 92: Ar$^{10}$ = 2, 4-difluorophenyl
Example 94: Ar$^{10}$ = 2, 5-dichlorophenyl
Example 107: Ar$^{10}$ = 2-fluorophenyl

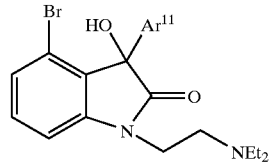

Example 97: Ar$^{11}$ = 3-pyridyl
Example 98: Ar$^{11}$ = 3-quinolinyl
Example 99: Ar$^{11}$ = 2-benzo[b]thienyl
Example 100: Ar$^{11}$ = 2-benzo[b]furyl
Example 101: Ar$^{11}$ = 3-benzo[b]thienyl
Example 102: Ar$^{11}$ = 3-thienyl
Example 103: Ar$^{11}$ = 3-furyl
Example 104: Ar$^{11}$ = 2-indolyl
Example 105: Ar$^{11}$ = 2-benzothiazolyl

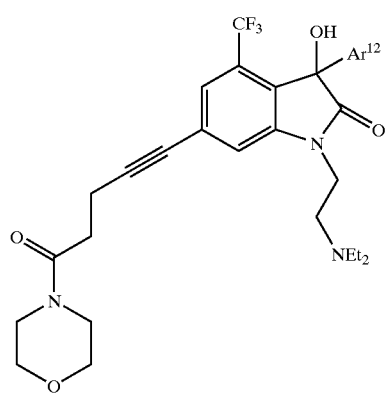
Example 62: Ar¹² = 2-fluorophenyl
Example 63: Ar¹² = 2-trifluoromethylphenyl.
Example 109: Ar¹² = phenyl
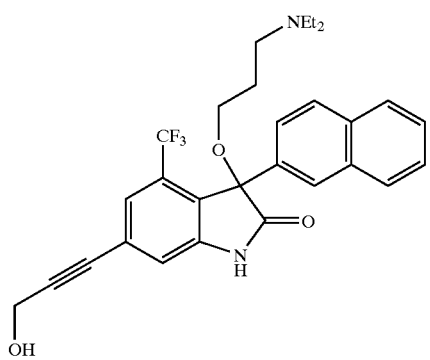
Example 57
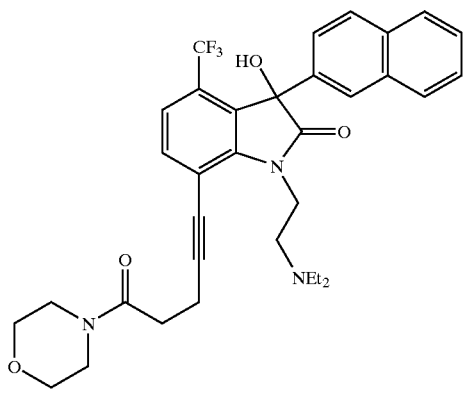
Example 59
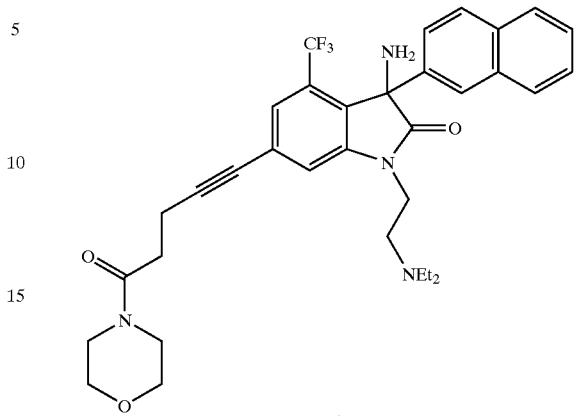
Example 61
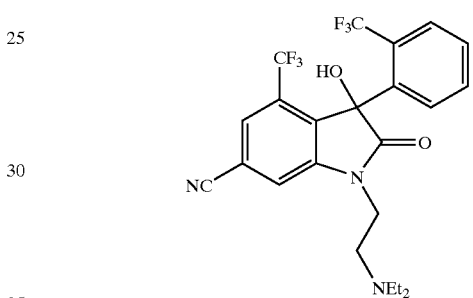
Example 64
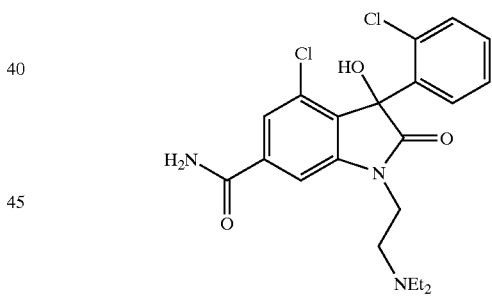
Example 88
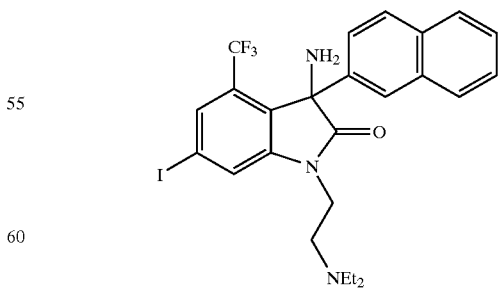
Example 95

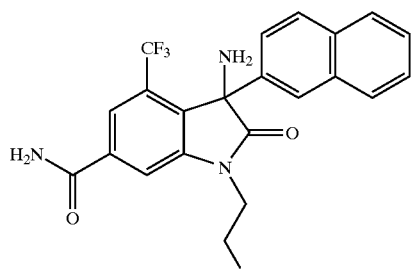

Example 96

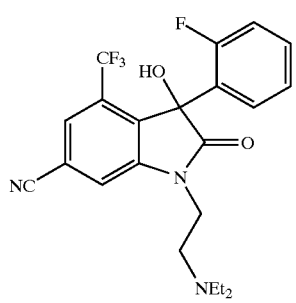

Example 106

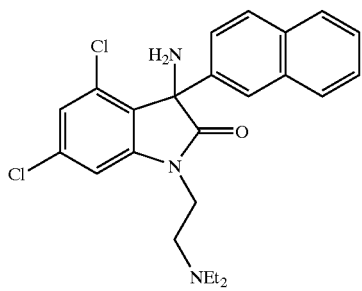

Example 108

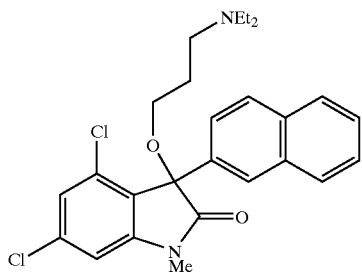

Example 110

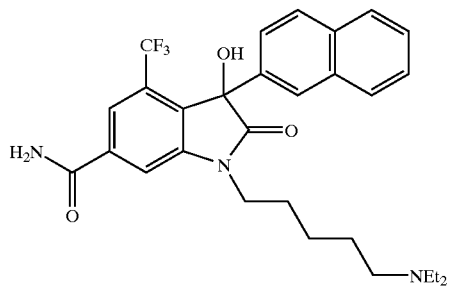

Example 111

Experiment 1

Biological Activity

Compounds of the present invention were evaluated for their growth hormone releasing activity from rat pituitary cells in vitro in accordance with the method described in the literature (R. G. Smith et al., Science, 260, 1640 (1993)).

Pituitary glands removed from 7-week-old Wistar/ST male rats were washed with HBSS (Hank's balanced salt solution) three times and minced into small pieces (ca. 1 mm$^2$) using a pair of scissors. The tissues were transferred to a 15 mL round-bottom centrifuge tube and washed with HBSS (10 mL×3). An enzyme solution (0.1 mL per a pituitary gland) was added and the cell dispersion was carried out in a water bath at 37° C. for ca 20–30 min, during which time the digested mixture was mixed by successive up-take and down-take of the suspension using a pipette, every 5 minutes. The resulting cell suspension was centrifuged at 1200 rpm for 2–3 min at room temperature and the supernatant fluid was discarded. A cultured medium was added and the resulting cell suspension was again centrifuged at 1200 rpm for 2–3 min at room temperature and the supernatant fluid was discarded. This procedure was repeated another 2 times. An aliquot (0.1 mL) of the resulting cell suspension was placed in each well of a 96-well plate in the number of 2×10$^4$ cells per a well and incubation was carried out at 37° C. under 5% $CO_2$ atmosphere for 5 days.

The culture medium was discarded and an assay medium (0.1 mL) was added. The incubation was continued for 1.5 h and the cells were washed with the assay medium. A test compound solution (0.1 mL) was added and the reaction was carried out at 37° C. for 15 min in an incubator under 5% $CO_2$ atmosphere. The supernatant fluid was recovered and the GH content present was measured by RIA (radioimmunoassay). An aliquot of the solution was diluted to 0.05 mL with a RIA buffer which consisted of PBS (pH 7.3) containing 1% BSA, 0.1% $NaN_3$ and 25 mM EDTA. The diluted solution, [$^{125}$I]-labeled GH solution (0.05 mL, ca. 10,000 cpm), and rabbit antiserum (1:10,000) against rat GH (0.05 mL) were placed in each well of a 96-well plate for RIA and the mixture was incubated for 3 days at 4° C. Cell membrane fractions containing protein A were added and the mixture was allowed to stand for 20 min and centrifuged. The supernatant fluid was removed and the precipitates were washed with the RIA buffer. The $^{125}$I content in the precipitates was measured. The GH concentration in the sample was calculated from the standard curve made by using the standard GH sample.

The $EC_{50}$ values of the test compounds were determined using recurrent calculation from the following equation, where X is the concentration of the test compound, Y is the GH concentration at the given assay, and B is the $EC_{50}$ value. C means recurrently calculated GH concentration in the absence of the test compound and A+C means recurrently calculated GH concentration when a maximum amount of the test compound is present.

$$Y=AX/(B+X)+C$$

The culture medium used here consisted of DMEM (Dulbecco's Modified Eagle's Medium) containing 10% horse serum, 2.5% fetal bovine serum, 1% nonessential amino acids, 0.01% streptomycin and penicillin (100 IU/mL). The cultured medium described above was adjusted to pH 7.3 by adding a 25 mM HEPES buffer and the resulting solution was used as the assay medium. A certain amount of the test compound was dissolved in DMSO, at which stage the concentration of the compound was 1000 times higher than the final concentration in the assay, and the aliquot (0.001 mL) was added to the assay medium (1 mL). The resulting mixture was used as the test compound solution. Collagenase (400 mg), DNase type I (1 mg), and BSA (1 g) were dissolved in a 25 mM HEPES buffer (pH 7.4, 40 mL) containing 0.8% NaCl, 0.037% KCl, 0.9% glucose, 0.01% streptomycin, penicillin (100 IU/mL), and 0.7 mM $Na_2HPO_4$ and 10 mg/mL aqueous $CaCl_2$ solution (0.226 mL). The resulting solution was adjusted to a final volume of 50 mL by adding a 25 mM HEPES buffer and sterilized by filtration through a 0.00022 mm filter. The resulting mixture was used as the enzyme solution.

The compound of Example 21, 70, 74 and 91 was evaluated for their GH releasing efficacy under the conditions described above and showed $EC_{50}$ values of 4, 5, 0.5 and 1.2 nM, respectively.

Experiment 2

Biological Activity

The compound of Example 74 (10 mg/kg/day×2) were administered orally to 11-week-old F 344/N rats (6/group) for 9 days and increase in the weight of each rat was measured. The drug-administered group showed significant increase in the weight of 19.5±2.1 g (p<0.01), whereas the distilled water-administered group showed 13.5±2.3 g.

Formulation Example

Preparation of Tablets

The compound of Example 91 (10 mg), lactose (72.5 mg), cornstarch (30 mg), and carboxymethyl cellulose calcium (5 mg) are mixed, agglomerated with an aqueous solution of hydroxypropyl cellulose (2 mg), and then mixed with magnesium stearate. The resulting mixture is compacted into a tablet of 120 mg.

Industrial Applicability

The present invention can provide an oxindole derivative or a prodrug thereof, or a pharmaceutically acceptable salt thereof useful for a growth hormone releaser.

What is claimed is:

1. An oxindole compound of Formula 1 or a prodrug thereof, or a pharmaceutically acceptable salt thereof:

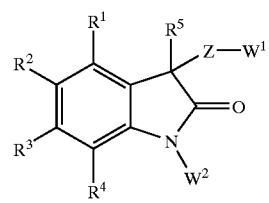

(1)

wherein
$R^1$ and $R^3$ are the same or different and each is independently hydrogen, optionally substituted alkyl, optionally substituted alkenyl, optionally substituted alkynyl, optionally substituted aryl, halogen, cyano, nitro, hydroxy, optionally substituted amino, alkoxy, alkanoyl, alkoxycarbonyl, optionally substituted sulfamoyl, optionally substituted carbamoyl, alkylthio, alkylsulfinyl, alkylsulfonyl, alkylsulfonylamino or alkanoylamino;
$R^2$ and $R^4$ are hydrogen;
provided that all of $R^1$, $R^2$, $R^3$ and $R^4$ are not simultaneously hydrogen;
$R^5$ is optionally substituted aryl;
—Z —O— is or —NH—;
$W^1$ is hydrogen;
$W^2$ is

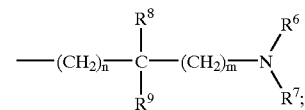

n is 1, 2 or 3; m is 0, 1, 2 or 3;
$R^6$ and $R^7$ are the same or different and each is independently optionally substituted alkyl or optionally substituted cycloalkyl; and
$R^8$ and $R^9$ are the same or different and each is independently hydrogen or optionally substituted alkyl; or $R^8$ and $R^9$ are taken together with the adjacent carbon atom to form optionally substituted cycloalkane.

2. An oxindole compound of Formula 2 or a prodrug thereof, or a pharmaceutically acceptable salt thereof:

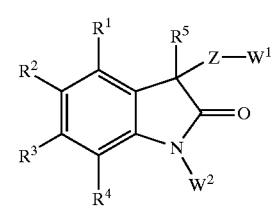

(2)

wherein
$R^1$ and $R^3$ are the same or different and each is independently hydrogen, trifluoromethyl, carbamoyl, halogen, 4-carbamoyl-1-butynyl, 4-alkylcarbamoyl-1-butynyl, 4-dialkylcarbamoyl-1-butynyl, 4-morpholinocarbonyl-1-butynyl, —C≡C—$(CH_2)_k$—Q, wherein k is 1 or 2; Q is hydroxy, alkylsulfonyl, alkanoylamino, alkylureido, 2-oxo-1-imidazolidinyl or 2-oxo-1,3-oxazolin-3-yl, provided that both of $R^1$ and $R^3$ are not simultaneously hydrogen;
$R^2$ and $R^4$ are hydrogen;
$R^5$ is optionally substituted aryl;
Z is —O— or —NH—;
$W^1$ is hydrogen;
$W^2$ is

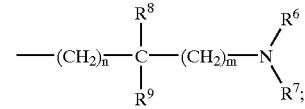

n is 1, 2 or 3; mis 0, 1, 2 or 3;
$R^6$ and $R^7$ are the same or different and each is independently optionally substituted alkyl or optionally substituted cycloalkyl; and
$R^8$ and $R^9$ are the same or different and each is independently hydrogen or optionally substituted alkyl; or $R^8$ and $R^9$ are taken together with the adjacent carbon atom to form optionally substituted cycloalkane.

3. An oxindole compound or a prodrug thereof, or a pharmaceutically acceptable salt thereof according to claim 2 wherein $R^1$ is trifluoromethyl, chlorine or bromine; and $R^3$ is carbamoyl, halogen, 4-carbamoyl-1-butynyl, 4-alkylcarbamoyl-1-butynyl, 4-dialkylcarbamoyl-1-butynyl, 4-morpholinocarbonyl-1-butynyl, —C≡C—$(CH_2)_k$—Q, wherein k is 1 or 2; Q is hydroxy, alkylsulfonyl, alkanoylamino, alkylureido, 2-oxo-1-imidazolidinyl or 2-oxo-1,3-oxazolin-3-yl.

4. An oxindole compound or a prodrug thereof, or a pharmaceutically acceptable salt thereof according to claim 2 wherein $R^1$ is trifluoromethyl, chlorine or bromine; and $R^3$ is carbamoyl.

5. An oxindole compound or a prodrug thereof, or a pharmaceutically acceptable salt thereof according to any one of claim 1, 2–4 wherein $R^5$ is optionally substituted phenyl or optionally substituted 2-naphthyl.

6. An oxindole compound or a prodrug thereof, or a pharmaceutically acceptable salt thereof according to any one of claim 1, 2–4 wherein $R^5$ is (i) phenyl optionally substituted by one or more substituents independently selected from the group consisting of halogen and trifluoromethyl; or (ii) 2-naphthyl optionally substituted by one or more substituents independently selected from the group consisting of halogen and trifluoromethyl.

7. An oxindole compound or a prodrug thereof, or a pharmaceutically acceptable salt thereof according to any one of claim 1 and 2 wherein $R^6$ and $R^7$ are independently optionally substituted alkyl; $R^8$ is hydrogen; and $R^9$ is hydrogen.

8. An oxindole compound, or a prodrug thereof, or a pharmaceutically acceptable salt thereof, according to claim 7, wherein $R^6$ and $R^7$ are independently methyl or ethyl.

9. An optical isomer of an oxindole compound according to any one of claim 1 and 2, of which the configuration at the C-3 position is equivalent to that of (+)-1-(2-diethylaminoethyl)-4-trifluoromethyl-6-carbamoyl-3-hydroxy-3-(2-chlorophenyl)oxindole, or a prodrug thereof, or a pharmaceutically acceptable salt thereof.

10. An oxindole compound selected from the following compounds, or a prodrug thereof, or a pharmaceutically acceptable salt thereof:

(+)-1-(2-diethylaminoethyl)-4-trifluoromethyl-6-(4-morpholinocarbonyl-1-butynyl)-3-hydroxy-3-(2-chlorophenyl)oxindole, (+)-1-(2-diethylaminoethyl)-4-trifluoromethyl-6-[3-(N-ethylureido)-1-propynyl]-3-hydroxy-3-(2-chlorophenyl)oxindole, (+)-1-(2-diethylaminoethyl)-4-trifluoromethyl-6-carbamoyl-3-hydroxy-3-(2-chlorophenyl)oxindole, (−)-1-(2-diethylaminoethyl)-4-trifluoromethyl-6-carbamoyl-3-hydroxy-3-(2-naphthyl)oxindole, 1-(2-diethylaminoethyl)-3-hydroxy-3-(2-chlorophenyl)-4-bromo-6-carbamoyloxindole, 1-(2-diethylaminoethyl)-4-trifluoromethyl-6-carbamoyl-3-hydroxy-3-(2,4-difluorophenyl)oxindole, and 1-(2-diethylaminoethyl)-4-trifluoromethyl-6-carbamoyl-3-hydroxy-3-(2,5-dichlorophenyl)oxindole.

11. A composition containing a therapeutically effective amount of an oxindole compound or a prodrug thereof, or a pharmaceutically acceptable salt thereof according to any one of claim 1 and 4 and a pharmaceutically acceptable carrier or diluent.

12. A method of releasing growth hormone comprising administering a therapeutically effective amount of an oxindole compound of Formula 3 or a prodrug thereof, or a pharmaceutically acceptable salt thereof to a human or a non-human mammal in need thereof:

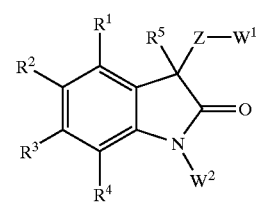

(3)

wherein $R^1$, $R^2$, $R^3$ and $R^4$ are the same or different and each is independently hydrogen, optionally substituted alkyl, optionally substituted alkenyl, optionally substituted alkynyl, optionally substituted aryl, halogen, cyano, nitro, hydroxy, optionally substituted amino, alkoxy, alkanoyl, alkoxycarbonyl, optionally substituted sulfamoyl, optionally substituted carbamoyl, alkylthio, alkylsulfinyl, alkylsulfonyl, alkylsulfonylamino or alkanoylamino, provided that all of $R^1$, $R^2$, $R^3$ and $R^4$ are not simultaneously hydrogen;

$R^5$ is optionally substituted aryl;

Z is —O— or —NH—;

one of $W^1$ and $W^2$ is hydrogen, alkyl or —Y—CON$(R^{10})R^{11}$;

the other of $W^1$ and $W^2$ is

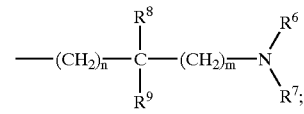

n is 1, 2 or 3; m is 0, 1, 2 or 3;

Y is single bond or $C_1$–$C_3$ alkylene;

$R^6$ and $R^7$ are the same or different and each is independently hydrogen, optionally substituted alkyl or optionally substituted cycloalkyl;

$R^8$ and $R^9$ are the same or different and each is independently hydrogen or optionally substituted alkyl; or $R^8$ and $R^9$ are taken together with the adjacent carbon atom to form optionally substituted cycloalkane; and $R^{10}$ and $R^{11}$ are the same or different and each is independently hydrogen or alkyl.

* * * * *